United States Patent
Yue et al.

(10) Patent No.: US 10,458,915 B2
(45) Date of Patent: *Oct. 29, 2019

(54) HETEROARYLCYANINE DYES

(71) Applicant: Pacific Biosciences of California, Inc., Menlo Park, CA (US)

(72) Inventors: Stephen Yue, Eugene, OR (US); Gene Shen, Santa Clara, CA (US); Wei-Chuan Sun, Mountain View, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/898,369

(22) Filed: May 20, 2013

(65) Prior Publication Data

US 2014/0005404 A1 Jan. 2, 2014

Related U.S. Application Data

(60) Provisional application No. 61/649,058, filed on May 18, 2012.

(51) Int. Cl.

| C07D 417/04 | (2006.01) |
|---|---|
| G01N 21/64 | (2006.01) |
| C07D 495/04 | (2006.01) |
| C09B 57/00 | (2006.01) |
| C07D 487/04 | (2006.01) |
| C09B 23/06 | (2006.01) |
| C09B 23/08 | (2006.01) |
| C09B 23/01 | (2006.01) |

(52) U.S. Cl.
CPC ....... *G01N 21/6486* (2013.01); *C07D 487/04* (2013.01); *C07D 495/04* (2013.01); *C09B 23/0066* (2013.01); *C09B 23/06* (2013.01); *C09B 23/08* (2013.01); *C09B 23/083* (2013.01); *C09B 57/00* (2013.01)

(58) Field of Classification Search
CPC .................................................. C07D 417/04
USPC ....................................................... 546/256
See application file for complete search history.

(56) References Cited

U.S. PATENT DOCUMENTS

| 4,711,955 A | 12/1987 | Ward et al. |
|---|---|---|
| 5,106,990 A | 4/1992 | Ohno et al. |
| 5,332,567 A | 7/1994 | Goldenberg |
| 5,627,027 A | 5/1997 | Waggoner |
| 5,688,648 A | 11/1997 | Mathies et al. |
| 5,808,044 A | 9/1998 | Brush et al. |
| 5,986,086 A | 11/1999 | Brush et al. |
| 6,114,350 A | 9/2000 | Randall et al. |
| 6,197,956 B1 | 3/2001 | Randall et al. |
| 6,224,644 B1 | 5/2001 | Randall et al. |
| 6,255,083 B1 | 7/2001 | Williams |
| 6,265,193 B1 | 7/2001 | Brandis et al. |
| 6,331,632 B1 | 12/2001 | Reedy |
| 6,399,335 B1 | 6/2002 | Kao et al. |
| 6,437,141 B2 | 8/2002 | Randall et al. |
| 6,544,797 B1 | 4/2003 | Buechler et al. |
| 6,917,726 B2 | 7/2005 | Levene et al. |
| 7,013,054 B2 | 3/2006 | Levene et al. |
| 7,033,764 B2 | 4/2006 | Korlach et al. |
| 7,041,812 B2 | 5/2006 | Kumar et al. |
| 7,052,839 B2 | 5/2006 | Nelson et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Turner et al. |
| 7,181,122 B1 | 2/2007 | Levene et al. |
| 7,223,541 B2 | 5/2007 | Fuller et al. |
| 7,292,742 B2 | 11/2007 | Levene et al. |
| 7,302,146 B2 | 11/2007 | Turner et al. |
| 7,393,640 B2 | 7/2008 | Kumar et al. |
| 7,777,013 B2 | 8/2010 | Xu |
| 7,968,702 B2 | 6/2011 | Wegener et al. |
| 7,973,146 B2 | 7/2011 | Shen |
| 8,058,031 B2 | 11/2011 | Xu |
| 8,133,702 B2 | 3/2012 | Shen |
| 8,148,516 B2 | 4/2012 | Williams et al. |
| 8,889,886 B2 | 11/2014 | Yue et al. |
| 8,993,737 B2 | 3/2015 | Shen |
| 9,315,864 B2 * | 4/2016 | Yue et al. ................. 546/276.7 |
| 2002/0156288 A1 | 10/2002 | Caputo et al. |
| 2003/0073866 A1 | 4/2003 | Kimura |
| 2003/0124576 A1 | 7/2003 | Kumar et al. |
| 2003/0190564 A1 | 10/2003 | Hioki et al. |
| 2004/0023413 A1 | 2/2004 | Opalsky |

(Continued)

FOREIGN PATENT DOCUMENTS

| EP | 1627635 A2 | 2/2006 |
|---|---|---|
| JP | 03-233444 A | 10/1991 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*
Atdbio.com. "Cyanine dyes—ATDBio." (Aug. 5, 2011). Accessed Jun. 30, 2019. Available from: < https://www.atdbio.com/content/32/Cyanine-dyes >. (Year: 2011).*
Licha, K., et al., Document No. 128:218365, retrieved from STN; Feb. 18, 1998, Accession No. 1998:93133 ZCAPLUS, "Synthesis and Characterization of Cyanine Dye-poly(Ethylene Glycol) Conjugates as Contrast Agents for in vivo Fluorescence Imaging").
Licha. K., et al., Document No. 125:81266, retrieved from STN; Jul. 25, 1996, Accesion No. 1996:437966 ZCAPLUS, "Dye-Biomolecule Conjugates as Contrast Agents for in-vivo near-IR Diagnostic Methods".

(Continued)

Primary Examiner — Andrew D Kosar
Assistant Examiner — John S Kenyon
(74) Attorney, Agent, or Firm — Morgan, Lewis & Bockius LLP

(57) ABSTRACT

The present invention provides heteroaryl functionalized cyanine dyes including a reactive functional moiety, or which are conjugated to a carrier molecule.

31 Claims, 6 Drawing Sheets

(56) References Cited

U.S. PATENT DOCUMENTS

| | | |
|---|---|---|
| 2005/0170367 A1 | 8/2005 | Quake et al. |
| 2005/0244863 A1 | 11/2005 | Mir |
| 2006/0240439 A1 | 10/2006 | Smith et al. |
| 2006/0281109 A1 | 12/2006 | Ost et al. |
| 2007/0036511 A1 | 2/2007 | Lundquist et al. |
| 2007/0072196 A1 | 3/2007 | Xu et al. |
| 2007/0099212 A1 | 5/2007 | Harris |
| 2007/0104649 A1 | 5/2007 | Fischer et al. |
| 2007/0161017 A1 | 7/2007 | Eid et al. |
| 2007/0196846 A1 | 8/2007 | Hanzel et al. |
| 2008/0267883 A1 | 10/2008 | Rajopadhye et al. |
| 2008/0277595 A1 | 11/2008 | Lundquist et al. |
| 2009/0186343 A1 | 7/2009 | Wang et al. |
| 2009/0208957 A1 | 8/2009 | Korlach |
| 2009/0233302 A1 | 9/2009 | Wegener et al. |
| 2009/0269759 A1 | 10/2009 | Menchen et al. |
| 2009/0275036 A1 | 11/2009 | Hardin et al. |
| 2009/0325260 A1 | 12/2009 | Otto |
| 2010/0136567 A1 | 6/2010 | Carter et al. |
| 2010/0152424 A1 | 6/2010 | Korlach |
| 2010/0255488 A1 | 10/2010 | Kong |
| 2010/0323389 A1 | 12/2010 | Xu |
| 2011/0313129 A1 | 12/2011 | Hu et al. |
| 2012/0052506 A1 | 3/2012 | Yue |
| 2012/0052507 A1 | 3/2012 | Shen |
| 2012/0058469 A1 | 3/2012 | Shen |
| 2012/0058473 A1 | 3/2012 | Yue |
| 2012/0058482 A1 | 3/2012 | Shen |
| 2012/0077189 A1 | 3/2012 | Shen |
| 2012/0329042 A1 | 12/2012 | Beechem et al. |

FOREIGN PATENT DOCUMENTS

| | | | | |
|---|---|---|---|---|
| JP | 03-284987 A | 12/1991 | | |
| JP | 2000-063690 A | 2/2000 | | |
| JP | 2000063690 A | * | 2/2000 | |
| JP | 2000-094834 A | 4/2000 | | |
| JP | 2001-222086 A | 8/2001 | | |
| JP | 2006-248180 A | 9/2006 | | |
| JP | 2009-191213 A | 8/2009 | | |
| JP | 2009191213 A | * | 8/2009 | ......... C09B 23/0016 |
| WO | WO 2000/035920 A2 | 6/2000 | | |
| WO | WO 2004/072238 A2 | 8/2004 | | |
| WO | WO 2005/033245 A1 | 4/2005 | | |
| WO | WO 2005/056689 A2 | 6/2005 | | |
| WO | WO 2006/111726 A1 | 10/2006 | | |
| WO | WO 2007/075873 | 7/2007 | | |
| WO | WO 2007/075987 | 7/2007 | | |
| WO | WO 2007/076057 | 7/2007 | | |
| WO | WO 2007/095119 | 8/2007 | | |
| WO | WO 2009/068751 | 6/2009 | | |
| WO | WO 2009/091847 | 7/2009 | | |
| WO | WO 2010/093726 A2 | 8/2010 | | |
| WO | WO 2012/054749 A1 | 4/2012 | | |
| WO | WO 2012/054784 A1 | 4/2012 | | |
| WO | WO 2013/189265 A1 | 12/2013 | | |

OTHER PUBLICATIONS

Abu El-Hamd, R.M., et al., "Some New Fused Heterocyclic Cyanine Dyes with Ring Junction Heteroatom," Chem. Papers, vol. 51, No. 2, p. 117-127 (1997).

Akeson, M. et al., "Microsecond time-scale discrimination among polycytidylic acid, polyadenylic acid, and polyuridylic acid as homopolymers or as segments within single RNA molecules," Biophys. J., 77:3227-3233 (1999).

Braslavsky, I. et al., "Sequence information can be obtained from single Dna molecules," Proc. Natl. Acad. Sci. USA, 100:3960-3964 (2003).

Chudinov, A.V. et al., Document No. 149:493676, retrieved from CAPLUS, Oct. 24, 2008.

Creighton, t.e. "Proteins—Structures and Molecular Properties," W.H. Freeman and Company, p. 5-8.

Eid. J., "Real-Time DNA Sequencing from Single Polymerase Molecules," Science, vol. 323, p. 133-138, 2009.

Fegan, Adrian et al., "Rigid Cyanine Dye Nucleic aciod Labels," Chem. Comm., 2008, 2004-2006; The Royal Society of Chemistry, 2008, p. 2004-2006.

Halpin, D.R. et al., "DNA Display III. Solid-Phase Organic Synthesis on Unprotected DNA," PLOS Biology, vol. 2, No. 7, p. 1031-1038 (2004).

Jett, J. H. et al., "High-speed DNA sequencing: An approach based upon fluorescence detection of single molecules," J. Biomol. Struct. Dynamics, 7:301-309 (1989).

Knorre, D.G., et al., "General Method for the Synthesis of ATP Gamma-Derivatives," FEBS Letters, vol. 70, No. 1 p. 105-108 (Nov. 1976).

Kumar, Shiv, et al., "Terminal Phosphate Labeled Nucleotides: Sunthesis, Applications, and Linker effect on Incorporation by DNA Polymerases," Nucleosides, Nucleotides, and Nucleic Acid, v. 24, No. 5-7, p. 401-408, (2005).

Lagerqvist, J. et al., "Fast DNA sequencing via transverse electronic transport," Nano Lett., 6:779-782 (2006).

Levene, M. J. et al., "Zero-mode waveguides for single-molecule analysis at high concentrations," Science, 299:682-686 (2003).

Lewis E.K.., et al., "Color-Blind Fluorescence Detection for Four-Color DNA Sequencing," Proc.Nat.Academy of Sci., vol. 102, No. 15, p. 5346-5351 (2005).

Metzker, M. L., "Emerging Technologies in DNA Sequencing," Genome Res., 15:1767-1776 (2005).

Rhee, K. J. et al., "Predicting the utilization of helicopter emergency medical services: an approach based on need," Annals of emergency medicine, 13:916-923 (1984).

Schuler, Benjamin et al., "Polyproline and the 'Spectroscopic Ruler' Revisited with Single-Molecule Fluorescence," PNAS, vol. 102, No. 8, p. 2754-2759 (Feb. 22, 2005).

Stephan, J. et al., "Towards a general procedure for sequencing single DNA molecules," J. Biotechnol., 86:255-267 (2001).

Wang, Li, et al., "Novel Asymmetric Cy5 Dyes: Synthesis, Photostabilities and High Sensitivity in Protein Fluorescence Labeling," J. of Photochem. and Photobio. A: Chem., vol. 210, p. 168-172, 2010.

Werner, J. H. et al., "Progress towards single-molecule DNA sequencing: a one color demonstration," J. Biotechnol., 102:1-14 (2003).

Narayanan, S., et al., "Clamping Down on Weak Terminal Base Pairs: Oligonucleotides with Molecular Caps as Fidelity-Enhancing Elements at the 5'- and 3'-Terminal Residues", Nucleic Acids Research, 2004, v. 32, n. 9, p. 2901-2911.

Ishchenko, A.A., et al., Journal of Information Recording Materials, v. 17, No. 1 p. 39-51, 1989.

USPTO Office Action in related U.S. Appl. No. 15/262,546 dated Oct. 16, 2018.

U.S. Appl. No. 13/218,395, filed Aug. 25, 2011.
U.S. Appl. No. 13/218,412, filed Aug. 25, 2011.
U.S. Appl. No. 13/218,428, filed Aug. 25, 2011.
U.S. Appl. No. 13/218,436, filed Aug. 25, 2011.
U.S. Appl. No. 14/085,616, filed Nov. 20, 2013 (now U.S. Pat. No. 9,315,864).
U.S. Appl. No. 13/218,395 filed Aug. 25, 2011 (now U.S. Pat. No. 8,669,374).
U.S. Appl. No. 13/218,428 filed Aug. 25, 2011 (now U.S. Pat. No. 8,889,886).
U.S. Appl. No. 13/218,436 filed Aug. 25, 2011 (now U.S. Pat. No. 8,993,737.
U.S. Appl. No. 13/218,439 filed Aug. 25, 2011.
U.S. Appl. No. 13/218,412 filed Aug. 25, 2011 (now U.S. Pat. No. 9,051,263).
U.S. Appl. No. 14/085,616 filed Nov. 20, 2013.
U.S. Appl. No. 14/489,143 filed Sep. 17, 2014.
U.S. Appl. No. 14/667,869 filed Mar. 25, 2015.
U.S. Appl. No. 14/729,988 filed Jun. 3, 2015.

* cited by examiner

HETEROARYLCYANINE DYES

FIELD OF INVENTION

The present invention relates generally to reactive fluorescent compounds that are cyanine dyes, analogues of cyanine dyes and to conjugates of these dyes with carrier molecules. Exemplary compounds of the invention are fluorophores that are derivatized to allow their facile attachment to another moiety. The invention also relates to improved methods for sequencing and genotyping nucleic acids in a single molecule configuration. An exemplary method involves detection of single molecules of fluorescent labels released from a nucleic acid during synthesis of an oligonucleotide.

BACKGROUND

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity, which characterizes many biochemical and biological systems. Frequently used methods are based on the interaction of two materials, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a variety of chemical, biochemical, and biological materials without significantly altering the important binding characteristics of those materials. Exemplary labels provide a highly characteristic signal, and should be rarely, and preferably never, found in natural forms of the interacting materials. The label should be stable and detectable in analytically relevant systems. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels is known, each with particular advantages and disadvantages. For example, radioactive labels are quite versatile, and can be detected at very low concentrations. However, such labels are expensive, hazardous, and their use requires sophisticated equipment and trained personnel. Thus, there is interest in non-radioactive labels, particularly labels that are observable by spectrophotometric, spin resonance, and luminescence techniques, and reactive materials, such as enzymes that produce such molecules.

Labels that are detectable using fluorescence spectroscopy are of particular interest because of the large number of such labels that are known in the art. Moreover, as discussed below, the literature is replete with syntheses of fluorescent labels that are derivatized to allow their attachment to other molecules, and many such fluorescent labels are commercially available.

Fluorescent nucleic acid probes are important tools for genetic analysis, in both genomic research and development, and in clinical medicine. As information from the Human Genome Project accumulates, the level of genetic interrogation mediated by fluorescent probes continues to expand enormously. One particularly useful class of fluorescent probes includes self-quenching probes, also known as fluorescence energy transfer probes, or FRET probes. The design of different probes using this motif may vary in detail. In an exemplary FET probe, both a fluorophore and a quencher are tethered to a common scaffold, e.g., a nucleic acid. Despite the limited availability of FRET probes, techniques incorporating their use are rapidly displacing alternative methods.

To enable the coupling of a fluorescent label with a group of complementary reactivity on a carrier molecule, a reactive derivative of the fluorophore is prepared. For example, Reedy et al. (U.S. Pat. No. 6,331,632) describe cyanine dyes that are functionalized at an endocyclic nitrogen of a heteroaryl moiety with hydrocarbon linker terminating in a hydroxyl moiety. The hydroxyl moiety is converted to the corresponding phosphoramidite, providing a reagent for conjugating the cyanine dye to a nucleic acid. Waggoner (U.S. Pat. No. 5,627,027) has prepared derivatives of cyanine and related dyes that include a reactive functional group through which the dye is conjugated to another species. The compounds set forth in Ohno et al. (U.S. Pat. No. 5,106,990) include cyanine dyes that have a $C_1$-$C_5$ hydrocarbyl linker terminated with a sulfonic acid, a carboxyl or a hydroxyl group. Randall et al. (U.S. Pat. Nos. 6,197,956; 6,114,350; 6,224,644; and 6,437,141) disclose cyanine dyes with a linker arm appended to an endocyclic heteroaryl nitrogen atom. The linkers include a thiol, amine or hydroxyl group, or a protected analogue of these residues. Additional linker arm-cyanine dyes are disclosed by Brush et al. (U.S. Pat. Nos. 5,808,044; 5,986,086). These cyanine dyes are derivatized at both endocyclic heteroaryl nitrogen atoms with a hydrocarbyl linker terminating in a hydroxyl moiety. One hydroxyl moiety is converted to the corresponding phosphoramidite and the other is protected as a dimethoxytrityl ether.

Cyanine dyes are particularly popular fluorophores and are widely used in many biological applications due to their high quantum yield and high molar absorptivity. Provision of cyanine dyes and conjugates of these dyes having an enhanced brightness and is an important object. Furthermore, it is generally desired to decrease adventitious binding of cyanine dyes such as proteins and surfaces, thereby enhancing the precision and accuracy of assays and other analyses utilizing cyanine fluorophores and their conjugates. The present invention meets these objects and other needs.

BRIEF SUMMARY OF THE INVENTION

The present invention provides a class of cyanine-based fluorophores modified to improve their fluorescent and other physicochemical properties. Thus, it is a general object of the invention to provide cyanine dyes that are hydrophilic, are resistant to photobleaching, or maintain a high level of brightness despite photobleaching, and have a lower tendency to stack or otherwise aggregate than current cyanine fluorophores.

Exemplary dyes and conjugates of the invention find particular use in DNA sequencing modalities, particularly single molecule sequencing modalities. Previous dyes used in such applications have less than ideal properties. For example, certain dyes give suboptimal performance, because, as was discovered, the dyes are insufficiently hydrophilic, insufficiently bright, do not emit steadily (i.e., blink), undergo photobleaching upon prolonged irradiation, or they aggregate. These deficiencies can cause misreads in DNA sequencing analyses, providing inaccurate results.

In various embodiments, the present invention provides dyes and conjugates that mitigate one or more of these factors contributing to suboptimal dye performance. In various embodiments, the hydrophilicity of the dyes is enhanced by the addition to the cyanine core or a side group attached to the cyanine core of a water-soluble polymer, or ionizable moiety (e.g., sulfonic acid, or carboxylic acid moieties or groups containing sulfonic acid or carboxylic acid moieties). Moreover, it was discovered that substitution of a cyanine dye with charged, hydrophilic moieties protects the cyanine chromophore from the dye's microenvironment and reduces blinking, aggregation and photobleaching. Thus, in various embodiments, the dyes of the invention are brighter, more photostable, and their emission is more constant. Furthermore, for DNA sequencing, particularly single molecule sequencing, resolution of the absorbance of the dye emissions is important to sensitivity and accuracy of the measurements underlying the sequence determination. Accordingly, in various embodiments, the present invention provides dyes with emissions tuned to achieve useful levels of resolution in the emission peaks of the dyes when they are used in combinations of 2, 3, 4 or more different dyes attached to nucleic acids.

In exemplary embodiments, the dyes and conjugates of the invention are utilized in DNA sequencing in real time using a single polymerase enzyme attached to the bottom of the small nanometer size aperture called a zero-mode waveguide (ZMW). Fluorescent signals of 4 different colors that correspond to 4 different DNA bases: A, G, C, T are detected in this method. Since the most robust methodologies read through as many bases on a template oligonucleotide as possible, it is desirable to utilize dyes that do not limit the readlength or the accuracy of the measurements.

In exemplary embodiments, the invention provides heteroaryl-derivatized cyanine dyes having one or more ionizable groups such as sulfonic or carboxylic acids and conjugates of these dyes with a carrier molecule. Exemplary fluorophores of the invention also include within their structure(s) a versatile linker arm, the structure and position of which is readily alterable, thereby allowing the conjugation of the label through a variety of positions on the cyanine nucleus to a carrier molecule. The cyanine-based labels are readily attached to a label, such as a nucleic acid, using techniques well known in the art, or modifications of such techniques that are well within the abilities of those of ordinary skill in the art. The versatility of the labels set forth herein provides a marked advantage over currently utilized cyanine labels, probes assembled using those labels and methods relying upon such labels and probes. Moreover, the present invention provides a class of chemically versatile labels in which the fluorophore can be engineered to have a desired fluorescence excitation and emission profile.

In an exemplary embodiment, the present invention provides a fluorescent compound having the formula:

A-Q-B wherein the symbol Q represents a moiety with a formula which is a member selected from:

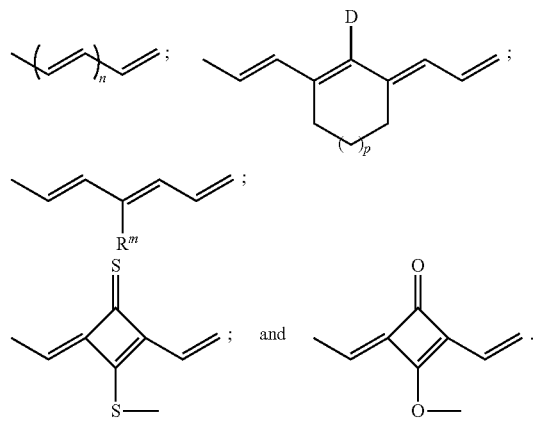

The symbol D represents a member selected from H, halogen, $OR^a$, $SR^a$, $NR^aR^b$, $CR^aR^bR^c$,

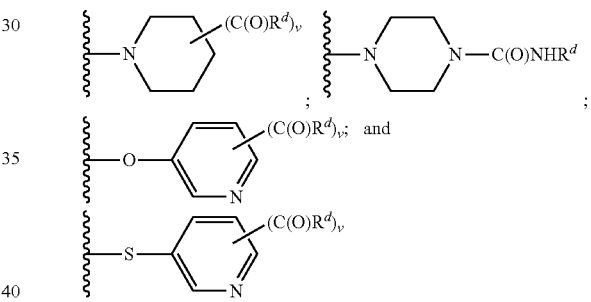

in which $R^a$, $R^b$, $R^c$ and $R^d$ are members independently selected from H, $R^8$, $R^8Z^o$, $SO_3H$, $C(O)Z^o$, $R^8SO_3H$,

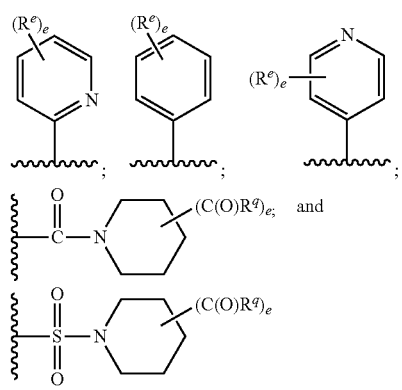

$Z^o$ and $R^q$ are independently selected from OH, O—, a reactive functional group, a component of a reactive functional group or is a linkage fragment covalently binding the compound to a carrier molecule. The index v is 0, 1, 2, 3, 4 or 5 and, when v is two or greater, each $R^d$ is independently selected. $R^e$ is selected from H, $R^{18}$, $R^{18}Z^1$, $SO_3H$, $CO_2H$, $R^{18}SO_3H$, $CONHR^{18}SO_3H$, and $CONHR^{18}C(O)Z^1$. The index e is 0, 1, 2, 3, 4, or 5 and, when e is two or greater, each $R^q$ is independently selected. $R^8$ and $R^{18}$ are independently selected from a bond and a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, $R^8$ and $R^{18}$ are independently selected from substituted or unsubstituted alkyl having from 1 to 20 carbon atoms. $Z^1$ is OH, O—, a reactive functional group, a component of a reactive functional group or a linkage fragment covalently binding the compound to a carrier molecule. The index n is 1, 2 or 3. The index p is 0, 1 or 2. $R^m$ is a member selected from:

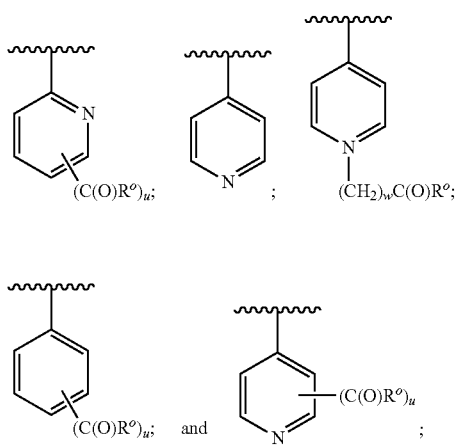

The index w is an integer from 1 to 10. $R^o$ is OH, O—, a reactive functional group, a component of a reactive functional group or is a linkage fragment covalently binding the compound to a carrier molecule. The index u is 0, 1, 2, 3, 4 or 5 and, when u is 2 or greater, each $R^o$ is independently selected.

B is a moiety which is a member selected from Formulae I, II and III;

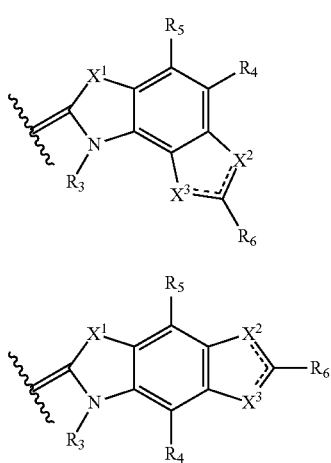

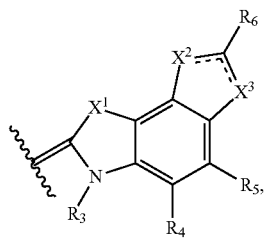

in which $X^1$ is a member selected from $CR^1R^2$, O, S and $NR^1$. $R^1$, $R^2$ and $R^3$ are independently $CH_2R^7$. $X^2$ and $X^3$ are members independently selected from O, S, N, NH, $CR^{22}$, and $CR^{22}R^{23}$. $R^4$, $R^5$, $R^6$, $R^7$, $R^{22}$ and $R^{23}$ are members independently selected from H, $R^{28}$, $R^{28}Z^2$, $SO_3H$, $COZ^2$, $R^{28}SO_3H$, $C(O)NHR^{28}SO_3H$, $CONHR^{28}COZ^2$,

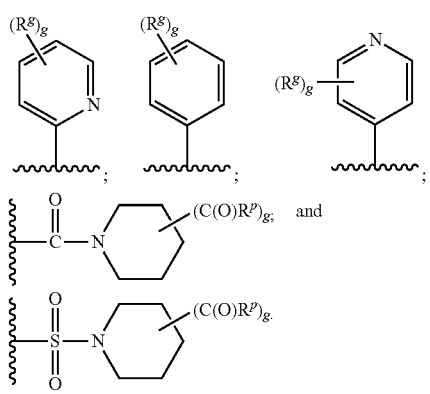

$R^p$ and $Z^2$ are independently selected from O—, OH, a reactive functional group, a component of a reactive functional group or is a linkage fragment covalently binding the compound to a carrier molecule. The index g is an integer selected from 0, 1, 2, 3, 4 and 5 and, when g is two or greater, each $R^g$ or $R^p$ is independently selected. $R^g$ is selected from H, $R^{38}$, $R^{38}Z^3$, $SO_3H$, $COZ^3$, $R^{38}SO_3H$, $CONHR^{38}SO_3H$, $CONHR^{38}COZ^3$, and when g is greater than or equal to 2, each $R^g$, or $R^p$ is independently selected. $Z^3$ is OH, O—, a reactive functional group, a component of a reactive functional group or is a linkage fragment covalently binding the compound to a carrier molecule. $R^{28}$ and $R^{38}$ are independently selected from a bond and a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, $R^{28}$ and $R^{38}$ are independently selected from substituted or unsubstituted alkyl having from 1 to 20 carbon atoms.

A is a heteroaryl moiety. In exemplary embodiments, A is selected from substituted or unsubstituted indole (e.g., indolene, indolinium), substituted or unsubstituted imidazole (e.g., imidazolene, imidazolinium), substituted or unsubstituted thiazole, and substituted or unsubstituted oxazole. At least one of $R^a$, $R^b$, $R^c$, $R^d$, $R^1$, $R^2$, $R^3$, $R^4$, $R^5$ and $R^6$ is a reactive functional group or is a linkage fragment covalently binding said compound to a carrier molecule.

In various embodiments, the compound of the invention comprises at least three $SO_3H$ moieties.

In a further aspect, the invention provides a method of monitoring an enzyme reaction. The method generally comprises providing a reaction mixture comprising the enzyme and at least a first reactant composition. An exemplary reactant composition comprises a compound having a component that reacts with the enzyme, a fluorescent label component, and an adaptor or linker-adaptor component joining the reactant component to the label component. The reaction mixture is then illuminated to excite the fluorescent label component, and a fluorescent signal from the reaction mixture characteristic of the enzyme reaction is detected.

The invention also provides methods of monitoring nucleic acid synthesis reactions. The methods comprise contacting a polymerase/template/primer complex with a nucleotide or nucleotide analog conjugated to a fluorescent cyanine dye of the invention through a linker component. A characteristic signal from the fluorescent dye is then detected that is indicative of incorporation of the nucleotide or nucleotide analog into a primer extension reaction.

In various embodiments, the present invention provides methods of using the compounds described herein for performing nucleic acid analyses, and particularly nucleic acid sequence analyses. In various embodiments, the compounds of the invention are used in single molecule nucleic acid sequencing. Exemplary methods of the invention include using a template nucleic acid complexed with a polymerase enzyme in a template dependent polymerization reaction to produce a nascent nucleic acid strand, contacting the polymerase and template nucleic acid with a compound of the invention, and detecting whether or not the compound or a substructure thereof (e.g., a monophosphate nucleic acid) was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where fluorophores released from incorporated analogs are detected.

The compounds and compositions of the invention are of use in single molecule or single molecule real time DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores to be utilized and distinguished in an assay. Moreover, the fluorophores of the invention are of use in systems utilizing the principles of FRET to transfer energy from a first excited fluorophore to a second fluorophore, causing the second fluorophore to emit. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

Other aspects, embodiments and objects of the present invention will be apparent from the detailed description that follows.

BRIEF DESCRIPTION OF THE DRAWINGS

In FIG. 1, $Z^{10}$ represents, OH, O—, a reactive functional group, a component of a reactive functional group or a linkage fragment covalently binding the compound to a carrier molecule. When a molecule has more than one $Z^{10}$ moiety, each $Z^{10}$ moiety is independently selected from the group above.

DETAILED DESCRIPTION OF THE INVENTION

Introduction

Figure 1A:
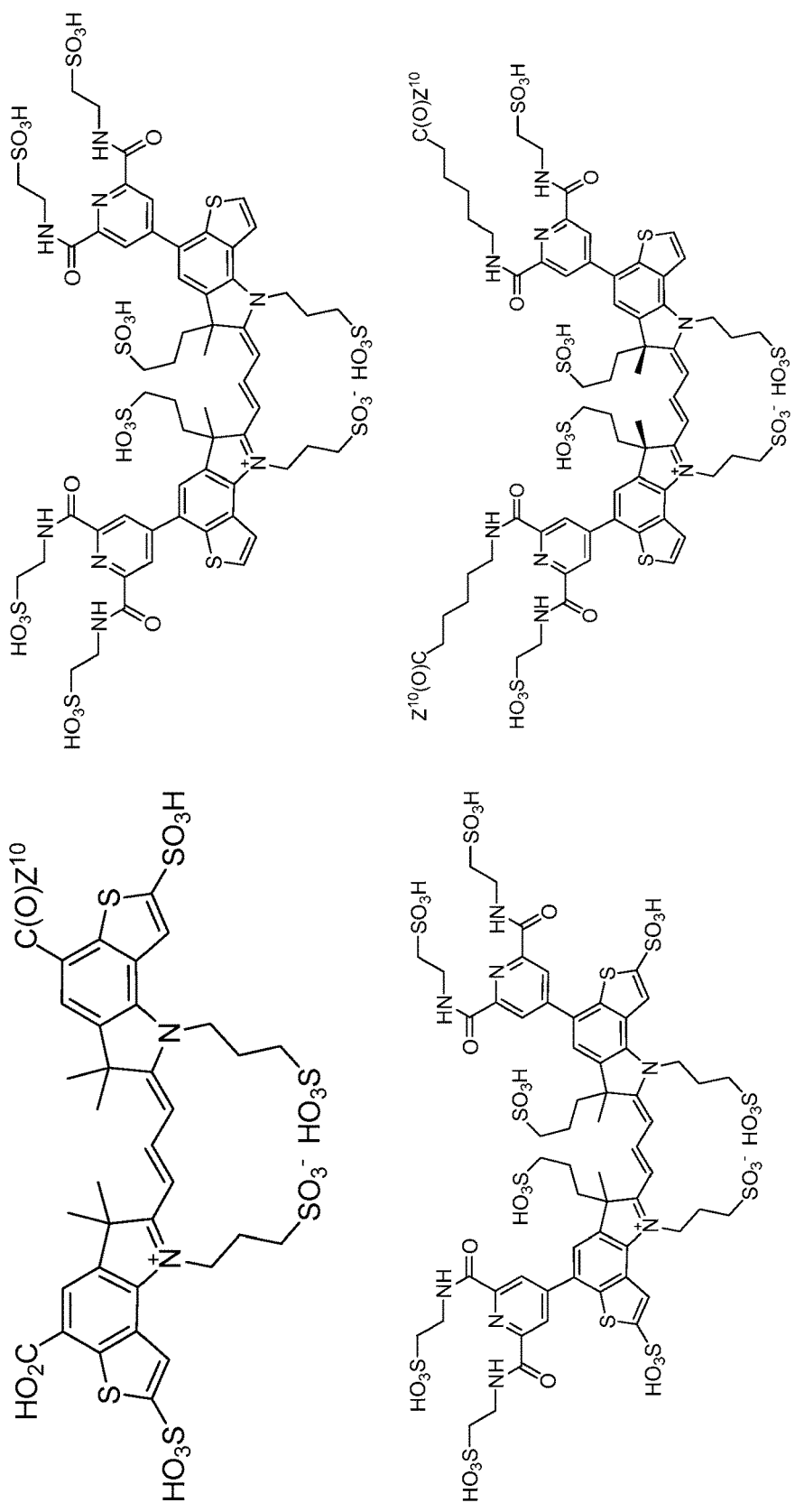
FIG. 1 (A-F) shows exemplary compounds of the invention.

The present invention provides a class of reactive fluorescent compounds based upon the cyanine-dye nucleus functionalized with one or more heteroaryl moieties. Also provided is a wide variety of conjugates of the cyanine dyes with a carrier molecule, e.g., polyphosphate nucleotides, nucleic acids and other carrier molecules, including biological, non-biological and biologically active species. Selected cyanine labels described herein include a reactive functional group or a linker functionalized with a functionalized reactive group that is readily converted into an array of derivatives without requiring a modification of the cyanine nucleus. Accordingly, the compounds of the invention provide an, as yet, undisclosed advantage, allowing facile access to an array of conjugates between the heteroaryl functionalized cyanine nucleus and one or more carrier molecules.

Residing in the field of fluorescent labels, the present invention provides benefits of particular note. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity, high specificity in labeling, and a broader range of excitation/emission spectra. Many fluorescent labels based upon the cyanine-nucleus are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate cyanine-based fluorophore for a particular application and, if it not readily available commercially, will be able to synthesize the necessary fluorophore de novo or synthetically modify commercially available cyanine compounds to arrive at the desired fluorescent label.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following abbreviations and terms will be employed, and are intended to be defined as indicated below.

Abbreviations

"FET", as used herein, refers to "Fluorescence Energy Transfer."

"FRET", as used herein, refers to "Fluorescence (Foerster) Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Any of the dyes set forth herein can be a component of an FET or FRET pair as either the donor or acceptor. Conjugating a compound of the invention and a donor or acceptor fluorophore through reactive functional groups on the conjugation partners and an appropriate linker, adaptor, carrier molecule or a combination thereof is well within the abilities of those of skill in the art.

The symbol "R", as used herein, refers to moiety which is a member selected from the moieties defined in the following section, e.g., substituted or unsubstituted alkyl, substituted or unsubstituted heteroalkyl, substituted or unsubstituted aryl, substituted or unsubstituted heteroaryl, etc. as well as those groups set forth as substituents of these moieties.

Definitions

Where chemical moieties are specified by their conventional chemical formulae, written from left to right, they optionally equally encompass the moiety which would result from writing the structure from right to left, e.g., —CH$_2$O— is intended to also recite —OCH$_2$—; —NHS(O)$_2$— is also intended to optionally represent. —S(O)$_2$HN—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of skill in the art. Similarly, where the salt is disclosed, this structure also discloses the compound in a free acid or free base form. Methods of making salts and free acids and free bases are well-known in the art.

"A component of a reactive functional group" refers to a leaving group or to a component of the reactive functional group that is itself reactive. Exemplary leaving groups include halogens of an acyl or alkyl halide, the alcohol component of an ester (e.g., an active ester, e.g., N-hydroxysuccinimide), an imidazole and the like. An exemplary reactive component of the reactive functional group is an unsaturated bond (e.g., the double bond of a maleimide, or the unsaturated bond of an alkyne). Additional exemplary components include those forming bonds through coupling reactions (e.g., oxidative coupling, e.g., S—S bond formation).

"Cyanine," as used herein, refers to aryl and heteroaryl polymethine dyes such as those based upon the cyanine, merocyanine, styryl and oxonol ring. The cyanine dyes of the invention are represented herein according to convention, shown as consisting of two substituted indole moieties linked by a polymethine group. According to the convention in the art, one of the substituted indole moieties is shown as positively charged with a C—C single bond between the polymethine moiety and one of the two indole moieties; and the other indole moiety is shown as uncharged with a double bond from a carbon of the polymethine moiety and the indole moiety. As those of skill will appreciate this structure is one possible resonance structure of the cyanine backbone. Accordingly, the groups that appear as formally positively charged in the cyanine structures are not named as positively charged species but as their neutral analogues. The formulae for compounds of the invention encompass all resonance forms of these compounds.

As used herein, the term "trimethine" refers to a cyanine dye in which Q is a $C_3$ residue with two double bonds.

"Amino Acid," as used herein refers to the genus encompassing hydrophilic amino acids, acidic amino acids, basic amino acids, polar amino acids, hydrophobic amino acids, aromatic amino acids, non-polar amino acids and aliphatic amino acids, including the genus and the species therein. A "peptide" are formed from such amino acids linked via peptide bonds Amino acids also encompass amino-carboxylic acid species other than α-amino acids, e.g., aminobutyric acid (aba), aminohexanoic acid (aha), aminomethylbenzoic acid (amb) etc. In an exemplary embodiment, the cyanine dye of the invention is conjugated to a carrier molecule through a linker having one or more than one amino acid. Exemplary amino acids of use in such linkers include lysine, proline and acidic amino acids.

An "adaptor" is a moiety that is at least bivalent. Exemplary adaptors are bound to a nucleic acid and a fluorescent dye, either directly or through a linker. The adaptor can also be bound to a second fluorescent dye, to a polyvalent scaffold or to a second nucleic acid. When the adaptor is bound to a second dye, either directly or through a polyvalent scaffold, the resulting conjugate is optionally a FRET pair. The adaptor is preferably bound to the phosphorus atom of a phosphate, phosphate ester or polyphosphate moiety of a nucleic acid. In exemplary embodiments, the adaptor is bound through an amide moiety to the dye or to the linker of the linker-dye cassette. The amide moiety is formed between an amine on the adaptor and a carboxyl group on the dye or the linker precursor. An exemplary adaptor moiety is a piperidinyl moiety, or an amide formed through the amine of a piperidinyl moiety.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation into a compound of the invention. Further modifications include those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids. Exemplary nucleic acids of the invention include one or more dye moiety of the invention bound thereto.

Exemplary modified nucleic acids include, but are not limited to, peptide nucleic acids (PNAs), those with phosphodiester group modifications (e.g., replacement of O⁻ with OR, NR, or SR), 2'-, 3'- and 5'-position sugar modifications, modifications to the nucleobase moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of $P(O)O_3$ with another moiety, methylations, unusual base-pairing combinations such as the isobases, isocytidine and isoguanidine and the like. Nucleic acids can also include non-natural bases, e.g., nitroindole. Non-natural nucleobases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

The nucleic acid can comprise DNA, RNA or chimeric mixtures or derivatives or modified versions thereof. Both the probe and target nucleic acid can be present as a single strand, duplex, triplex, etc. Moreover, as discussed above, the nucleic acid can be modified at the nucleobase moiety, sugar moiety, or phosphate backbone with other groups such as radioactive labels, minor groove binders, intercalating agents, donor and/or acceptor moieties and the like.

The nucleobase represented by "Y" in the formulae herein can be selected from any of the natural or non-natural nucleobases or nucleobase analogs, including e.g., purine or pyrimidine bases that are routinely found in nucleic acids and nucleic acid analogs, including adenine, thymine, guanine, cytidine, uracil, and inosine. The nucleobases in the compounds of the present invention may include the conventional bases described herein or they may include such bases substituted at one or more side groups, or other analogs, such as 1, N-6-ethenoadenosine or pyrrolo C, in which an additional ring structure renders the nucleobase neither a purine nor a pyrimidine. The nucleobase can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, nitroindole, and 2,6-diaminopurine. The dye of the invention or another probe component can be attached to the modified base.

In another embodiment, the nucleic acid comprises at least one modified sugar moiety selected from the group including, but not limited to, arabinose, 2-fluoroarabinose, xylulose, and hexose. The dye or another probe component can be attached to the modified sugar moiety.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The dye or another probe component can be attached to the modified phosphate backbone.

"Nucleic acid" also includes a component of a conjugate with one or more modified phosphate bridges (e.g., $P(O)O_3$) by conjugating a linker-dye conjugate of the invention to the nucleic acid, e.g., replacing or derivatizing an oxygen of the bridge) with a compound of the invention or a species that includes a compound of the invention attached to an adaptor. For example, "nucleic acid" also refers to species in which, rather than the $P(O)(O^-)O_2$ moiety of a naturally occurring nucleic acid, includes the moiety ROP(O)(O—)O, in which R is a dye-linker conjugate of the invention, an adaptor, a linker-adaptor cassette or a fluorescent dye-linker-adaptor cassette. An exemplary linker is an amino acid or peptide linker of the invention. In various embodiments, one oxygen of this structure is bound to the phosphorus atom of a $P(O)(O^-)O_2$ moiety, such that the nucleic acid includes two or more phosphate moieties bound to each other.

Further exemplary nucleic acids of the invention include a nucleotide having a polyphosphate moiety, e.g., pyrophosphate or a higher homologue, such as the 3-mer, 4-mer, 5-mer, 6-mer, 7-mer, 8-mer and the like. Exemplary nucleic acids include such a polyphosphate moiety bonded to the 5'-oxygen of a nucleoside. In addition to the attached polyphosphate moiety can include a modified phosphate bridge, such as those exemplified herein. In an exemplary embodiment, the modified phosphate bridge is modified with an adaptor, a linker dye conjugate, a linker-adaptor cassette or a fluorescent dye-linker-adaptor cassette. In an exemplary embodiment, the linker is an amino acid or peptide linker such as those set forth herein. Examples of some nucleic acids finding use in the present invention are set forth in Published U.S. Patent Application Nos. 2003/0124576 and 2007/0072196 as well as U.S. Pat. Nos. 7,223,541 and 7,052,839, the full disclosures of which are incorporated herein by reference for all purposes.

Furthermore, "nucleic acid" includes those species in which one or more internucleotide bridge does not include phosphorus: the bridge being optionally modified with a compound of the invention or a linker-dye construct of the invention. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a linker-dye construct of the invention. The discussion above is not limited to moieties that include a carbon atom as the point of attachment; the locus can also be another appropriate linking atom, such as nitrogen or another atom.

Phosphodiester linked nucleic acids of the invention can be synthesized by standard methods known in the art, e.g. by use of an automated DNA synthesizer using commercially available amidite chemistries (Ozaki et al., *Nucleic Acids Research*, 20: 5205-5214 (1992); Agrawal et al., *Nucleic Acids Research*, 18: 5419-5423 (1990); Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

As used herein, "quenching group" refers to any fluorescence-modifying group of the invention that can attenuate, at least partly, the energy (e.g., light) emitted by a fluorescent dye. This attenuation is referred to herein as "quenching". Hence, irradiation of the fluorescent dye in the presence of the quenching group leads to an emission signal from the fluorescent dye that is less intense than expected, or even completely absent. Quenching typically occurs through energy transfer between the fluorescent dye and the quenching group.

"Carrier molecule," as used herein refers to any molecule to which a compound of the invention, or a conjugate incorporating a compound of the invention, is attached. Representative carrier molecules include a nucleic acid, protein (e.g., enzyme, antibody), glycoprotein, peptide, saccharide (e.g., mono-, oligo-, and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism. An exemplary carrier molecule of use in the present invention is a polyphosphate nucleic acid. Exemplary conjugates between a fluorescent dye and a polyphosphate nucleic acid are conjugated by covalent binding of the dye to the linker and hence to the nucleic acid, or covalent binding of the dye to a linker and the linker to the adaptor—the adaptor is conjugated to the nucleic acid. Alternatively, the dye is bound to a linker, which is bound to an adaptor, which is bound to the nucleic acid. In an exemplary embodiment, the adaptor is bound to the polyphosphate moiety through a phosphodiester bond. In an exemplary embodiment, the adaptor (or linker) is attached to the dye through a bond formed with an activated derivative of a carboxyl moiety on the dye. In various embodiments, the bond is an amide bond.

"Activated derivatives of carboxyl moieties," and equivalent species, refers to moiety on a precursor component of a conjugate of the invention (e.g., dye, adaptor, linker, polyvalent moiety) having a leaving group, e.g., an active ester, acyl halide, acyl imidazole, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, optionally, those derivatives of alkyl defined in more detail below, such as "alkenyl", "alkynyl", "alkyldiyl", "alkyleno" and "heteroalkyl."

"Alkenyl", refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc., and the like. In exemplary embodiments, the alkenyl group is ($C_2$-$C_6$) alkenyl.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc., and the like. In exemplary embodiments, the alkynyl group is ($C_2$-$C_6$) alkynyl.

"Alkyldiyl", refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_2$-$C_6$) alkyldiyl. Also preferred are saturated acyclic alkanyldiyl radicals in which the radical centers are at the terminal carbons, e.g., methandiyl (methano); ethan-1,2-diyl(ethano); propan-1,3-diyl(propano); butan-1,4-diyl(butano), and the like (also referred to as alkylenos, defined infra).

"Alkyleno", refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc., and the like. Where specific levels of saturation are intended, the nomenclature alkano, alkeno and/or alkyno is used. In preferred embodiments, the alkyleno group is ($C_2$-$C_6$) alkyleno.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl and, optionally, heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', SO$_3$R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', SO$_3$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl.

The substituents set forth in the two paragraphs above are referred to herein as "aryl group substituents."

Exemplary heteroaryl moieties of use in the present invention include, without limitation:

"Indole", which as used herein refers to an aromatic bicyclic heterocyclic organic compound. The parent structure includes a bicyclic structure, consisting of a six-membered benzene ring fused to a five-membered nitrogen-containing pyrrole ring. "Indole" as used herein refers to both the parent compound and substituted analogs thereof. The substitutions can include fused rings, which are substituted or unsubstituted cycloalkyl, substituted or unsubstituted aryl, substituted or unsubstituted heteroaryl or substituted or unsubstituted heterocycloalkyl. An exemplary fused ring system is a benzo fused ring. "Indole" encompasses positively charged and neutral analogs of the relevant heterocycle. As those of skill will appreciate, since the subject of the invention is cyanine dyes, "Indole-like" fragments, which are not formally "indole" (e.g., gem dimethyl substituents preclude a double bond at a particular position) are encompassed within this definition. Examples of such "indole-like" fragments include "indolene" and "indolinium";

"Imidazole", which as used herein refers to an aromatic five-member heterocyclic compound. The parent structure is a monocyclic ring system with the formula (CH)$_2$N(NH)CH. "Imidazole" as used herein refers to both the parent compound and substituted analogs thereof. The substitutions can include fused rings, which are substituted or unsubstituted cycloalkyl, substituted or unsubstituted aryl, substituted or unsubstituted heteroaryl or substituted or unsubstituted heterocycloalkyl. An exemplary fused ring system is a benzo fused ring. "Imidazole" encompasses positively charged and neutral analogs of the relevant heterocycle. As those of skill will appreciate, since the subject of the invention is cyanine dyes, "Imidazole-like" fragments, which are not formally "imidazole" (e.g., gem dimethyl substituents preclude a double bond at a particular position) are encompassed within this definition. Examples of such "imidazole-like" fragments include "imidazolene" and "imidazolinium";

"Thiazole", as used herein refers to an aromatic five-member heterocyclic compound that contains both sulfur and nitrogen. The parent structure is a monocyclic ring system with the formula $C_3H_3NS$. "Thiazole" as used herein refers to both the parent compound and substituted analogs thereof. The substitutions can include fused rings, which are substituted or unsubstituted cycloalkyl, substituted or unsubstituted aryl, substituted or unsubstituted heteroaryl or substituted or unsubstituted heterocycloalkyl. An exemplary fused ring system is a benzo fused ring;

"Oxazole", as used herein refers to an aromatic five-member heterocyclic compound that contains both oxygen and nitrogen. The parent structure is a monocyclic ring system with the formula $C_3H_3NO$. "Oxazole" as used herein refers to both the parent compound and substituted analogs thereof. The substitutions can include fused rings, which are substituted or unsubstituted cycloalkyl, substituted or unsubstituted aryl, substituted or unsubstituted heteroaryl or substituted or unsubstituted heterocycloalkyl. An exemplary fused ring system is a benzo fused ring.

A "linkage fragment" is a bond, or is a group that is formed by reaction of two reactive functional groups of complementary reactivity. An exemplary linkage fragment is an amide formed by the reaction of an amine and an activated derivative of a carboxylic acid (e.g., acyl halide, acyl imidazole, active ester, etc.). When the cyanine dyes of the invention are conjugated to a carrier molecule, they can be conjugated directly through a linkage fragment or through a linker that includes one or more linkage fragment. For example, a conjugate in which the dye is bound to a carrier molecule through a linker optionally includes a linkage fragment joining the linker and the dye and/or joining the linker and the carrier molecule.

The term "Linker" or "L", as used herein, refers to a single covalent bond or a series of stable covalent bonds incorporating 1-40, e.g., 10-30 nonhydrogen atoms selected from the group consisting of C, N, O, S and P that covalently attach the fluorogenic or fluorescent compounds to another moiety such as a chemically reactive group or a biological or non-biological component, e.g., a carrier molecule. Exemplary linkers include one or more linkage fragment, e.g., —C(O)NH—, —C(O)O—, —NH—, —S—, —O—, joining the dye to the linker and/or the linker to the carrier molecule and the like. Linkers are also of use to join the cyanine nucleus component of the compound to a reactive functional group, or a component of a reactive functional group.

"Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as $\beta_2$-microglobulin ($\beta_2$ m), ferritin and the like; various hormones such as estradiol ($E_2$), estriol ($E_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, enzymes (e.g., a DNA polymerase) diluents, buffers, detergents, and contaminating species, debris and the like that are found mixed with the target.

"Readlength" is the number of bases the DNA polymerase enzyme at the bottom of the ZMW goes through during sequencing. A longer readlength is desirable. Readlength depends, inter alia, on how fast the enzyme can incorporate fluorescent nucleotides of different colors (monitored this by observing pulse widths and interpulse distances). Readlength also depends on how long the enzyme can incorporate analog without being photodamaged (damaged via undesired interactions with fluorescent nucleotides excited by light).

"Accuracy" is how precise a nucleotide with a base of a particular type can be identified as the polymerase enzyme goes through incorporation of fluorescent nucleotides. The base is identified by a pulse of a selected wavelength upon incorporation of the nucleotide incorporating that base. Robust applications include precise base calling. Accuracy can be diminished by one or more of extra pulses, missing pulses and miscalled pulses.

"Extra pulses" refers to a situation in which, a pulse is called and there is no nucleotide incorporation event. Extra pulses may be caused by branching (when enzyme samples the fluorescent analog but does not incorporate), sticks (non-specific interactions of fluorescent nucleotides with enzyme outside of incorporating site and surface of ZMW), photophysical blinking (photophysically unstable behavior of fluorescent nucleotides during incorporation resulting in splitting of fluorescent signal).

"Missing pulses"—when a pulse is not called when there is in fact a nucleotided incorporation event. Missing pulses may be caused by insufficient brightness of fluorescent nucleotides, low purity of fluorescent nucleotides, or polymerase going too fast to detect all pulses.

"Miscalled pulses" refers to a situation in which a pulse of a different kind is called instead of correct one. Miscalls may be caused by insufficient spectral separation between fluorescent nucleotides of different colors, photophysical instability of our fluorescent nucleotides, low intensity or high background of fluorescent nucleotide signal.

THE EMBODIMENTS

In an exemplary embodiment, the present invention provides a fluorescent compound having the formula:

A-Q-B wherein the symbol Q represents a moiety with a formula which is a member selected from:

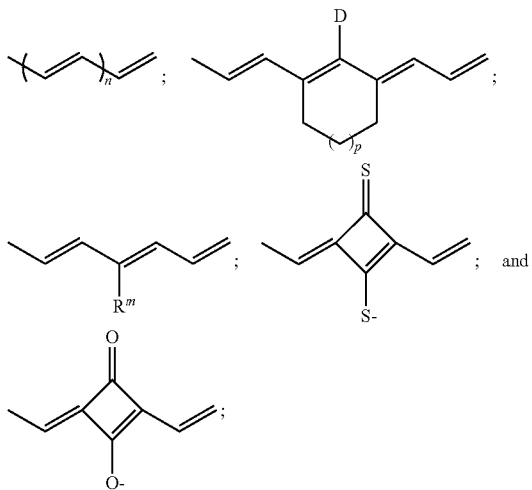

The symbol D represents a member selected from H, halogen, $OR^a$, $SR^a$, $NR^aR^b$, $CR^aR^bR^c$,

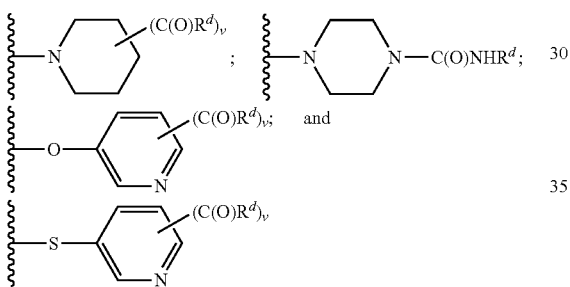

in which $R^a$, $R^b$, $R^c$ and $R^d$ are members independently selected from H, $R^8$, $R^8Z^o$, $SO_3H$, $COZ^o$, $R^8SO_3H$, $R^8C(O)Z^o$,

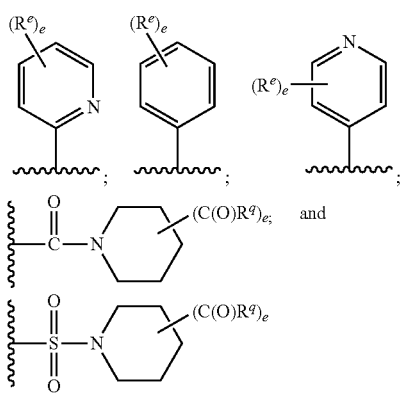

wherein $Z^o$ and $R^q$ are independently selected from a OH, O—, a reactive functional group, a component of a reactive functional group and a linkage fragment covalently binding said compound to a carrier molecule. The index v is 0, 1, 2, 3, 4 or 5 and, when v is two or greater, each $R^d$ is independently selected. $R^c$ is selected from H, $R^{18}$, $R^{18}Z^1$, $SO_3H$, $C(O)Z^1$, $R^{18}C(O)Z^1$, $R^{18}SO_3H$, $SO_3H$, $CONHR^{18}SO_3H$, and $CONHR^{18}C(O)Z^1$. The index e is 0, 1, 2, 3, 4, or 5 and, when e is 2 or greater, each $R^q$ is independently selected. $R^8$ and $R^{18}$ are independently selected from a bond and a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, $R^8$ and $R^{18}$ are independently selected from substituted or unsubstituted alkyl having from 1 to 20 carbon atoms. $Z^1$ is OH, O—, a reactive functional group, a component of a reactive functional group or a linkage fragment covalently binding the compound to a carrier molecule. The index n is 1, 2 or 3. The index p is 0, 1 or 2.

$R^m$ is a member selected from:

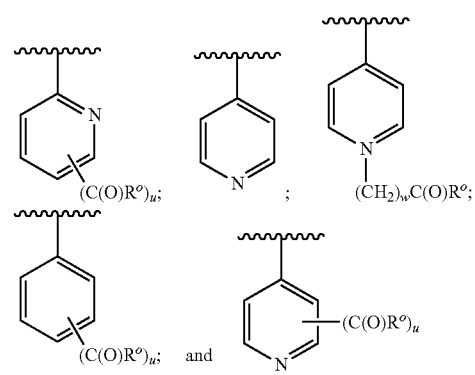

The index w is an integer from 1 to 10. $R^o$ is OH, O—, a reactive functional group, a component of a reactive functional group or is a linkage fragment covalently binding the compound to a carrier molecule. The index u is 0, 1, 2, 3, 4 or 5 and, when u is 2 or greater, each $R^o$ is independently selected.

In an exemplary embodiment, B is a moiety with a formula selected from:

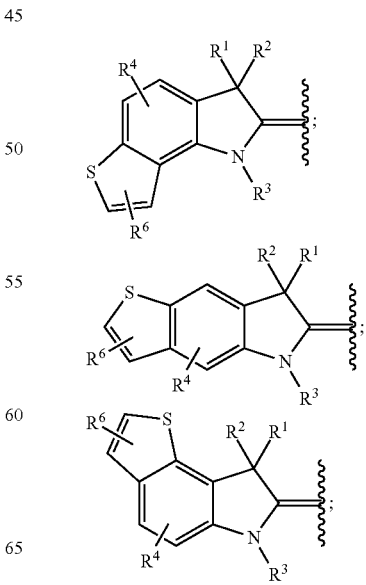

-continued

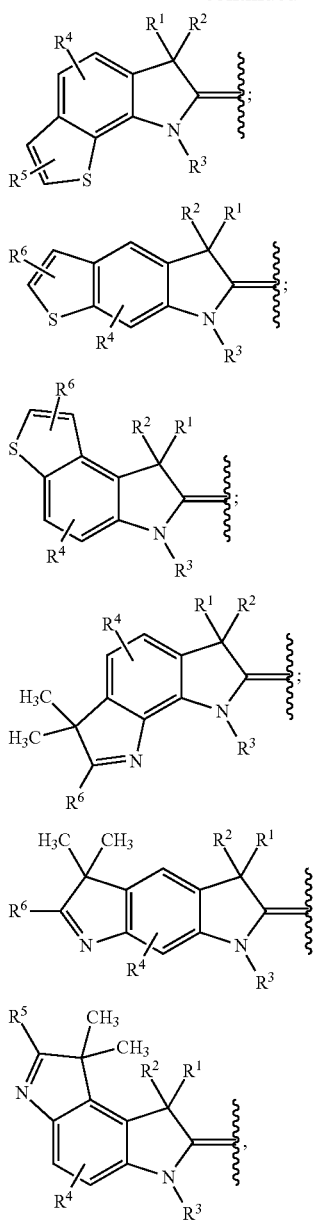

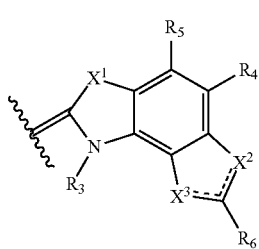

wherein, when the compound includes more than one $R^4$ and/or more than one $R^6$, each $R^4$ and/or $R^6$ moiety is independently selected.

In various embodiments, B is a moiety which is a member selected from Formulae I, II and III:

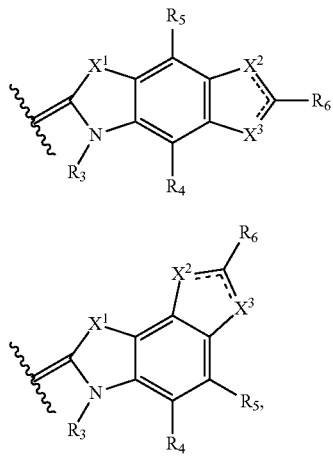

(I)

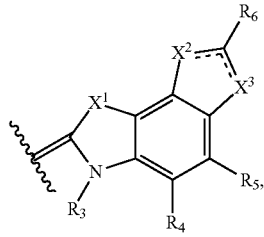

(II)

(III)

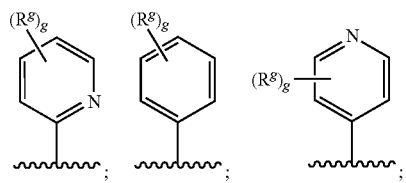

In the formulae for B above, $X^1$ is a member selected from $CR^1R^2$, O, S and $NR^1$. $R^1$, $R^2$ and $R^3$ are independently $CH_2R^7$. $X^2$ and $X^3$ are members independently selected from O, S, N, NH, $CR^{22}$, and $CR^{22}R^{23}$. $R^4$, $R^5$, $R^6$, $R^7$, $R^{22}$ and $R^{23}$ are members independently selected from H, $R^{28}$, $R^{28}Z^2$, $SO_3H$, $CO(Z)^2$, $R^{28}SO_3H$, $C(O)NHR^{28}SO_3H$, $CONHR^{28}C(O)Z^2$,

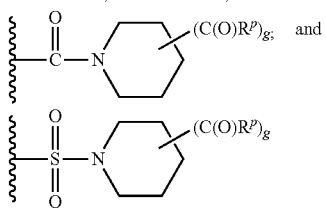

wherein $R^p$ and $Z^2$ are independently selected from OH, H, a reactive functional group, a component of a reactive functional group and a linkage fragment covalently binding said compound to a carrier molecule. $R^{28}$ is a bond or is a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, $R^{28}$ and $R^{38}$ are independently selected from a bond or a member selected from substituted or unsubstituted alkyl having from 1 to 20 carbon atoms.

The index g is an integer selected from 0, 1, 2, 3, 4 and 5 and when g is greater than or equal to 2, each $R^g$ is independently selected. $R^g$ is a member selected from H, $R^{38}$, $R^{38}Z^3$, $SO_3H$, $CO_2H$, $R^{38}SO_3H$, $CONHR^{38}SO_3H$, $CONHR^{38}C(O)Z^3$. $R^{38}$ is a bond or is a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl.

$Z^2$ and $Z^3$ are independently selected from OH, O—, a reactive functional group, a component of a reactive functional group or is a linkage fragment covalently binding the compound to a carrier molecule.

In various embodiments, $R^g$ has the formula:

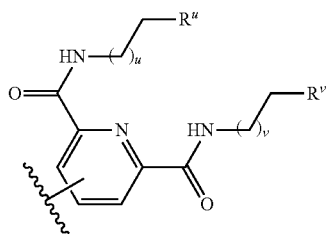

in which the indeces u and v are independently selected from the integers 0, 1, 2, 3, 4, 5, 6, 7, 8, 9 and 10. The symbols $R^u$ and $R^v$ are independently selected from $COZ^4$ and $SO_3H$, in which $Z^4$ is OH, O—, a component of a reactive functional group, a reactive functional group or a linkage fragment covalently binding the compound to a carrier molecule.

In various embodiments, $R^g$ has the formula:

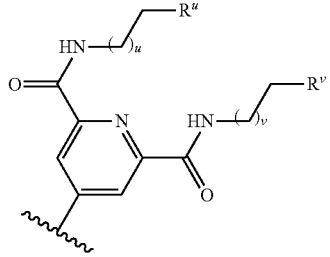

in which the indeces u and v, and the radicals $R^u$ and $R^v$ are as set forth above.

In an exemplary embodiment, $R^g$ has the formula:

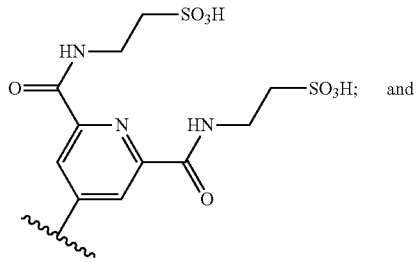

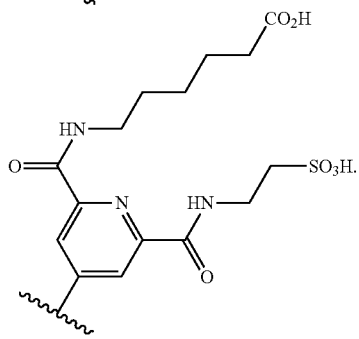

In an exemplary embodiment, D has a formula selected from:

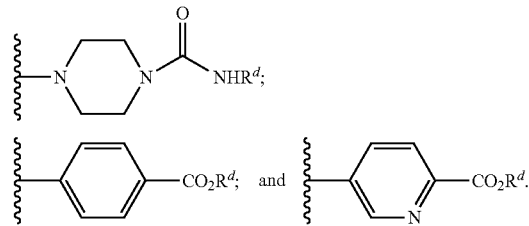

In an exemplary embodiment, $R^a$, $R^b$, $R^c$ and $R^d$ are selected from:

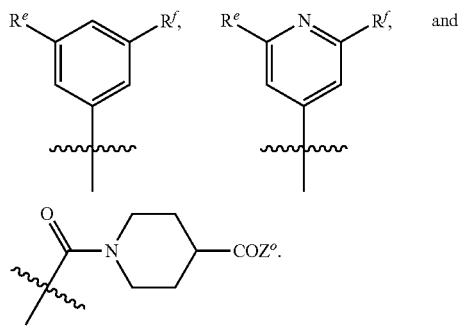

In an exemplary embodiment, $R^e$ and $R^f$ are independently selected from the groups set forth above for $R^e$.

In an exemplary embodiment, $R^4$, $R^5$, $R^6$, $R^7$, $R^{22}$ and $R^{23}$ are independently selected from:

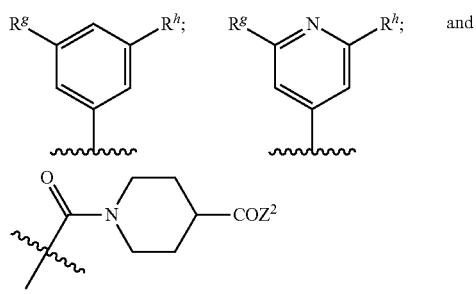

In an exemplary embodiment, $R^g$ and $R^h$ are independently selected from the groups set forth above for $R^g$.

In an exemplary embodiment, $R^m$ has a formula selected from:

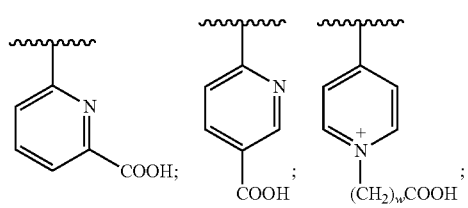

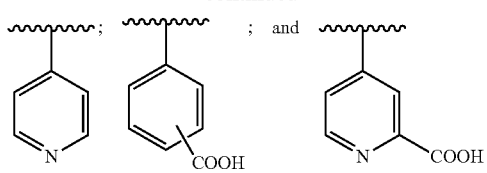

In an exemplary embodiment, at least one, at least two, at least three or at least four of $R^a$, $R^b$, $R^c$, $R^d$, $R^1$, $R^2$, $R^3$, $R^4$, $R^5$ and $R^6$ comprises a reactive functional group or a component of a reactive functional group, is a reactive functional group or is a linkage fragment covalently binding the compound to a carrier molecule. In various embodiments, the compound of the invention comprises at least three $SO_3H$ moieties.

A is a heteroaryl moiety. Exemplary A moieties include substituted or unsubstituted indole, substituted or unsubstituted imidazole, substituted or unsubstituted thiazole, and substituted or unsubstituted oxazole.

In various embodiments A is a substituted or unsubstituted indole moiety. Various indole moieties of use in the compounds of the invention include, but are not limited to:

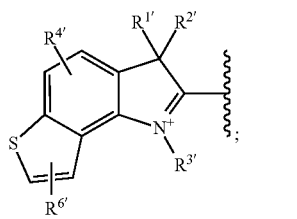

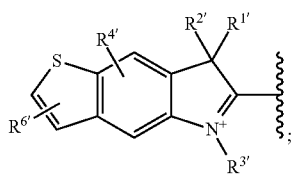

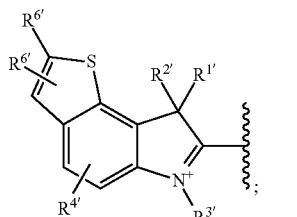

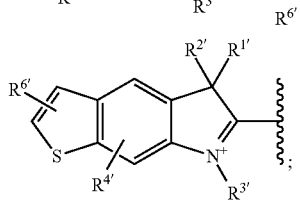

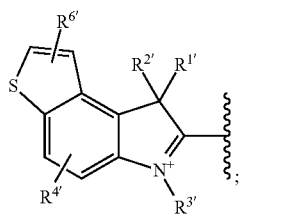

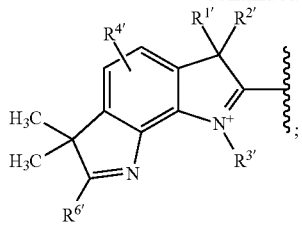

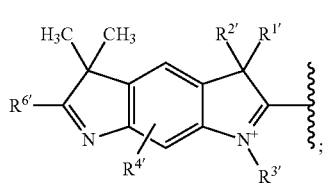

and

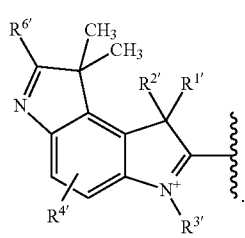

in which $X^{1'}$ is a member selected from $CR^{1'}R^{2'}$, O, S and $NR^{1'}$. $R^{1'}$, $R^{2'}$ and $R^{3'}$ are independently $CH_2R^{7'}$. $X^{2'}$ and $X^{3'}$ are members independently selected from O, S, N, NH, $CR^{22'}$, and $CR^{22'}R^{23'}$. $R^{4'}$, $R^{5'}$, $R^{6'}$, $R^{7'}$, $R^{22'}$ and $R^{23'}$ are members independently selected from H, $R^{28'}$, $R^{28'}Z^{2'}$, $SO_3H$, $COZ^{2'}$, $R^{28'}SO_3H$, $CONHR^{28'}SO_3H$, and $CONHR^{28'}COZ^{2'}$.

In various embodiments, the compounds include more than one $R^{4'}$ and/or $R^{6'}$ and each $R^{4'}$ and $R^{6'}$ are independently selected.

In exemplary embodiments, the A moieties according to the above formulae have a formula selected from the group:

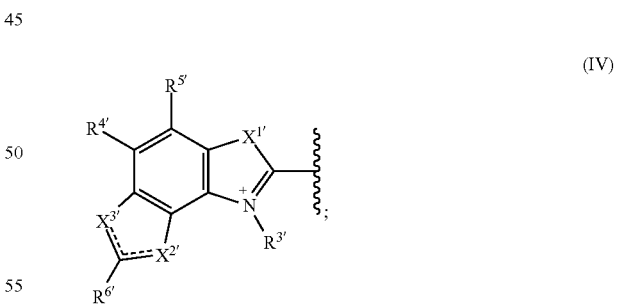

(IV)

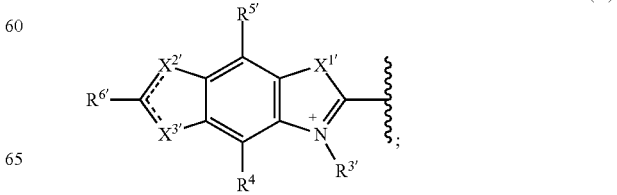

(V)

-continued

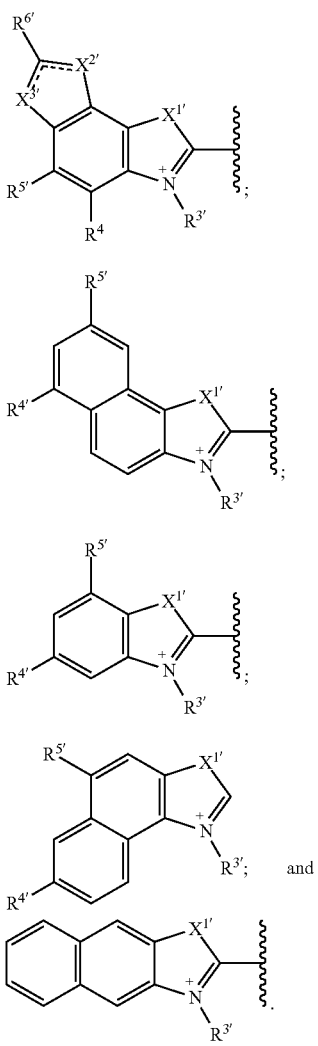

In an exemplary embodiment, $R^{4'}$, $R^{5'}$, $R^{6'}$, $R^{22'}$ and $R^{23'}$ are members independently selected from:

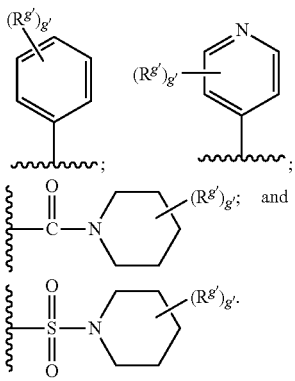

The index g' is selected from 0, 1, 2, 3 and 4, and when it is greater than or equal to 2, each $R^{g'}$ is independently selected from the groups set forth above for $R^g$.

In various embodiments, $R^{4'}$, $R^{5'}$, $R^{6'}$, $R^{7'}$, $R^{22'}$ and $R^{23'}$ are members independently selected from:

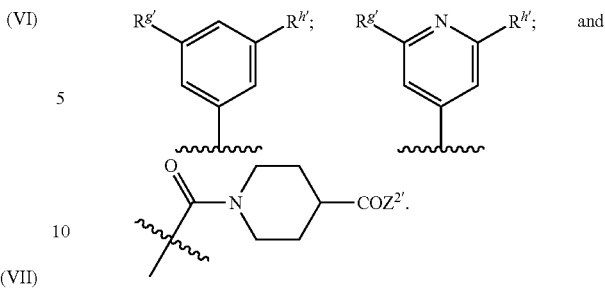

$Z^{2'}$ is OH, O—, a reactive functional group or is a linkage fragment covalently binding said compound to a carrier molecule. $R^{g'}$ and $R^{h'}$ are members independently selected from H, $R^{38'}$, $R^{38'}Z^{3'}$, $SO_3H$, $CO_2H$, $R^{38'}SO_3H$, $CONHR^{38'}SO_3H$, $CONHR^{38'}CO_2H$. $Z^{3'}$ is OH, O—, a reactive functional group or is a linkage fragment covalently binding said compound to a carrier molecule. $R^{28'}$ and $R^{38'}$ are selected from a bond and a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, $R^{28'}$ and $R^{38'}$ are independently selected from substituted or unsubstituted alkyl having from 1 to 20 carbon atoms.

In various embodiments, $R^{g'}$ and $R^{h'}$ are independently selected from moieties of the formula:

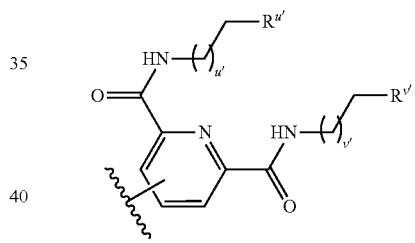

in which the indeces u' and v' are independently selected from the integers 0, 1, 2, 3, 4, 5, 6, 7, 8, 9 and 10. The symbols $R^{u'}$ and $R^{v'}$ are independently selected from $COZ^{4'}$ and $SO_3H$, in which $Z^{4'}$ is OH, O—, a component of a reactive functional group, a reactive functional group or a linkage fragment covalently binding the compound to a carrier molecule.

In various embodiments, $R^{g'}$ and $R^{h'}$ are independently selected moieties of the formula:

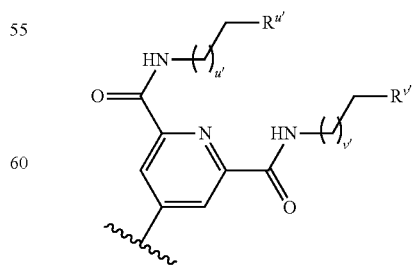

in which the indeces u' and v', and the radicals $R^{u'}$ and $R^{v'}$ are as set forth above.

In an exemplary embodiment, $R^{g'}$ and $R^{h'}$ are independently selected from the moieties:

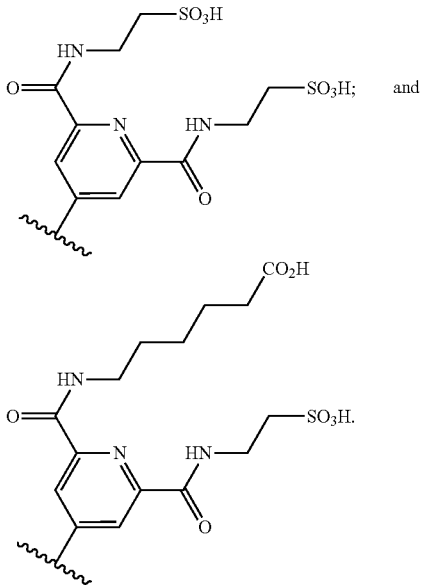

In an exemplary embodiment, at least one, at least two, at least three or at least four of $R^{1'}$, $R^{2'}$, $R^{3'}$, $R^{4'}$, $R^{5'}$ and $R^{6'}$ includes a reactive functional group, is a reactive functional group, a component of a reactive functional group or is a linkage fragment covalently binding said compound to a carrier molecule. In various embodiments, the compound of the invention comprises at least three $SO_3H$ moieties.

The invention provides cyanines including various heterocyclic moieties within their framework. For example, in various embodiments, $X^2$, $X^{2'}$, $X^3$ and $X^{3'}$ are members independently selected from O, S, N, NH, or from CH, $CH_2$ and $C(CH_3)_2$. In an exemplary embodiment, the invention provides compounds in which at least one member selected from $X^2$, $X^{2'}$, $X^3$ and $X^{3'}$ is selected from NH, O and S.

In various embodiments, compounds of the invention include at least 1 sulfur atom. In exemplary compounds, at least one of $X^2$, $X^{2'}$, $X^3$ and $X^{3'}$ is S. In an exemplary embodiment at least two of these moieties, three of these moieties or four of these moieties is S.

The invention provides compounds containing oxygen heterocyclic substructures. For example. In various embodiments, at least one of $X^2$, $X^{2'}$, $X^3$ and $X^{3'}$ is O. In exemplary embodiments, not more than one member selected from $X^2$, $X^{2'}$, $X^3$ and $X^{3'}$ is O. Also provided are compounds that do not include an oxygen heterocyclic substructure, i.e., none of $X^2$, $X^{2'}$, $X^3$ and $X^{3'}$ is O.

In addition to including heteroatoms, the moieties $X^2$ and $X^{2'}$ are independently carbon-containing moieties, thus, in various embodiments, the invention provides compounds in which at least one of $X^2$ and $X^{2'}$ is CH, $CH_2$ or $C(CH_3)_2$.

The invention provides compounds that are substituted with one or more sulfonate/sulfonic acid/sulfonamide moiety, which may be attached directly to a cyclic component of the cyanine nucleus or it can be attached through a linker, such as an alkyl linker. For example, the invention provides compounds in which at least one of $R^6$ and $R^{6'}$ is $SO_3^-$ or $S(O)_2NHR^{80}Z^{14}$, in which $R^{80}$ is substituted or unsubstituted alkyl or substituted or unsubstituted heteroalkyl and $Z^{14}$ is a reactive group or a linkage fragment covalently binding the compound to a carrier molecule.

The invention provides cyanines in which $R^a$, $R^b$, $R^c$ and $R^d$ are members independently selected from H, a bond or is a member selected from substituted or unsubstituted substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment, one or more of these moieties is substituted or unsubstituted alkyl having from 1 to 20 carbon atoms.

Exemplary compounds of the invention have a formula which is a member selected from:

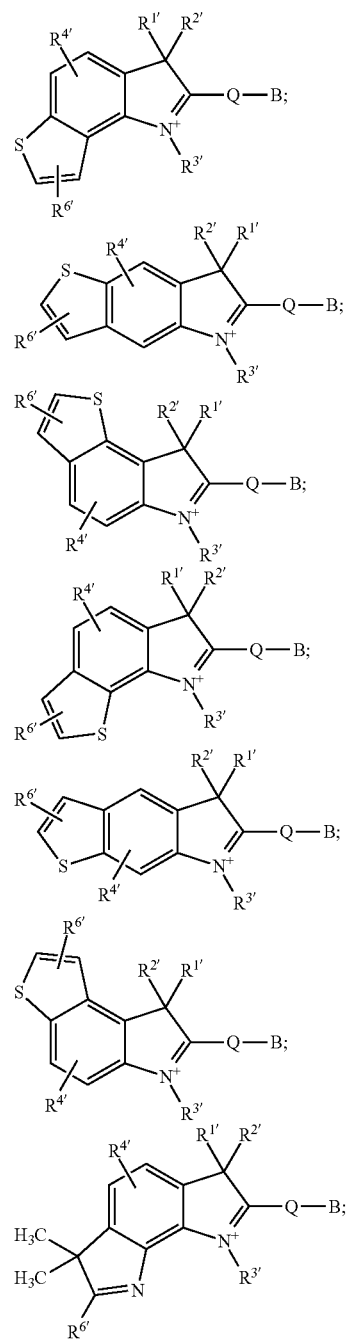

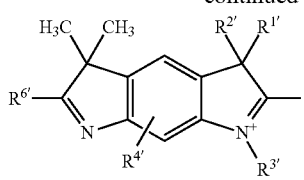
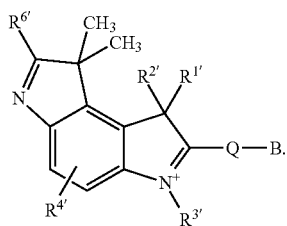
In the formulae above, there may be more than one R⁴' and/or more than one R⁶'. When there is more than one R⁴' and/or more than one R⁶', each R⁴' and R⁶' is independently selected.
Exemplary compounds of the invention according to the formulae above include:
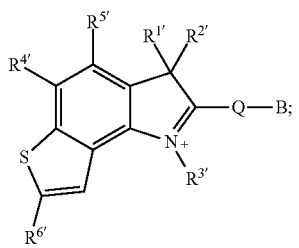
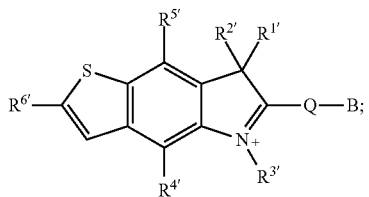
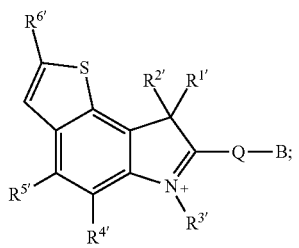
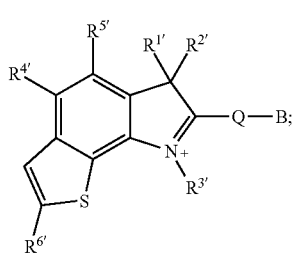
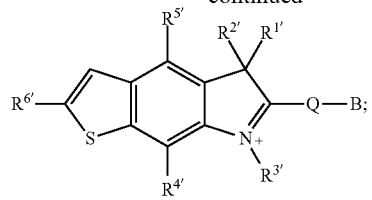
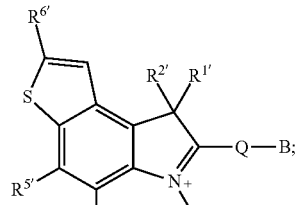
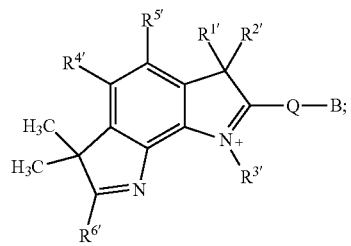
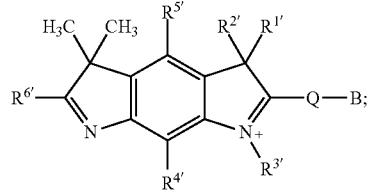
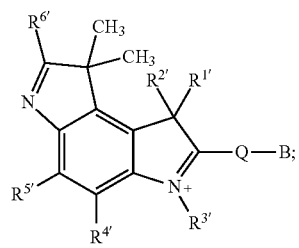
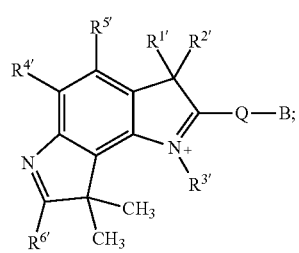
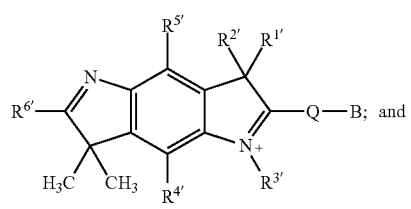

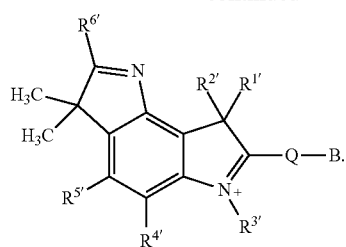
Exemplary compounds of the invention include:
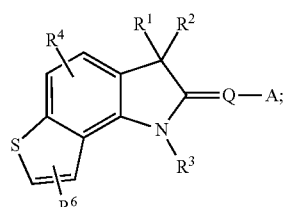
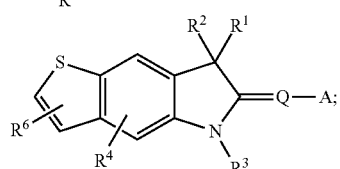
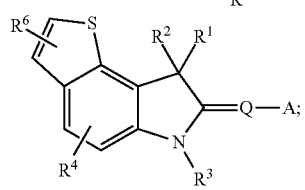
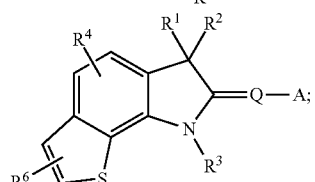
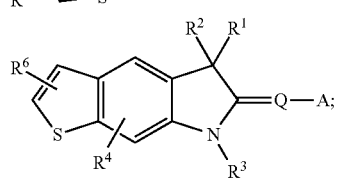
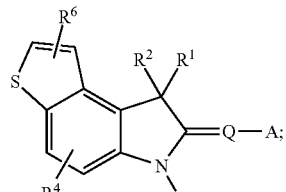
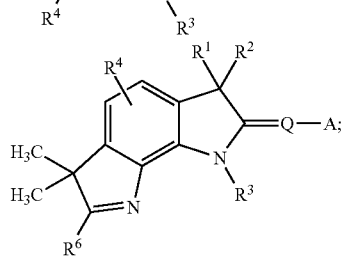
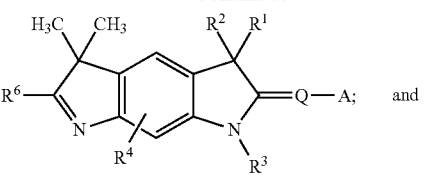
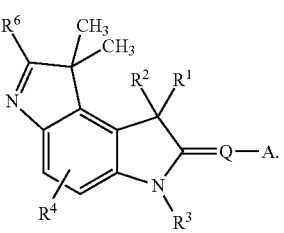
In the formulae above, there may be more than one $R^4$ and/or more than one $R^6$. When there is more than one $R^4$ and/or more than one $R^6$, each $R^4$ and $R^6$ is independently selected.
Exemplary compounds of the invention according to the formulae above include:
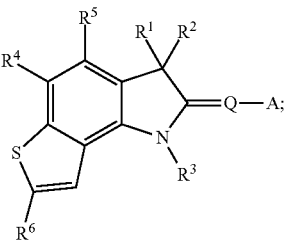
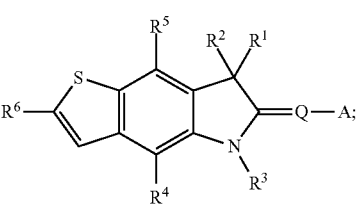
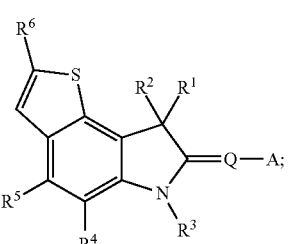
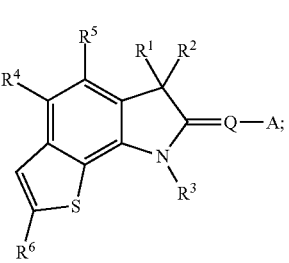

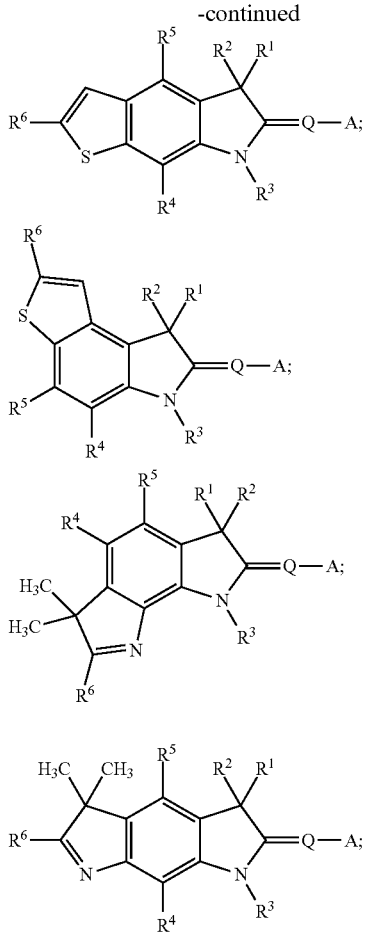
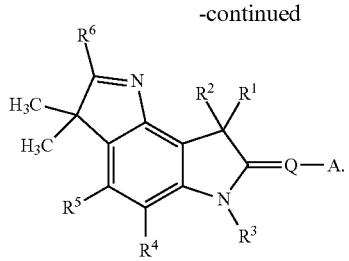
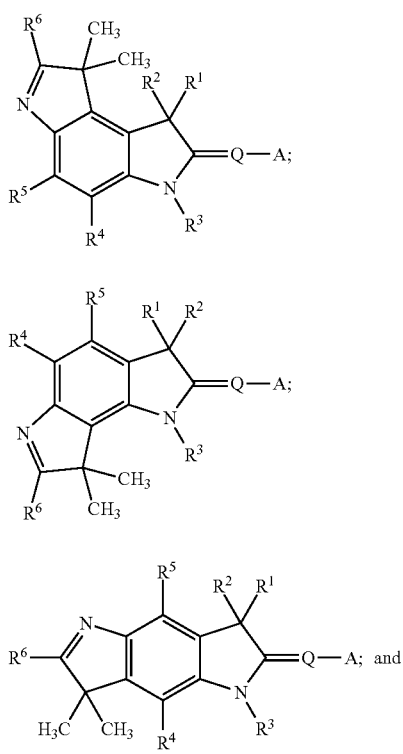
Further exemplary compounds of the invention include:
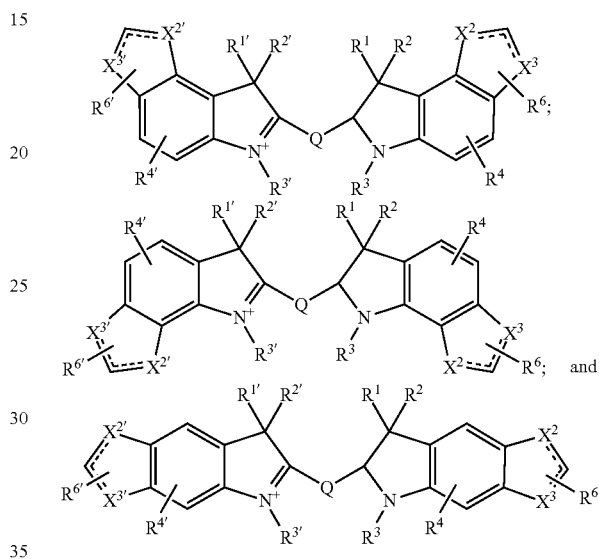
wherein, each $R^4$, $R^{4'}$ $R^6$ or $R^{6'}$ moiety is independently selected and when said compound includes more than one $R^4$, $R^{4'}$ $R^6$ or $R^{6'}$ moiety, each $R^4$, $R^{4'}$ $R^6$ or $R^{6'}$ moiety is independently selected.
Further exemplary compounds of the invention include:
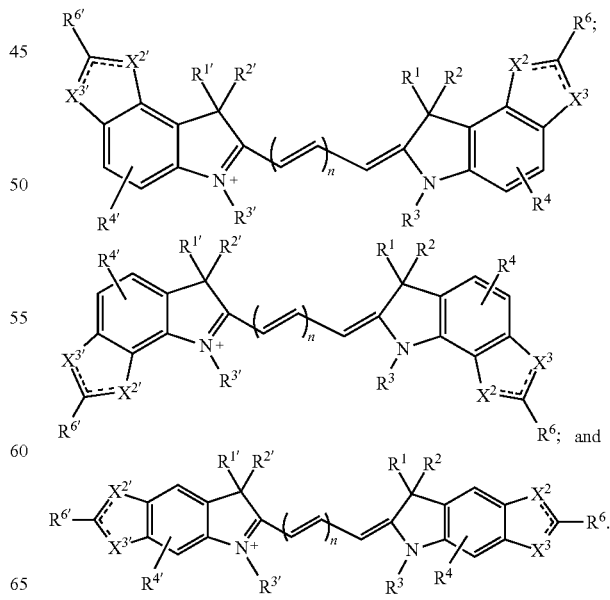

In the formulae above, there may be more than one $R^4$ and/or $R^{4'}$. When there is more than one $R^4$ and/or $R^{4'}$, each $R^4$ and $R^{4'}$ is independently selected.
Exemplary compounds of the invention include:
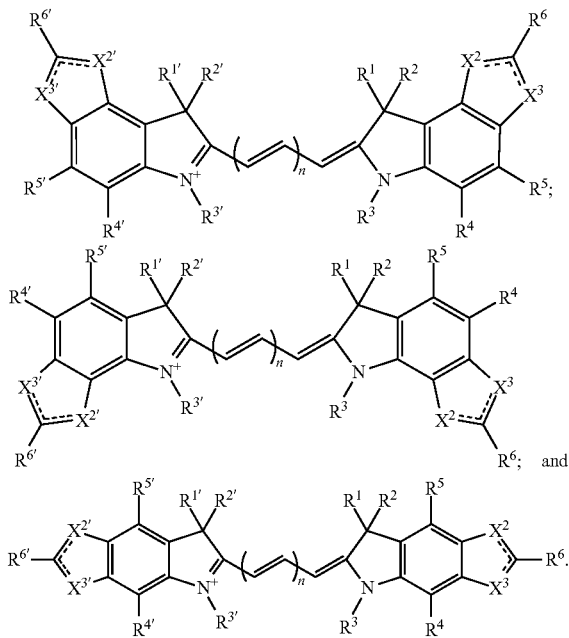
Further exemplary compounds of the invention include:
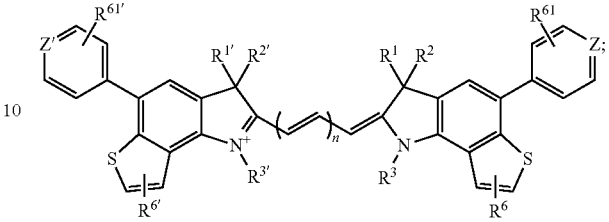
for example:
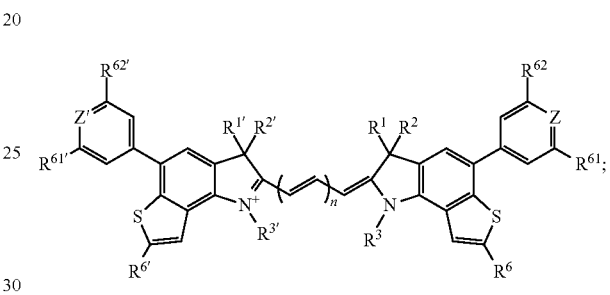
for example:
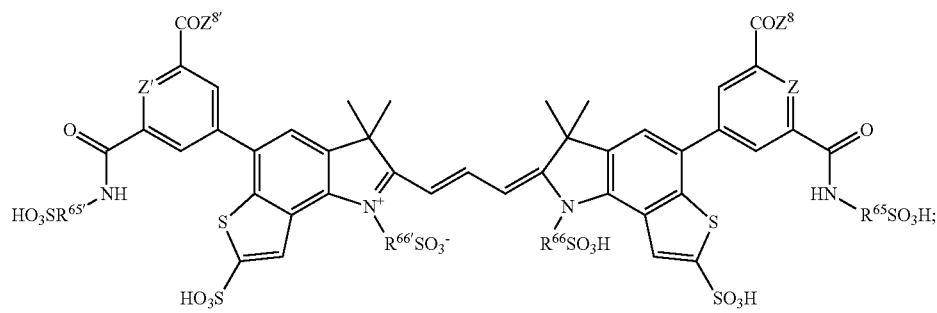
for example:
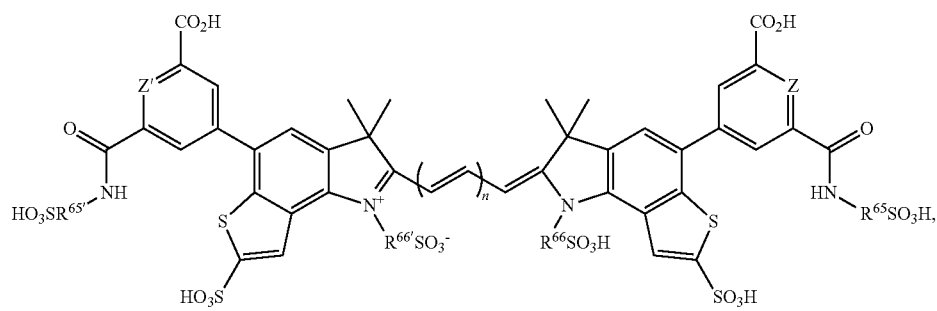

wherein $R^{61}$, $R^{61'}$, $R^{62}$ and $R^{62'}$ are members independently selected from $CH_3$, $C(O)Z^8$, $NH(CH_2)_iSO_3H$. Z and Z' are members independently selected from N and CH; and n is 1, 2 or 3. The index i is an integer from 1 to 10. $Z^8$ is a member selected from OH, O—, a reactive functional group, a component of a reactive functional group and a linkage fragment covalently binding the compound to a carrier molecule. $R^{65}$, $R^{65'}$, $R^{66}$ and $R^{66'}$ are independently members selected from substituted or unsubstituted alkyl having from 2, 3, 4, 5 or 6 carbon atoms.

In an exemplary embodiment, $Z^8$ is a member selected from $N(R^{75})R^{76}C(O)Z^{12}$, in which $R^{75}$ is a member selected from H, substituted or unsubstituted alkyl and substituted or unsubstituted heteroalkyl. $R^{76}$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. $Z^{12}$ is selected from OH, O—, a reactive functional group, a component of a reactive functional group and a linkage fragment covalently binding the compound to a carrier molecule. In various embodiments, $Z^{12}$ is OH. In various embodiment, $R^{75}$ is H. In various embodiments, $R^{76}$ is substituted or unsubstituted $C_1$-$C_6$ alkylene. In an exemplary embodiment, each of these conditions is met in a single compound.

Exemplary compounds of the invention include:

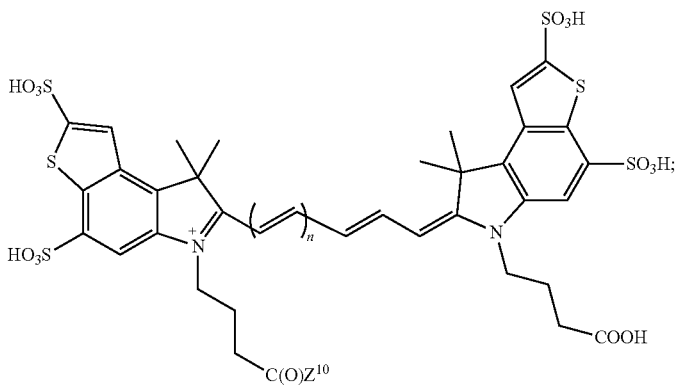

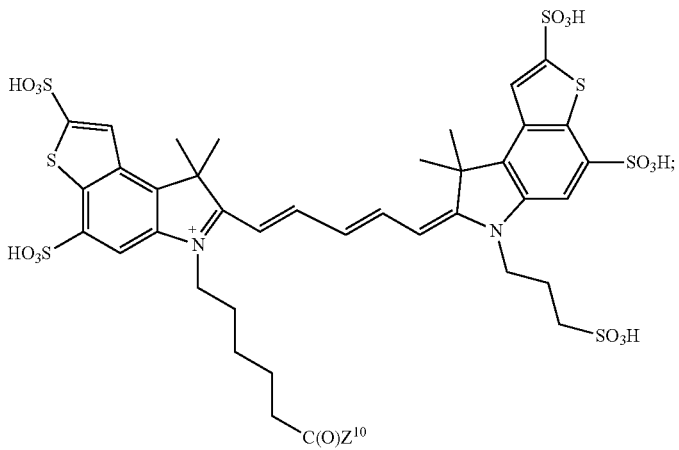

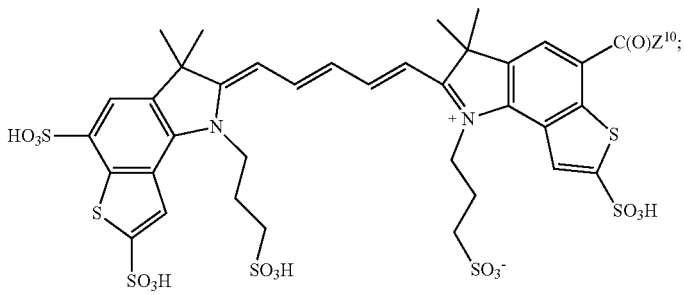

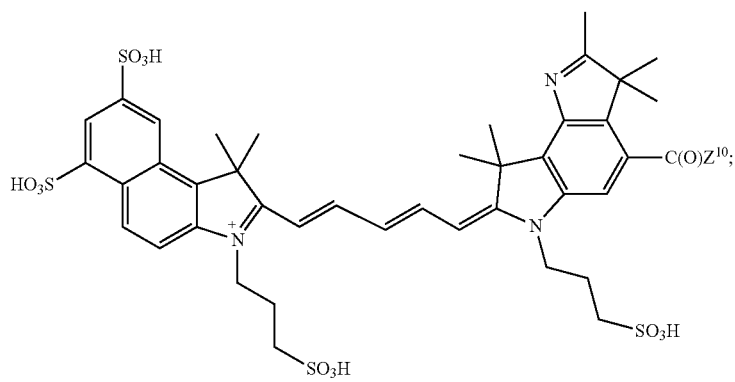
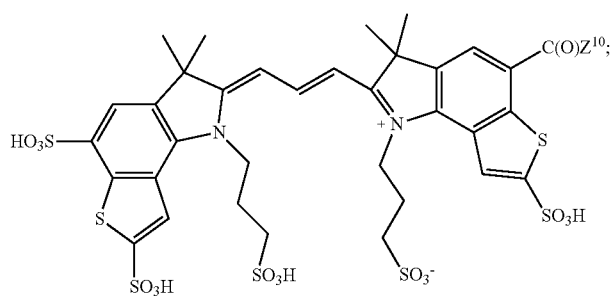
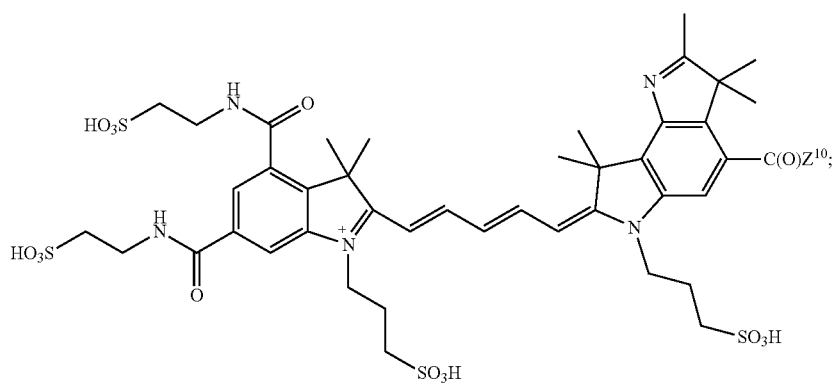
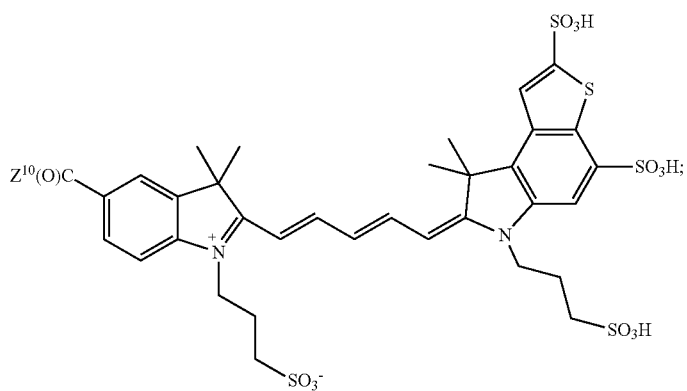

-continued
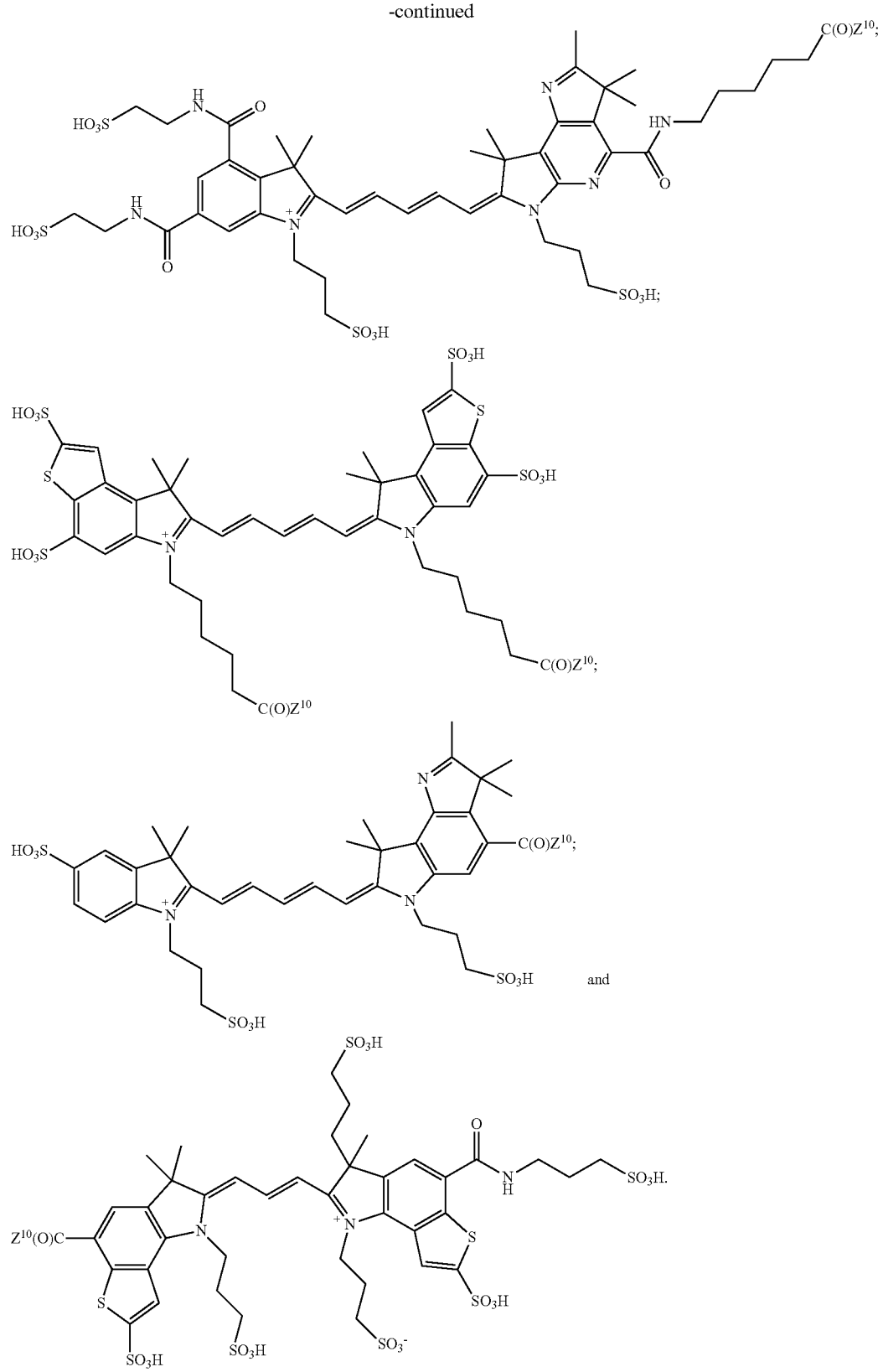
The symbol $Z^{10}$ represents a member selected from OH, $O^-$ the reactive functional group, a component of the reactive functional group or said a linkage fragment covalently binding said compound to a carrier molecule. The index n is 1, 2 or 3. When a molecule has more than one $Z^{10}$, each $Z^{10}$ is independently selected.

In various embodiments, the compounds of the invention include one or more substituent independently selected from SO₃H, alkyl sulfonic acid, alkylcarboxylic acid, sulfonamidoalkylsulfonic acid, amidoalkylsulfonic acid, amidoalkylcarboxylic acid, amidoalkylsulfonic acid, acyloxyalkylsulfonic acid, acyloxyalkylsulfonic acid, and substituted or unsubstituted heteroaryl (e.g., pyridyl). Those substituents that include an alkyl subunit, in exemplary embodiments, include 1, 2, 3, 4, 5, 6, 7, 8, 9, 10, 11, 12 or more carbon atoms in the alkyl chain of the alkyl subunit. In various embodiments, the functional group is located at the terminus of an alkyl chain having the other terminus covalently bound to the cyanine nucleus.

In various embodiments of the invention, the compounds are substituted with one or more alkylsulfonic acid having the formula:

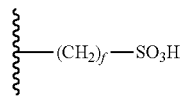

wherein each f is an integer independently selected from 1, 2, 3, 4, 5, 6, 7, 8, 9, 10, 11, 12, 13, 14, 15, 16 or greater.

Various linker, scaffold and other components of use in practicing the instant invention are set forth in commonly owned U.S. patent application Ser. No. 13/218,395, titled "Functionalized Cyanine Dyes (PEG)", Ser. No. 13/218,436, titled "Phospholinked Dye Analogs With An Amino Acid Linker", Ser. No. 13/218,382, titled "Scaffold-Based Polymerase Enzyme Substrates", Ser. No. 13/218,439, titled "Molecular Adaptors for Dye Conjugates", Ser. No. 13/218,412, titled "Functionalized Cyanine Dyes (PEG)", Ser. No. 13/218,428, titled "Cyanine Dyes" and PCT Patent Application Nos. PCT/US2011/49242, titled "Functionalized Cyanine Dyes", PCT/US2011/49247, titled "Cyanine Dyes", and PCT/US2011/49249, titled "Scaffold-Based Polymerase Enzyme Substrates". The disclosures of each of these applications is incorporated herein by reference in their entirety for all purposes.

Chemical synthesis of the compounds of the invention is readily accomplished using art-recognized reagents and techniques. The examples appended hereto provide numerous examples of the synthesis of the cyanine dyes of the invention.

In various embodiments, the invention provides conjugates of the cyanines with a carrier molecule which is a nucleic acid. In an exemplary embodiment, the conjugate has the formula:

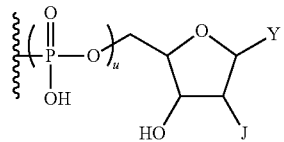

wherein u is selected from the integers 1, 2, 3, 4, 5, 6, 7 and 8. J is a member selected from H, OH, and OMe. Y is a nucleobase. The cyanine dye is attached to the carrier molecule through a linkage fragment in an exemplary embodiment.

A further exemplary nucleic acid conjugate of the invention has the formula:

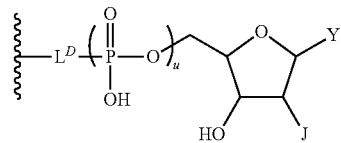

wherein $L^D$ is a member selected from:

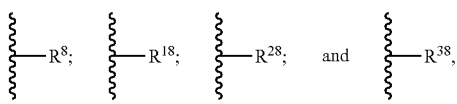

in which u, J, Y, $R^8$, $R^{18}$, $R^{28}$ and $R^{38}$ are as defined hereinabove.

Figure 1B:
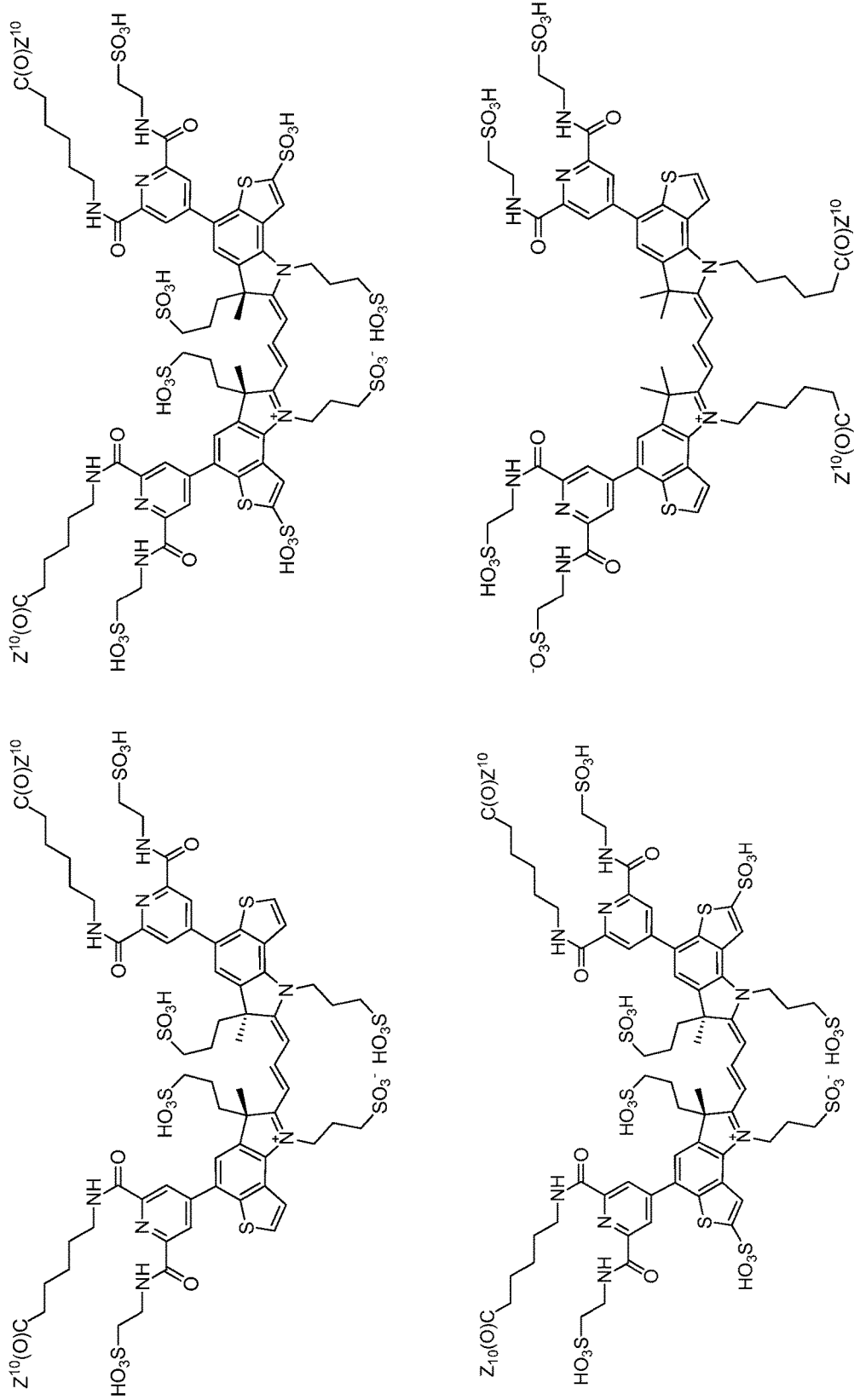
Figure 1C:
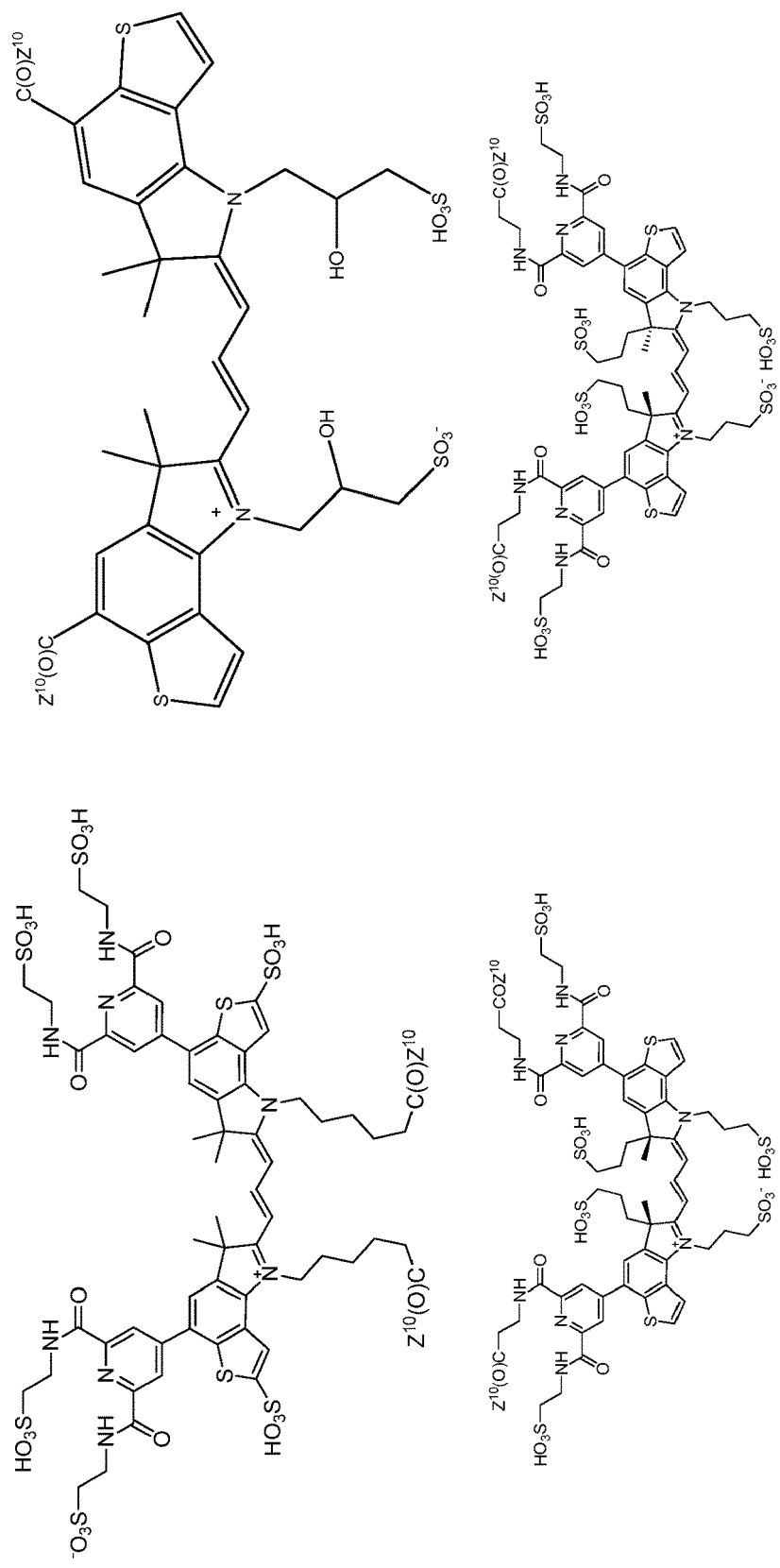
Figure 1D:
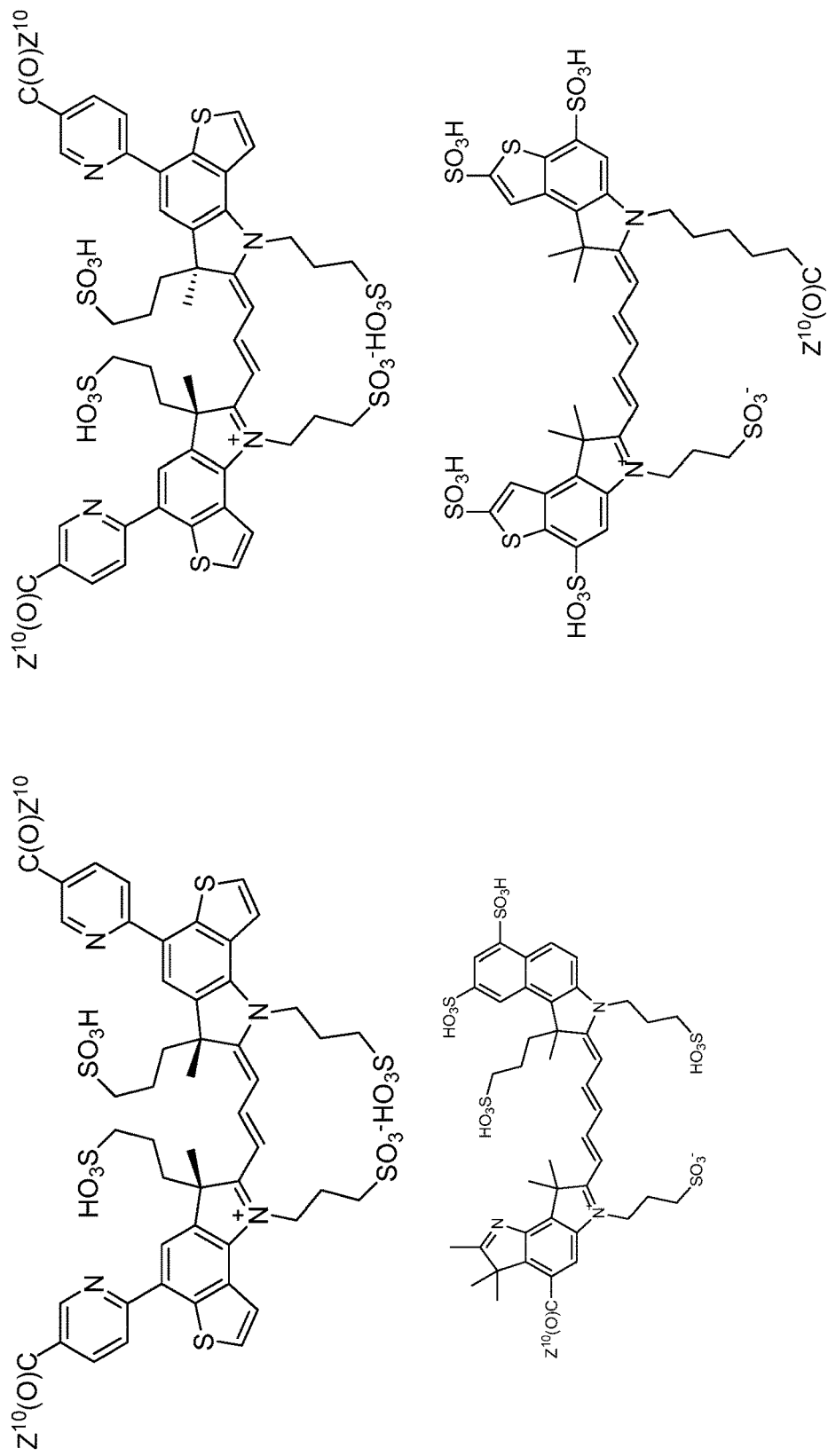
Figure 1E:
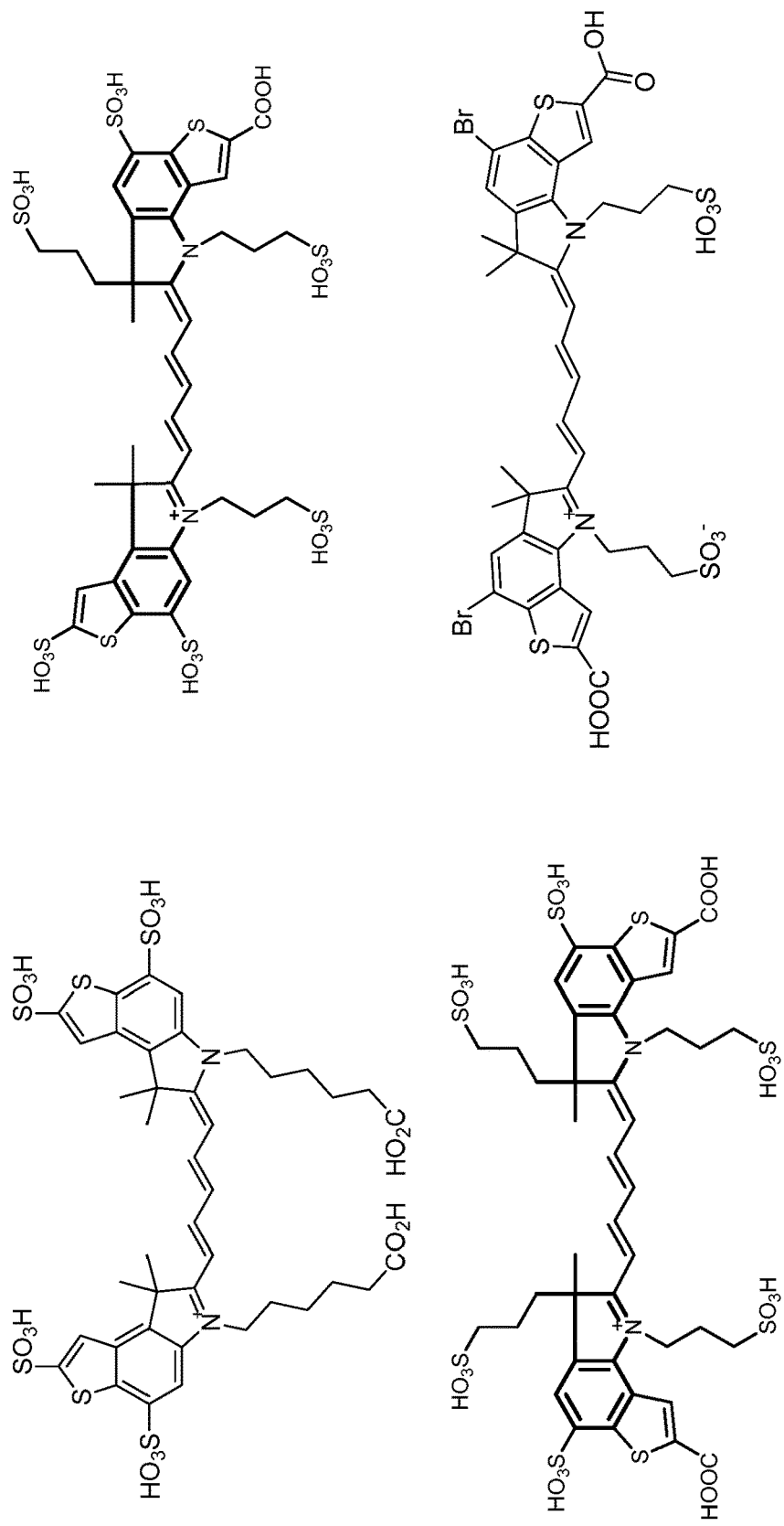
Figure 1F:
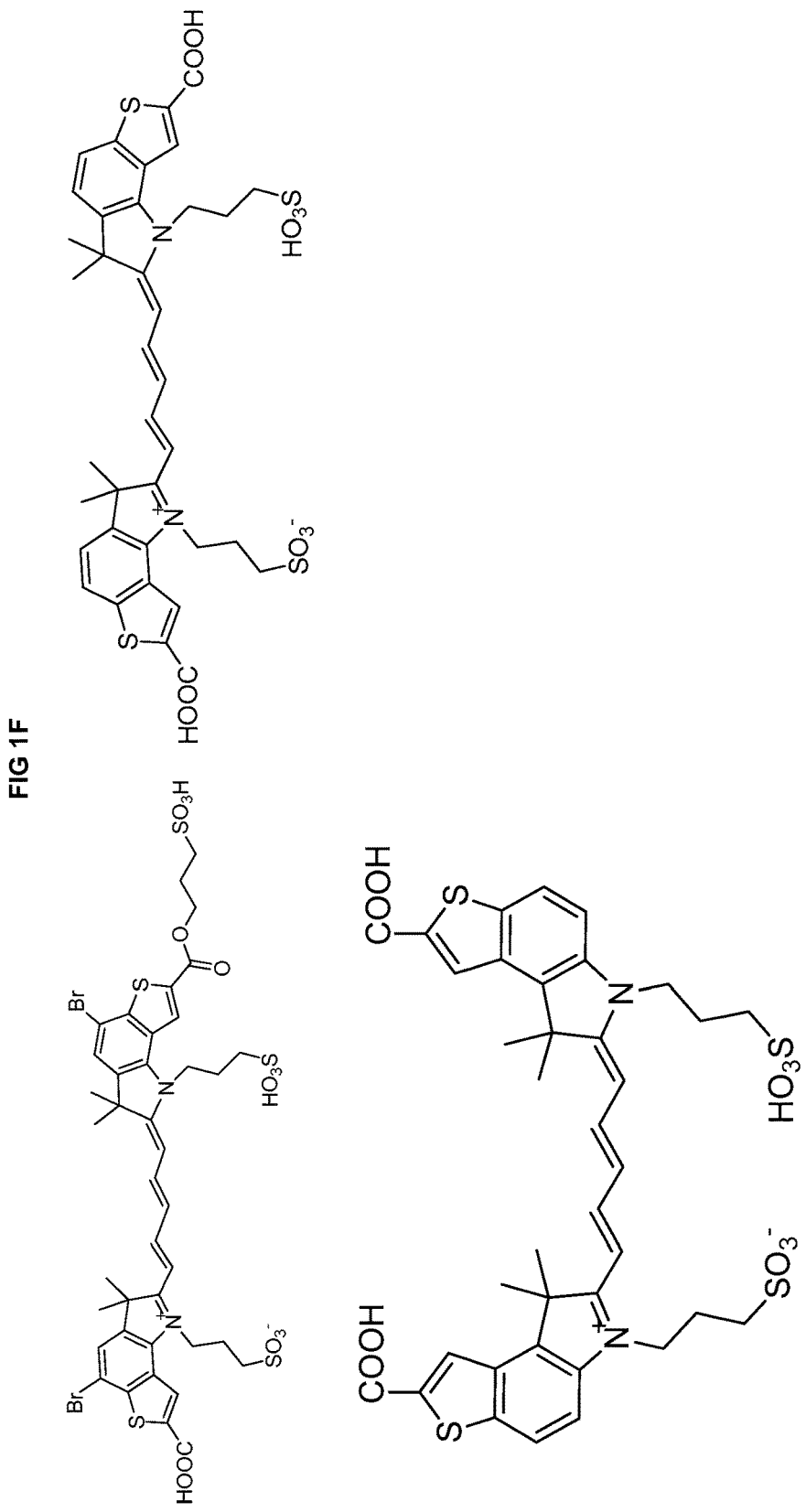

Additional compounds of the invention are set forth in FIG. 1 (A-F) appended hereto. As will be apparent to those of skill in the art, the carboxylic acid moieties in the compounds of FIG. 1 can be converted to a reactive functional group, or they can be derivatized to comprise a component of a linkage fragment linking the cyanine to a carrier molecule.

The invention also provides nucleic acid sequences including one or more cyanine dye of the invention as a modifying group. Chemical synthesis of nucleic acid sequences containing the cyanine dyes of the invention is generally automated and is performed by coupling nucleosides through phosphorus-containing covalent linkages. The most commonly used oligonucleotide synthesis method involves reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a mono- or bis-phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the cyanine-based fluorescent compound of the invention is attached to a nucleic acid, the carrier molecule is produced by either synthetic (solid phase, liquid phase or a combination) or enzymatically or by a combination of these processes.

Another synthetic strategy for the preparation of oligonucleotides is the H-phosphonate method (B. Froehler and M. Matteucci, *Tetrahedron Lett.*, vol 27, p 469-472, 1986). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (N. Sinha and R. Cook, *Nucleic Acids Research*, Vol 16, p. 2659, 1988).

In an exemplary embodiment, the synthesis and purification of the nucleic acid conjugates of compounds of the invention results in a highly pure conjugate, which, if it is a mixture, less than about 30% of the nucleic acid is unlabeled with a dye of the invention, preferably less than about 20% are unlabeled, more preferably less than about 10%, still more preferably less than about 5%, more preferably less than about 1%, more preferably less than about 0.5%, or more preferably less than about 0.1% and even more preferably less than 0.01% of the nucleic acid is unlabeled with a cyanine dye of the invention. In certain embodiments, the nucleic acid (e.g., nucleotides and/or nucleotide analogs) is incorporatable by a polymerase enzyme in a template-dependent polymerization reaction.

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.) VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

Reactive Functional Groups

The compounds of the invention are assembled from covalent bonding reactions between precursors bearing a reactive functional group, which is a locus for formation of a covalent bond between the precursors. The precursors of compounds of the invention bear a reactive functional group, which can be located at any position on the compound. The finished dye conjugates can include a further reactive functional group at any point on the molecule. In various embodiments, a reactive functional group on the cyanine is reacted with a reactive functional group on a carrier molecule (or a linker attached to a carrier molecule) to couple the two components together covalently through a linkage fragment.

Exemplary species include a reactive functional group attached directly to a cyanine nucleus (e.g., aryl ring or methine bridge) or to a linker attached to a component (e.g., aryl ring or methine bridge) of the dye moiety. Other molecules include a reactive functional group attached to a polyvalent moiety. An exemplary reactive functional group is attached to an alkyl or heteroalkyl moiety on the dye. When the reactive group is attached a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive dye-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxyphthalimide, N-hydroxybenzotriazole esters, p-nitrophenyl esters; acid halides; acyl imidazoles; thioesters; alkyl, alkenyl, alkynyl and aromatic esters; and activating groups used in peptide synthesis;
(b) hydroxyl groups and hydroxylamines, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e.g., imines, hydrazones, semicarbazones or oximes, or via such mechanisms as Grignard addition or alkyllithium addition;
(f) sulfonyl halide groups for reaction with amines, for example, to form sulfonamides;
(g) thiol groups, which can be converted to disulfides or reacted with acyl halides, for example;
(h) amine, hydrazine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

In various embodiments, the reactive functional group is a member selected from:

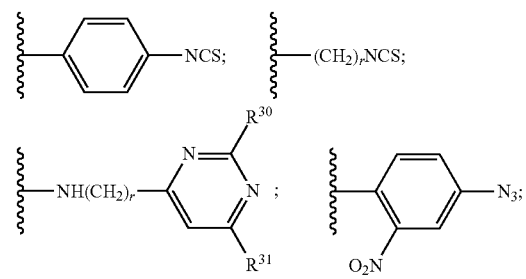

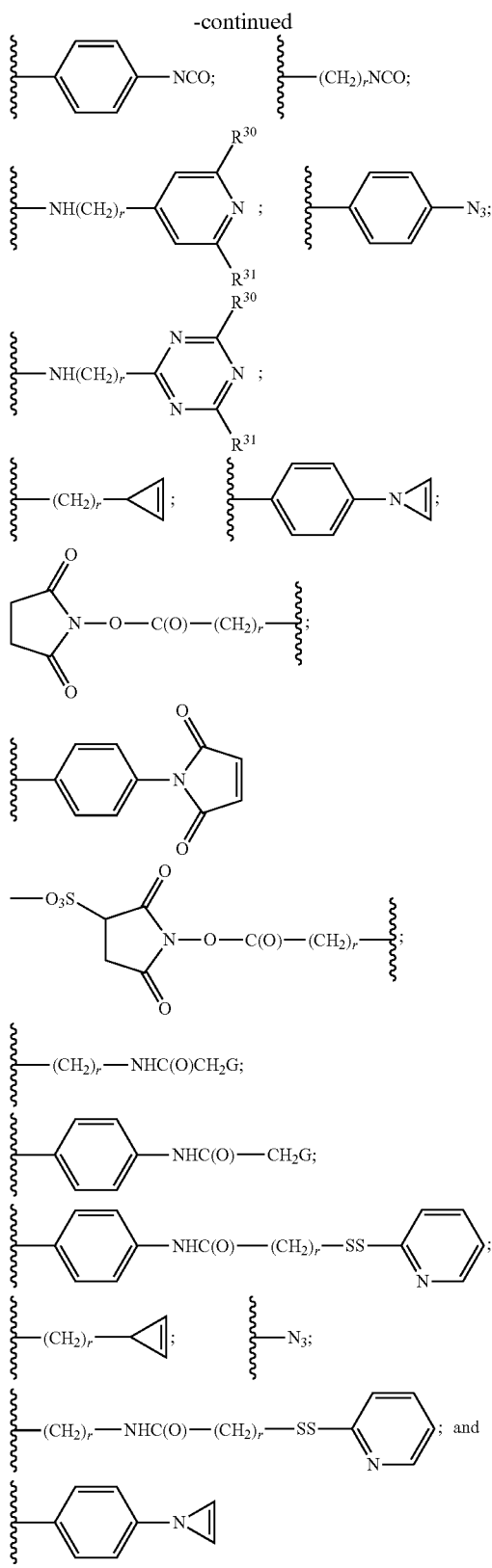

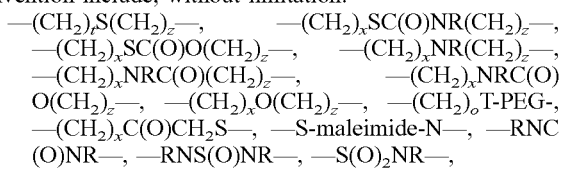

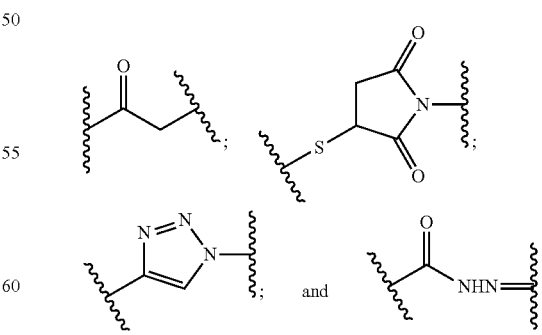

in which each r is independently selected from the integers from 1 to 10; G is a halogen; and $R^{30}$ and $R^{31}$ are members independently selected from H and halogen and at least one of $R^{30}$ and $R^{31}$ is halogen.

The reactive functional groups can be chosen such that they do not participate in, or interfere with, the reactions necessary to assemble or utilize the reactive dye analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a compound of the invention is attached directly to a carrier molecule, the fluorophores can also be attached by indirect means. In various embodiments, a ligand molecule (e.g., biotin) is covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, and peroxidases.

In various embodiments, the cyanine dye is attached to the carrier molecule through a linkage fragment. Exemplary linkage fragments include a bond and a moiety that includes at least one heteroatom, which is formed by the reaction of two reactive functional groups of complementary reactivity. Exemplary linkage fragments of use in the conjugates of the invention include, without limitation:

—$(CH_2)_xS(CH_2)_z$—, —$(CH_2)_xSC(O)NR(CH_2)_z$—,
—$(CH_2)_xSC(O)O(CH_2)_z$—, —$(CH_2)_xNR(CH_2)_z$—,
—$(CH_2)_xNRC(O)(CH_2)_z$—, —$(CH_2)_xNRC(O)O(CH_2)_z$—, —$(CH_2)_xO(CH_2)_z$—, —$(CH_2)_oT$-PEG-,
—$(CH_2)_xC(O)CH_2S$—, —S-maleimide-N—, —RNC(O)NR—, —RNS(O)NR—, —$S(O)_2NR$—, Wherein T is a member selected from S, NH, NHC(O), C(O)NH, NHC(O)O, OC(O)NH, and O. The index o is an integer from 1 to 50; and the indices t and z are independently selected from the integers from 0 to 10. The linkage fragments can also be formed via "Click Chemistry between one component having an azide moiety and another component with an alkyne moiety. The dye can be derivatized with either reactive functional group as can the carrier molecule.

Additional linkage fragments include the structures:

Polyphosphate Analogues

In an exemplary embodiment, the present invention is generally directed to compositions that comprise compounds analogous to nucleotides, and which, in various aspects are readily processable by nucleic acid processing enzymes, such as polymerases. In addition to the unexpectedly advantageous features imparted to the compounds by incorporation of dyes of novel structure, the compounds of the invention generally benefit from one or more advantages of greater stability to undesired enzymatic or other cleavage or non-specific degradation, as well as incorporation efficiencies that are better than or at least comparable to triphosphate, tetraphosphate or pentaphosphate analogs. Exemplary polyphosphates and their uses are set forth in commonly owned U.S. Pat. No. 7,405,281.

In various embodiments, the invention provides polyphosphate analogs of the cyanine dyes of the invention. In various embodiments, the polyphosphate analogs are polyphosphate analogue of a nucleic acid. An exemplary compound according to this motif has the general structure:

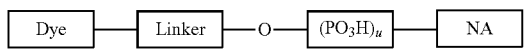

in which NA is the nucleic acid. The index u is an integer selected from 1, 2, 3, 4, 5, 6, 7, 8, 9 or 10.

In an exemplary embodiment, the polyphosphate analogue of the invention has the general structure:

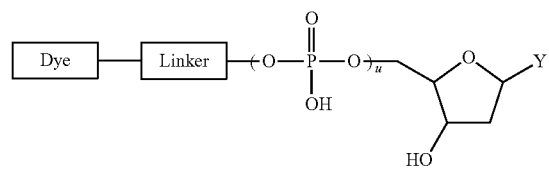

in which Y is a naturally occurring or non-natural nucleobase.

In various embodiments, the polyphosphate analogue of the invention has the general structure:

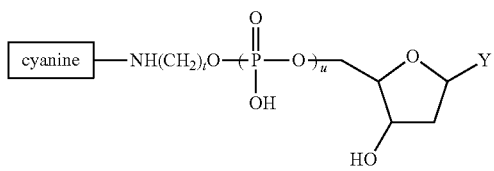

in which t is an integer selected from 1-40, more particularly, 1, 2, 3, 4, 5, 6, 7, 8, 9, 10, 11, 12, 13, 14, 15, 16, 17, 18, 19, 20 or higher.

In an exemplary embodiment, the polyphosphate analogue of the invention has the general structure:

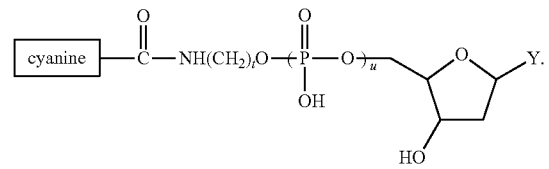

As used above, the cyclic sugar moiety also represents species such as:

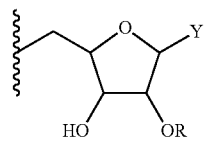

in which R is H or substituted or unsubstituted alkyl, e.g., Me.

In an exemplary embodiment, the cyanine dye component comprises multiple cyanine dyes bound to a common polyvalent scaffold or amplifier. Examples of such scaffold-based cyanine dyes are described in commonly owned PCT Patent Application No. PCT/US11/49249, titled "Scaffold-Based Polymerase Enzyme Substrates", the disclosure of which is incorporated in its entirety herein by reference for all purposes. Examples of dyes that can be incorporated with the dyes of the instant invention into a scaffold-based dye are set forth in U.S. patent application Ser. Nos. 13/218,395 and 13/218,412, titled "Functionalized Cyanine Dyes (PEG)", and PCT Application No. PCT/US11/49242, the disclosures of which are incorporated in their entirety herein by reference for all purposes. The scaffold-based dyes of the invention can include FET or FRET pairs. In an exemplary embodiment, the scaffold-based dye composition includes a Cy3 and a Cy5 dye attached to a common polyvalent scaffold or amplifier. In various embodiments, the linker component includes a peptide component. Exemplary peptide components are set forth in commonly owned U.S. patent application Ser. No. 13/218,436, titled, "Phospho-linked Dye Analogs With An Amino Acid Linker", the disclosure of which is incorporated in its entirety herein by reference for all purposes. In various embodiments, the linker or cyanine dye component includes an adaptor moiety as set forth in commonly owned U.S. patent application Ser. No. 13/218,439, titled "Molecular Adaptors For Dye Conjugates", the disclosure of which is incorporated in its entirety herein by reference for all purposes.

Probes

The invention provides probes having a dye of the invention conjugated to a carrier molecule, for example, a target species (e.g., receptor, enzyme, etc.) a ligand for a target species (e.g., nucleic acid, peptide, etc.), a small molecule (e.g., drug, pesticide, etc.), a solid support and the like. The probes can be used for in vitro and in vivo applications. Exemplary probes are those in which the dye is conjugated to the carrier molecule through an adaptor or through a linker-adaptor cassette.

Small Molecule Probes

The dyes of the invention can be used as components of small molecule probes. In an exemplary design, a small molecule probe includes a dye of the invention and a second species that alters the luminescent properties of the dyes, e.g., a quencher of fluorescence. In an exemplary embodiment, an agent, such as an enzyme cleaves the dye of the invention, the quencher or both from the small molecule generating fluorescence in the system under investigation (see, for example, Zlokarnik et al., *Science* 279: 84-88 (1998)).

Nucleic Acid Capture Probes

In one embodiment, an immobilized nucleic acid comprising a dye of the invention is used as a capture probe. The nucleic acid probe can be used in solution phase or it can be attached to a solid support. The immobilized probes can be attached directly to the solid support or through a linker arm between the support and the dye or between the support and a nucleic acid residue. Preferably, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length. Exemplary attachment points include the 3'- or 5'-terminal nucleotide of the probe as well as other accessible sites discussed herein.

Chemical synthesis of nucleic acid probes containing a dye of the invention is optionally automated and is performed by coupling nucleosides through phosphorus-containing covalent linkages. The most commonly used oligonucleotide synthesis method involves reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a mono- or bis-phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the dye-based fluorescent compound of the invention is attached to a nucleic acid, the carrier molecule is produced by either synthetic (solid phase, liquid phase or a combination) or enzymatically or by a combination of these processes.

Another synthetic strategy for the preparation of oligonucleotides is the H-phosphonate method (B. Froehler and M. Matteucci, *Tetrahedron Lett.*, vol 27, p 469-472, 1986). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (N. Sinha and R. Cook, *Nucleic Acids Research*, Vol 16, p. 2659, 1988).

In an exemplary embodiment, the synthesis and purification of the nucleic acid conjugates of compounds of the invention results in a highly pure conjugate, which, if it is a mixture, less than about 30% of the nucleic acid is unlabeled with a dye of the invention, preferably less than about 20% are unlabeled, more preferably less than about 10%, still more preferably less than about 5%, more preferably less than about 1%, more preferably less than about 0.5%, more preferably less than about 0.1% and even more preferably less than 0.01% of the nucleic acid is unlabeled with a dye of the invention. In certain embodiments, the nucleic acid (e.g., nucleotides and/or nucleotide analogs) is incorporatable by a polymerase enzyme in a template-dependent polymerization reaction.

Dual Labeled Probes

The present invention also provides dual labeled probes that include both a dye of the invention and another label. Exemplary dual labeled probes include nucleic acid probes that include a nucleic acid with a dye of the invention attached thereto, typically, through an adaptor or adaptor-linker cassette. Exemplary probes include both a dye of the invention and a quencher. The probes are of use in a variety of assay formats. For example, when a nucleic acid singly labeled with a dye of the invention is the probe, the interaction between the first and second nucleic acids can be detected by observing the interaction between the dye of the invention and the nucleic acid. Alternatively, the interaction is the quenching by a quencher attached to the second nucleic acid of the fluorescence from a dye of the invention.

The dyes of the invention are useful in conjunction with nucleic-acid probes in a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the dye of the invention-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci. USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

In view of the well-developed body of literature concerning the conjugation of small molecules to nucleic acids, many other methods of attaching donor/acceptor pairs to nucleic acids will be apparent to those of skill in the art.

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink™ II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Exemplary fluorophores that can be combined in a probe or scaffold-based dye with a dye of the invention include those set forth in Table 1.

TABLE 1

Exemplary Donors or Acceptors for Compounds of the Invention 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5', 5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate TABLE 1-continued Exemplary Donors or Acceptors for Compounds of the Invention 4-methylumbelliferone
ortho cresolphthalein
nitrotyrosine
pararosaniline
Phenol Red
B-phycoerythrin
o-phthaldialdehyde
pyrene and derivatives:
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives
Black Hole Quenchers ™

There is a great deal of practical guidance available in the literature for functionalizing fluorophores and selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

As will be apparent to those of skill in the art the methods set forth above are equally applicable to the coupling to a nucleic acid of groups other than the fluorescent compounds of the invention, e.g., quenchers, intercalating agents, hybridization enhancing moieties, minor groove binders, alkylating agents, cleaving agents, etc.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the quencher moiety is preferably separated from the dye of the invention by at least about 10 nucleotides, and more preferably by at least about 15 nucleotides. The quencher moiety is preferably attached to either the 3'- or 5'-terminal nucleotides of the probe. The dye of the invention moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf)

Peptide Probes

Peptides, proteins and peptide nucleic acids that are labeled with a quencher and a dye of the invention, typically, through an adaptor or linker-adaptor cassette can be used in both in vivo and in vitro enzymatic assays.

Peptide constructs useful in practicing the invention include those with the following features: i) a quencher; ii) a dye of the invention; and iii) a cleavage or assembly recognition site for the enzyme. Moreover, the peptide construct is preferably exists in at least one conformation that allows donor-acceptor energy transfer between the dye of the invention and the quencher when the fluorophore is excited.

In the dual labeled probes of the invention, the donor and acceptor moieties are connected through an intervening linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the dye and the quencher. The separation is measurable as a change in donor-acceptor energy transfer. Alternatively, peptide assembly can be detected by an increase in donor-acceptor energy transfer between a peptide fragment bearing a fluorescent dye and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized Dye Analogues

The dyes of the invention can be immobilized on substantially any polymer, biomolecule, or solid or semi-solid material having any useful configuration. Moreover, any conjugate comprising one or more dye of the invention can be similarly immobilized. In an exemplary embodiment, the dye is a component of a dye-linker cassette and it may be conjugated to the solid support through the linker. Alternatively, the dye is attached to another conjugation component through the linker. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a dye of the invention or a species to which a dye of the invention is conjugated. For clarity of illustration, the following discussion focuses on attaching a reactive dye of the invention to a solid support. The following discussion is also broadly relevant to attaching to a conjugation partner a species that includes within its structure a dye of the invention.

The dyes of the invention are preferably attached to a conjugation partner by forming a bond between a reactive functional group on the dye of the invention and a reactive group on the conjugation partner, thereby derivatizing the conjugation partner with one or more dye of the invention. Alternatively, the reactive group on the dye of the invention is coupled with a reactive group on a linker arm attached to the conjugation partner (or vice versa). The bond between the conjugation partner and the dye of the invention is preferably a covalent bond, although ionic, dative and other such bonds are useful as well. Reactive functional groups which can be used in practicing the present invention are discussed in detail above and include, for example, amines, hydroxyl groups, carboxylic acids, carboxylic acid derivatives, alkenes, sulfhydryls, siloxanes, etc.

When the conjugation partner is a solid support, a large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Microarrays

The present invention also provides microarrays including an immobilized dye of the invention and compounds (e.g., peptides, nucleic acids, bioactive agents, etc.) functionalized with a dye of the invention. Moreover, the invention provides methods of interrogating microarrays using probes that are functionalized with a dye of the invention. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of a dye of the invention in conjunction with nucleic acid microarrays. This focus is intended to be illustrative and does not limit the scope of materials with which this aspect of the present invention can be practiced. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990), Pirrung et al. (U.S. Pat. No. 5,143,854, issued 1992), and also by Fodor et al., (*Science,* 251: 767-773 (1991), Southern et al. (*Genomics,* 13: 1008-1017 (1992), Khrapko, et al., *DNA Sequence,* 1: 375-388 (1991), Kleinfield et al., *J. Neurosci.* 8:4098-120 (1998)), Kumar et al., *Langmuir* 10:1498-511 (1994), Xia, Y., *J. Am. Chem. Soc.* 117:3274-75 (1995), Hickman et al., *J. Vac. Sci. Technol.* 12:607-16 (1994), Mrkish et al. *Ann. Rev. Biophys. Biomol. Struct.* 25:55-78 (1996).

Probes of Enzymatic Reactions

In various embodiments, the invention provides a composition which is a substrate for an enzyme, the substrate comprising a component reacted upon by the enzyme, a fluorescent label component and an amino acid or peptide linker component conjugating these two components. The adaptor component is of use to control the interaction of the dye with the enzyme.

In various embodiments, the adaptor serves to control the interaction between a conjugate of the invention and a protein, such as a DNA polymerase. The adaptor can alter the interaction between the conjugate and the protein through electrostatic, hydrophobic, or steric interactions. In an exemplary embodiment in which the conjugate is utilized in a single molecule nucleic acid sequencing technique, the adaptor reduces photobleaching of the dye, photodamage to the enzyme and/or the strength of the interaction between the dye and the enzyme.

The Methods

In addition to the compounds of the invention, there is also provided an array of methods utilizing the compounds. The following discussion is intended to be illustrative of the type and scope of methods with which the compounds of the invention can be practiced and should not be interpreted as being either exhaustive or limiting.

Monitoring Enzymatic Reactions

Peptides, proteins and peptide nucleic acids that are labeled with a quencher and a dye of the invention can be used in both in vivo and in vitro enzymatic assays. In an exemplary embodiment, the dye is attached to the carrier molecule through an adaptor or a linker-adaptor cassette.

Thus, in another aspect, the present invention provides a method for determining whether a sample contains an enzyme. The method comprises: (a) contacting the sample with a peptide construct that includes a dye of the invention; (b) exciting the fluorophore; and (c) determining a fluorescence property of the sample, wherein the presence of the enzyme in the sample results in a change in the fluorescence property.

Peptide constructs useful in practicing the invention include those with the following features: i) a quencher; ii) a dye of the invention; and iii) a cleavage or assembly recognition site for the enzyme. Moreover, the peptide construct preferably exists in at least one conformation that allows donor-acceptor energy transfer between the dye of the invention and the quencher when the fluorophore is excited.

The assay is useful for determining the presence or amount of enzyme in a sample. For example, by determining the degree of donor-acceptor energy transfer at a first and second time after contact between the enzyme and the tandem construct, and determining the difference in the degree of donor-acceptor energy transfer. The difference in the degree of donor-acceptor energy transfer reflects the amount of enzyme in the sample.

The assay methods also can also be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide construct that includes a dye of the invention; (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, nucleotide polymerases (e.g., DNA polymerase), trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

An exemplary assay for proteases are based on donor-acceptor energy transfer from a donor fluorophore to a quencher placed at opposite ends of a short peptide chain containing the potential cleavage site (see, Knight C. G., *Methods in Enzymol.* 248:18-34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

In a further aspect, the invention provides a method of monitoring an enzyme reaction. The method generally comprises providing a reaction mixture comprising die enzyme and at least a first reactant composition, the reactant composition comprising a compound having a reactant component, which is a substrate for the enzyme, a fluorescent label component, and a linker component joining the reactant component to the label component. In various embodiments, the linker component increases the affinity of the conjugate for the enzyme. In various embodiments, the increased affinity reduces the $K_m$ of the reaction, e.g., by 10%, at least 20%, at least 30%, at least 40% or at least 50% relative to the $K_m$ of the reaction with an analogous conjugate without the linker component. The reaction mixture is illuminated to excite the fluorescent label component, and a fluorescent signal from the reaction mixture characteristic of the enzyme reaction is detected.

In an exemplary embodiment, the enzymatic reaction is the reaction of a polymerase with a nucleic acid.

Nucleic Acid Sequencing

In various embodiments, the present invention provides a method for nucleic acid sequencing using one or more compounds of the invention. An exemplary sequencing method is single molecule nucleic acid sequencing. Exemplary dyes used in sequencing include those in which a nucleic acid is bound to the dye through linker.

Significant interest in the sequencing of single DNA molecules dates to 1989 when Keller and colleagues began experimenting with "sequencing by degradation." In their experiments, isolated fully-labeled DNA molecules are degraded by an exonuclease, and individual labeled bases are detected as they are sequentially cleaved from the DNA (Jett, J. H. et al., *J. Biomol. Struct. Dynamics*, 7, 301-309 (1989); Stephan, J. et al., *J. Biotechnol.*, 86, 255-267 (2001); Werner, J. H. et al., *J. Biotechnol.*, 102, 1-14 (2003)). This approach was ultimately compromised by poor DNA solubility caused by the densely-packed dye labels. More recently, alternative single-molecule approaches have been investigated, including "sequencing by synthesis," where bases are detected one at a time as they are sequentially incorporated into DNA by a polymerase (Braslaysky, I. et al., *Proc. Natl. Acad. Sci. USA*, 100, 3960-3964 (2003); Levene, M. J. et al., *Science*, 299, 682-686 (2003); Metzker, M. L., *Genome Res.*, 15, 1767-1776 (2005)); and nanopore sequencing where electrical signals are detected while single DNA molecules pass through protein or solid-state nanopores (Akeson, M. et al., *Biophys. J.*, 77, 3227-3233 (1999); Lagerqvist, J. et al., *Nano Lett.*, 6, 779-782 (2006); Rhee, K. J. et al., Annals of emergency medicine, 13, 916-923 (1984)). So far, only sequencing by synthesis has been successful. In the method of Quake and colleagues (Braslaysky, I. et al., *Proc. Natl. Acad. Sci. USA*, 100, 3960-3964 (2003)), base-labeled nucleotide triphosphates (dNTPs) are incorporated into DNA immobilized on a microscope coverglass. Each type of dNTP is applied separately in a fluidics cycle, and incorporated bases are imaged on the surface after washing away the excess of free nucleotides. While the obtained sequence reads are short, high sequencing rates can potentially be achieved by analyzing billions of different, individual molecules in parallel with applications in re-sequencing and gene expression profiling.

To obtain long single-molecule reads, potentially tens of kilobases, sequencing-by-synthesis approaches using phosphate-labeled nucleotides have been developed (Levene, M. J. et al., *Science*, 299, 682-686 (2003)). These nucleotides are labeled with a fluorophore on the terminal phosphate instead of on the base. Labeled nucleotides are detected while bound to polymerase during the catalytic reaction. The label is released with pyrophosphate as the nucleotide is incorporated into DNA. An advantage is that the DNA remains label-free and fully soluble. Individual polymerase enzymes immobilized on a microscope coverglass are monitored in real time to detect the sequence of incorporated nucleotides. In order to achieve long reads, the polymerase, but not the DNA, can be attached to the coverglass. Polymerase attachment facilitates detection because it keeps the active site at a single position on the coverglass surface. In the alternative format, with the polymerase in solution and the DNA attached, the enzyme active site would be a moving target for detection, diffusing up to several microns from the DNA attachment point as the primer strand is extended from long templates.

U.S. Pat. No. 6,255,083, issued to Williams and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader.

Accordingly, it is within the scope of the present invention to utilize the compounds set forth herein in single molecule DNA sequencing.

In accordance with one embodiment of the methods of invention, the compounds described herein are used in analyzing nucleic acid sequences using a template dependent polymerization reaction to monitor the template dependent incorporation of specific analogs into a synthesized nucleic acid strand, and thus determine the sequence of nucleotides present in the template nucleic acid strand. In particular, a polymerase enzyme is complexed with the template strand in the presence of one or more nucleotides and/or one or more nucleotide analogs of the invention. In preferred aspects, only the labeled analogs of the invention are present representing analogous compounds to each of the four natural nucleotides, A, T, G and C. When a particular base in the template strand is encountered by the polymerase during the polymerization reaction, it complexes with an available analog that is complementary to such nucleotide, and incorporates that analog into the nascent and growing nucleic acid strand, cleaving between the α and β phosphorus atoms in the analog, and consequently releasing the labeling group (or a portion thereof). The incorporation event is detected, either by virtue of a longer presence of the analog in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. In addition to their use in sequencing, the analogs of the invention are also equally useful in a variety of other genotyping analyses, e.g., SNP genotyping use single base extension methods, real time monitoring of amplification, e.g., RT-PCR methods, and the like. See, for example, U.S. Pat. Nos. 7,056,661, 7,052,847, 7,033,764, 7,056,676, 6,917,726, 7,013,054, 7,181,122, 7,292,742 and 7,170,050 and 7,302,146, the full disclosures of which are incorporated herein by reference in their entirety for all purposes.

The present invention also provides methods of using the compounds described herein in performing nucleic acid analyses, and particularly nucleic acid sequence analyses. The methods of the invention typically comprise providing a template nucleic acid complexed with a polymerase enzyme in a template dependent polymerization reaction to produce a nascent nucleic acid strand, contacting the polymerase and template nucleic acid with a compound of the invention, and detecting whether or not a synthon derived from the compound (e.g., monophosphate nucleic acid subunit) was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where label groups released from incorporated analogs are detected.

The invention also provides methods of monitoring nucleic acid synthesis reactions. The methods comprise contacting a polymerase/template/primer complex with a fluorescently labeled nucleotide or nucleotide analog having a nucleotide or nucleotide analog component, a fluorescent label component, and a linker-adaptor component joining the nucleotide or nucleotide analog component to the label component. A characteristic signal from the fluorescent dye is then detected that is indicative of incorporation of the nucleotide or nucleotide analog into a primer extension reaction.

The adaptor linked fluorophores of the invention are of use in single molecule or single molecule real time (SMRT) DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores to be utilized and distinguished in an assay. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

Polymerase Chain Reaction

In another aspect, the invention provides a method for detecting amplification by PCR of a target sequence. Methods of monitoring PCR using dual labeled nucleic acid probes are known in the art. See, *Expert Rev. Mol. Diagn.*, 5(2), 209-219 (2005). Exemplary dyes used in PCR probes include those in which a nucleic acid is bound to the dye through an adaptor or a dye is bound to a nucleic acid through a linker-adaptor cassette.

The dyes and their conjugates described herein can be used in substantially any nucleic acid probe format for PCR. For example, the dyes of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. patent application Ser. No. 09/591,185), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present dyes can be used are reviewed in NONISOTOPIC DNA PROBE TECHNIQUES, Academic Press, Inc. 1992.

Nucleic Acid Detection

In another embodiment, the invention provides a method of detecting a target nucleic acid in an assay mixture or other sample. The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art. Exemplary dyes used in sequencing include those in which a nucleic acid is bound to the dye through an adaptor or a dye is bound to a nucleic acid through a linker-adaptor cassette.

An exemplary method uses a dye of the invention or a conjugate thereof to detect a nucleic acid target sequence. The method includes: (a) contacting the target sequence with a detector nucleic acid that includes a dye of the invention and a quencher; (b) hybridizing the detector nucleic acid to the target sequence, thereby altering the conformation of the detector nucleic acid, causing a change in a fluorescence parameter; and (c) detecting the change in the fluorescence parameter, thereby detecting the nucleic acid target sequence.

In various embodiments, the detector nucleic acid includes a single-stranded target binding sequence. The binding sequence has linked thereto: i) a quencher; and ii) a dye of the invention. Moreover, prior to its hybridization to a complementary sequence, the detector nucleic acid is preferably in a conformation that allows donor-acceptor energy transfer between the quencher and the dye of the invention when the fluorophore is excited. Furthermore, in the methods described in this section, a change in fluorescence is detected as an indication of the presence of the target sequence. The change in fluorescence is preferably detected in real time.

Kits

In another aspect, the present invention provides kits containing one or more dye of the invention or a conjugate thereof. In one embodiment, a kit includes a reactive dye of the invention and directions for attaching this derivative to another molecule. In another embodiment, the kit includes a dye-labeled polyphosphate nucleic acid in which an adaptor is present between the dye (or dye linker cassette) and the polyphosphate nucleic acid. The kit further includes one or more component selected from buffers or other compounds or solutions of use in practicing the method, an enzyme (e.g., a DNA polymerase), cofactors necessary for enzyme reactions, and directions for performing the assay.

The materials and methods of the present invention are further illustrated by the examples that follow. These examples are offered to illustrate, but not to limit the claimed invention.

The following examples are provided by way of illustration only and not by way of limitation. Those of skill in the art will readily recognize a variety of non-critical parameters that could be changed or modified to yield essentially similar results.

EXAMPLES

Example 1

Preparation of A and B

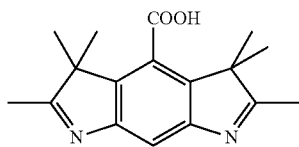
A

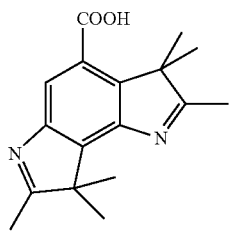
B

To 0.255 g of 3,5-dihydrazinobenzoic acid hydrochloride in 2 mL of acetic acid, 0.54 mL of 3 methyl-2-butanone was added and the resulting mixture was heated at 130° C. for 2.5 hours. The volatile components were evaporated and the crude was purified by HPLC to yield 0.12 g of each derivative.

1.2 Preparation of C

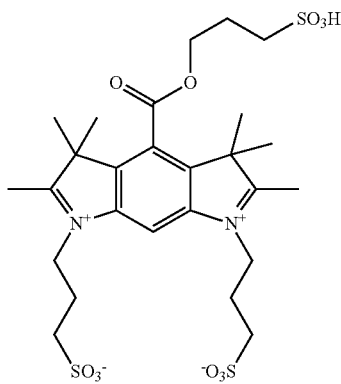
C

A mixture of 0.12 g of A and 0.56 mL of propane sultone and 0.5 mL of sulfolane was heated at 140° C. for 2.5 hours. The reaction mixture was cooled to room temperature and 5 mL of ethyl acetate was added and the supernatant was decanted. The resulting mixture was then heated in 5 mL of 1M HCl at 65° C. for 6 hours and the volatiles were evaporated. The crude material was used without further purification.

1.3 Preparation of D

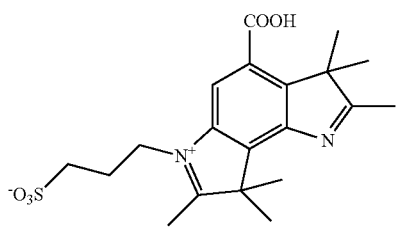
D

A mixture of 0.12 g of B and 0.56 mL of propane sultone and 0.5 mL of sulfolane was heated at 140° C. for 2.5 hours. The reaction mixture was cooled to room temperature and 5 mL of ethyl acetate was added and the supernatant was decanted. The resulting mixture was then heated in 5 mL of 6M HCl at 100° C. for 8 hours and the volatiles were evaporated. The crude material was used without further purification.

1.4 Preparation of E

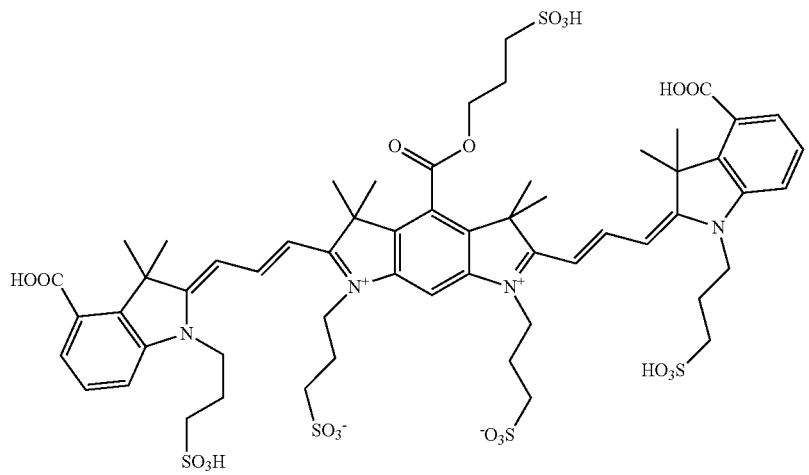
E

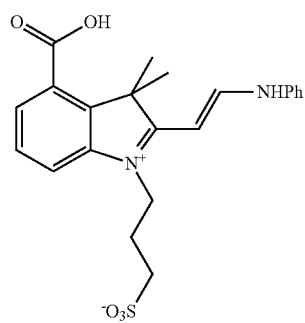
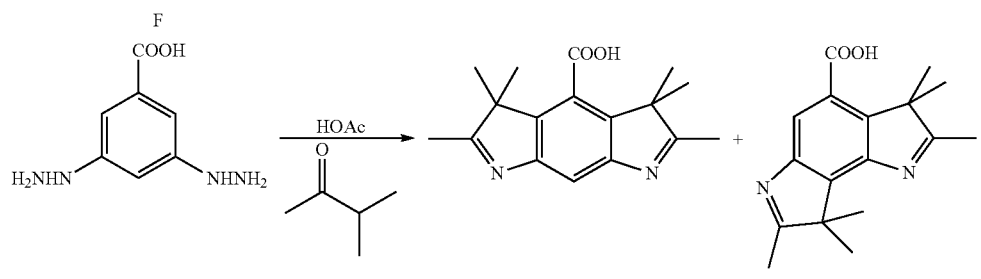
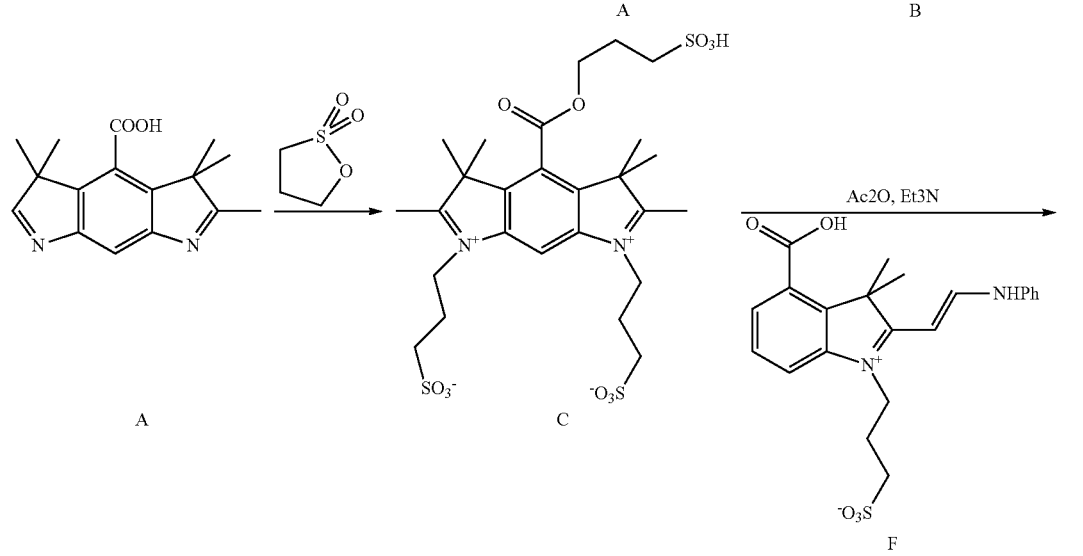
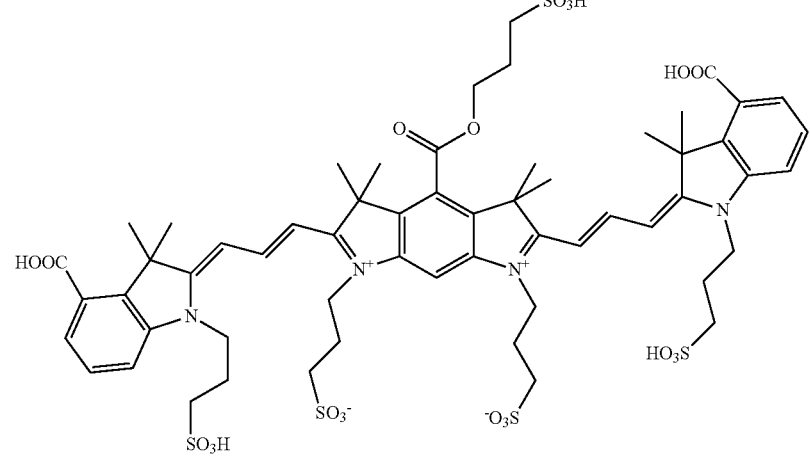

A mixture of several mg of C and an excess of F, acetic anhydride and triethylamine was stirred in about 0.5 mL of DMF at room temperature for 1 hour. About 3 mL of ethyl acetate was added and the crude precipitate was purified by HPLC. The absorption maximum of the product was at 560 nm.

1.5 Preparation of G

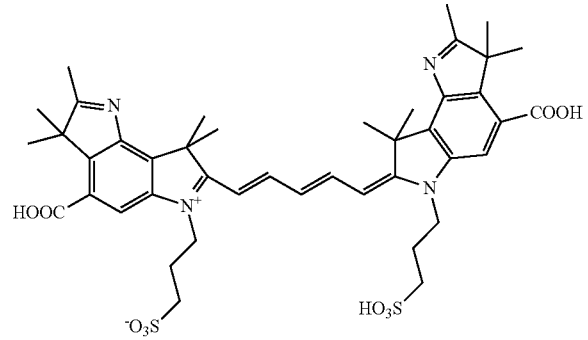

G

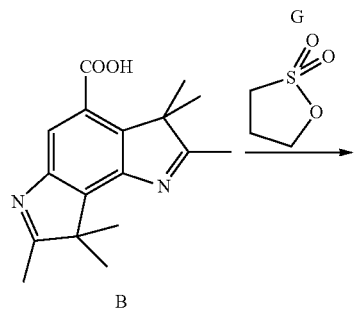

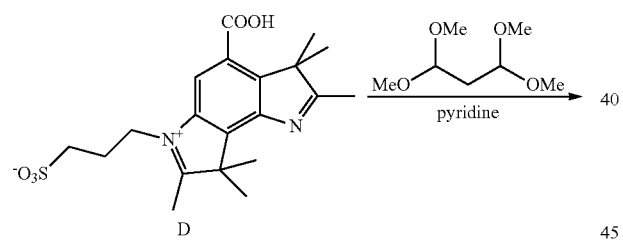

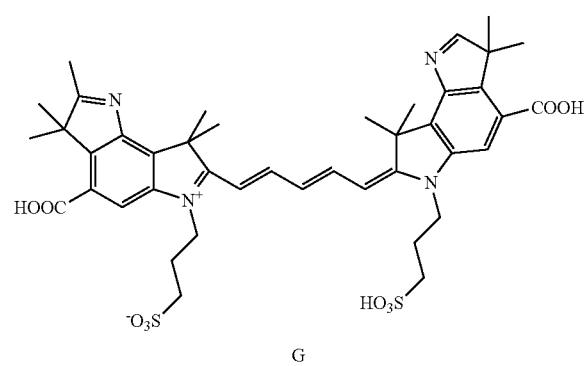

G

Several mg of D were heated in an excess of 1,1,3,3-tetramethoxypropane in pyridine at 100° C. for 30 minutes. The volatile components were evaporated under reduced pressure and the product was isolated by HPLC. The absorption maximum of the product was at 654 nm.

1.6 Preparation of H

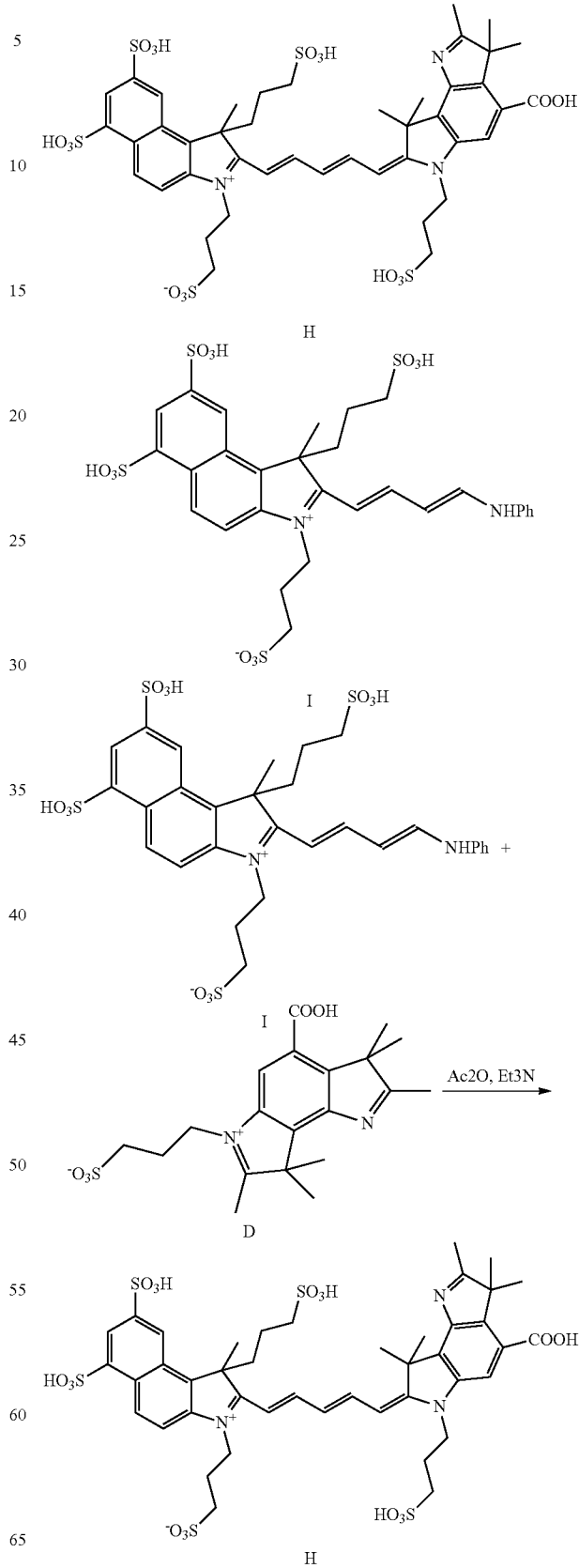

A mixture of about 15 mg of I, 15 mg of D, 50 μL of acetic anhydride, 90 μL of triethylamine was stirred in 1 mL of DMF at room temperature overnight and the product was purified by HPLC. The absorption maximum of the product was at 664 nm.

1.7 Preparation of J

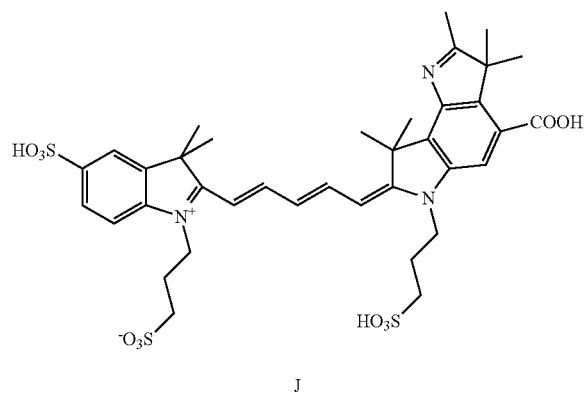

J

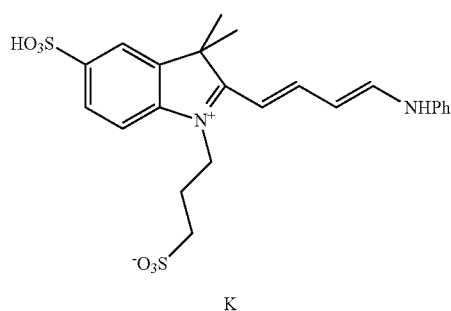

K

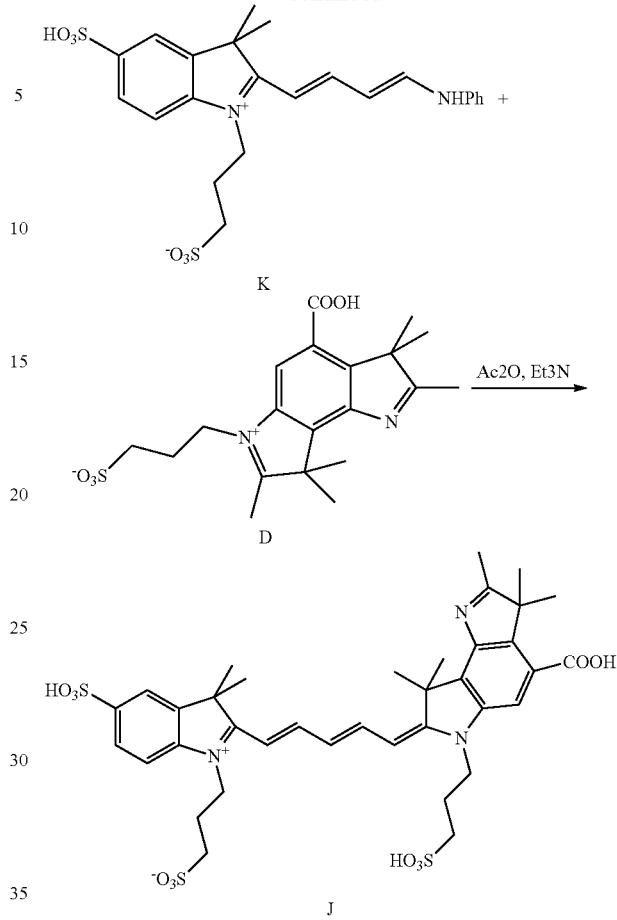

A mixture of about 3 mg of K, 7 mg of D, 40 μL of acetic anhydride and 40 μL of triethylamine in 0.5 mL of DMF was stirred at room temperature for one hour. The product was isolated by HPLC.

1.8 Preparation of L

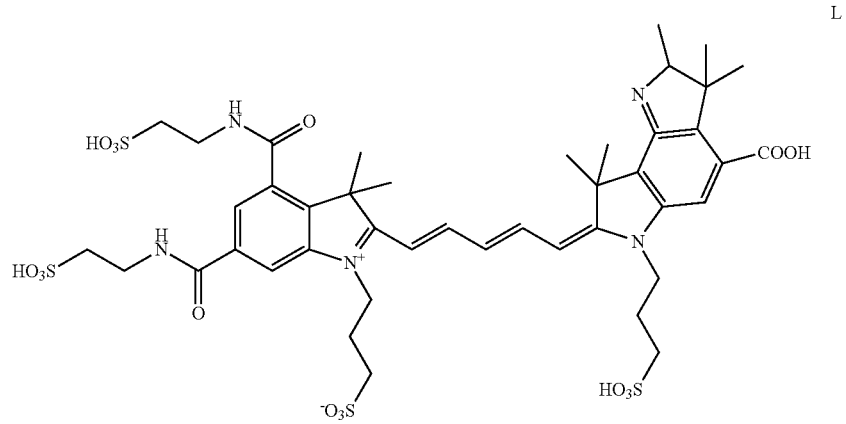

L

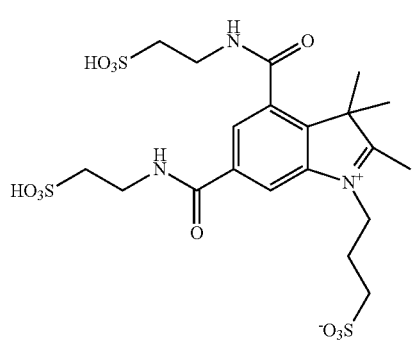

M

A mixture of 0.1 g of D, about 160 mg of M, 0.5 mL of 1,1,3,3-tetramethoxypropane in 3 mL of pyridine was heated at 100° C. for 1.5 hour. At the end of the period, 15 mL of ethyl acetate was added and the supernatant was decanted and the crude was purified by HPLC.

1.9 Preparation of N and O

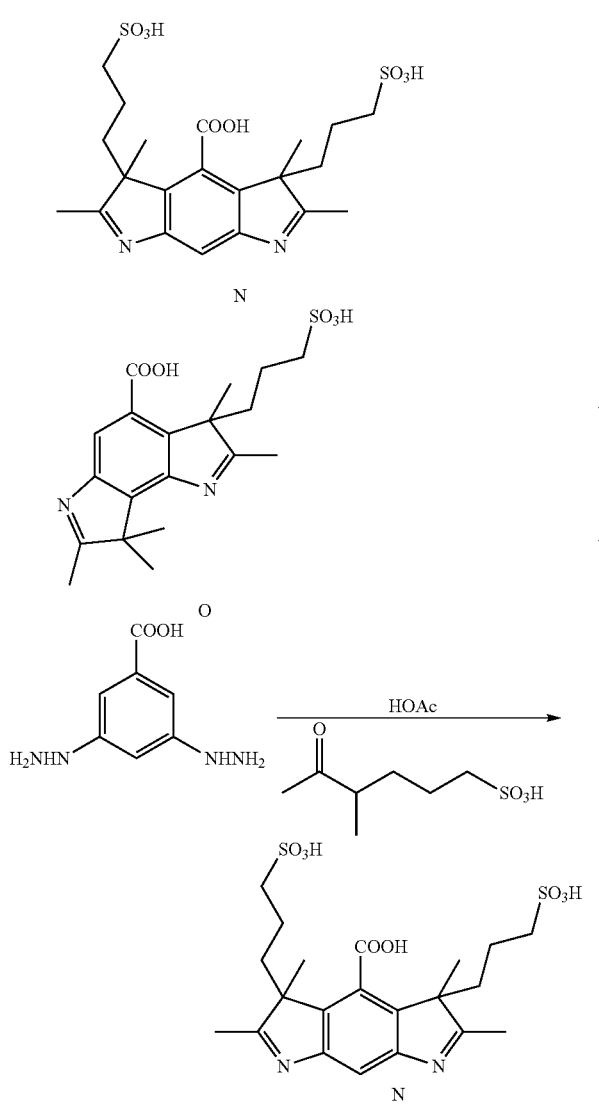

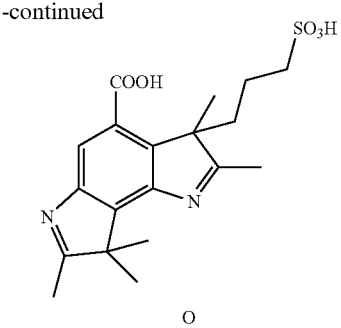

O

A mixture of 0.255 of 3,5-dihydrazinobenzoic acid hydrochloride, 1.0 g of 3-methyl-6-sulfo-2-hexanone in 4 mL of acetic acid was heated at 130° C. for several hours. The products were isolated by HPLC.

1.10 Preparation of P and Q

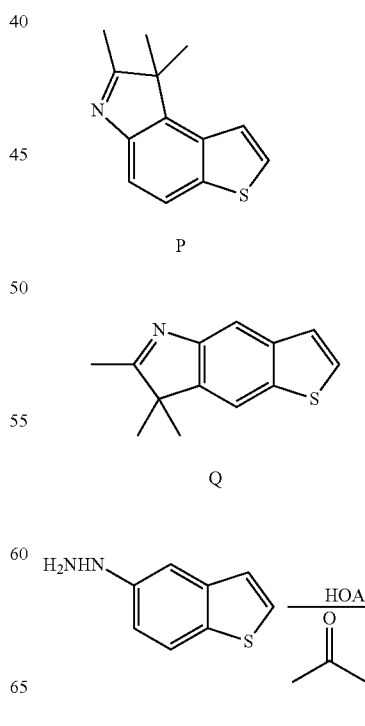

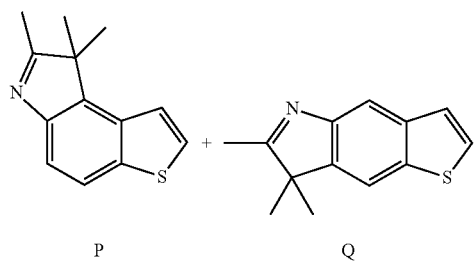

P    Q

A mixture of 0.3 g of 1-benzothiophen-5-hydrazine HCl, prepared from the corresponding 1-benzothiophen-5-amine, 0.64 mL of 3-methyl-2-butanone in 3 ml, of acetic acid was heated at 120° C. for 1.5 hour. Silica gel column isolated 0.12 g of P as the major product and a small amount of the other isomer Q.

1.11 Preparation of R and S

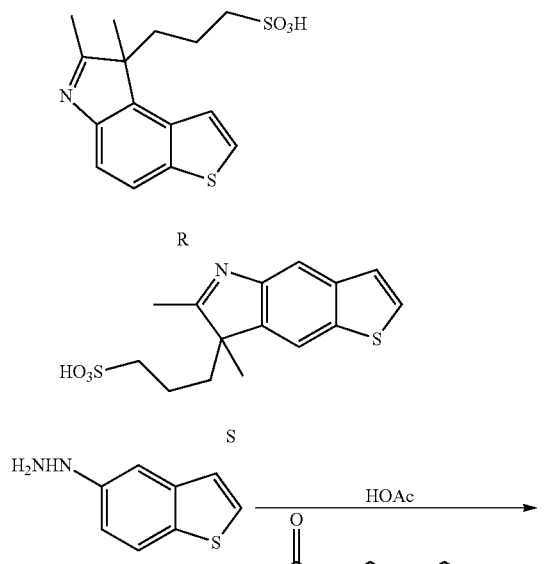

The compounds were prepared by heating 1-benzothiophen-5-hydrazine HCl with 3-methyl-6-sulfo-2-hexanone in acetic acid.

1.12 Preparation of T

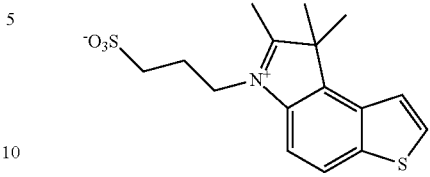

T

A mixture of 29 mg of P, 100 µL of propane sultone in 200 µL, of sulfolane was heated at 115° C. for 1 h and then 3 mL of ethyl acetate was added. The precipitate was recovered and dried and heated in 3 mL of 1 M HC at 60° C. for 5 hours to obtain the desired product.

1.13 Preparation of U

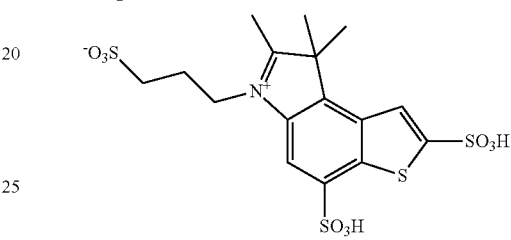

U

To about 5 mg of T, 40 µL of fuming sulfuric acid was added and stirred for 20 minutes. At the end of the period, 1 mL of ethyl acetate was added followed by 0.3 mL of diethyl ether. The product was recovered as a white precipitate by centrifugation.

1.14 Preparation of V

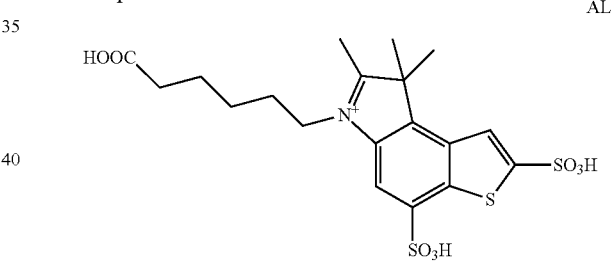

AL

A mixture of 26 mg of W and 195 mg of 6-bromohexanoic acid in sulfolane 100 µL was heated at 130° C. for 4 hours. After cooling down to room temperature, 1 mL of diethyl ether was added and the supernatant was decanted. The crude was further washed with ethyl acetate. To the dried crude product, 0.5 mL of fuming sulfuric acid was added and stirred for 30 minutes; 1 mL of ethyl acetate followed by 7 mL of ether were introduced and the insoluble crude was further washed with 2 mL of ethyl acetate and used without further purification.

1.15 Preparation of X

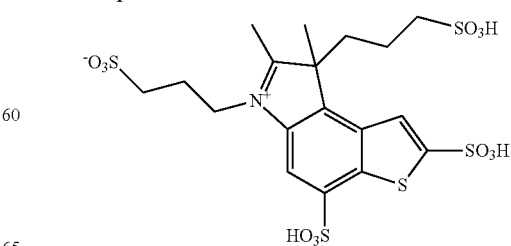

X

The compound was prepared from R.

1.16 Preparation of Y
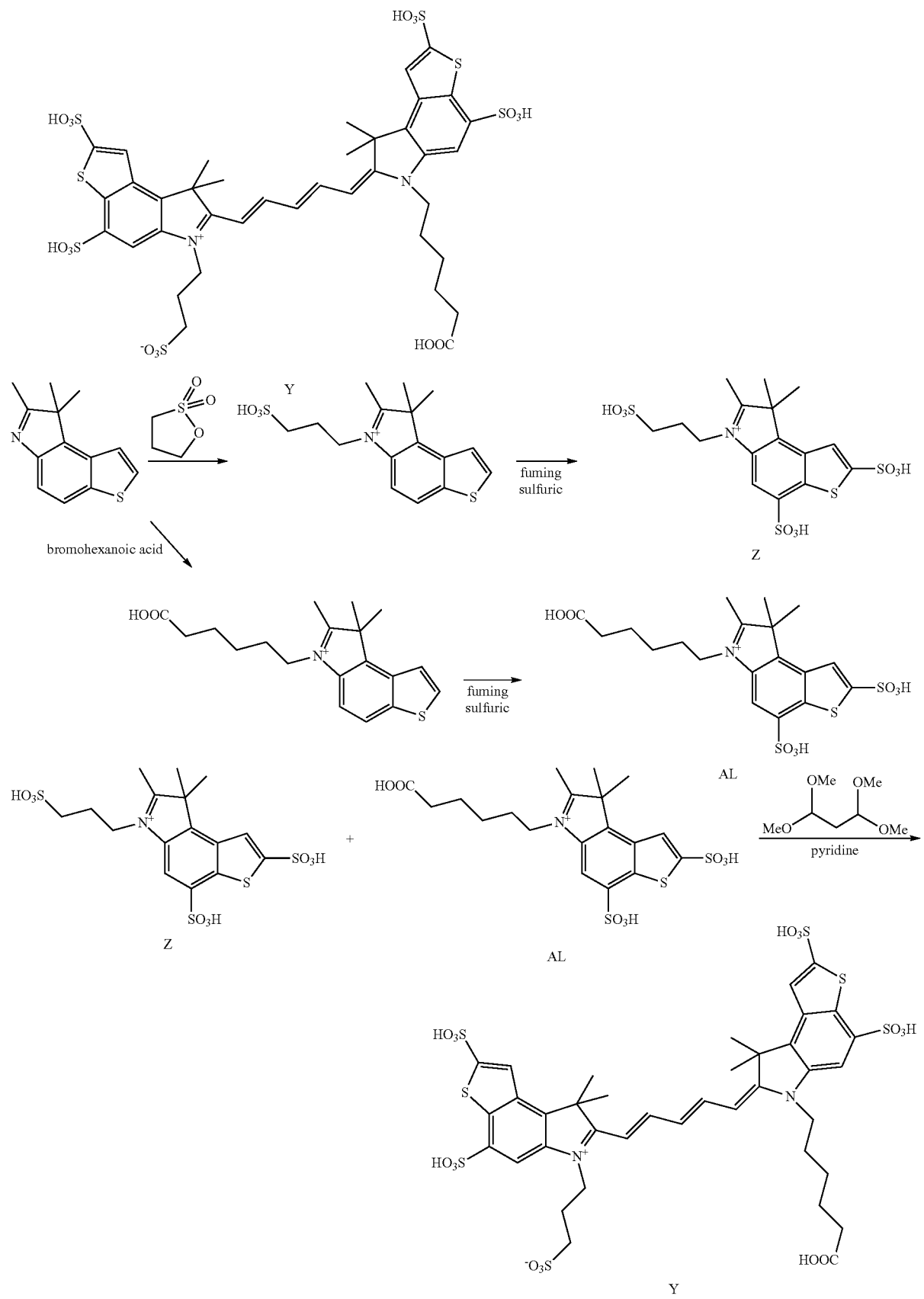

A mixture of crude V from the aforementioned preparation, 20 mg of U, 100 µL of 1,1,3,3-tetramethoxypropane and 0.2 mL of pyridine in 0.4 mL of DMF was heated at 110° C. for 1 h. The corresponding methyl ester was then hydrolyzed by stirring in 1 mL of 0.5 M KOH for 24 hours and the crude was purified by HPLC to obtain 3.2 mg of product. The excitation/emission was about 668/683 nm.

1.17 Preparation of AA

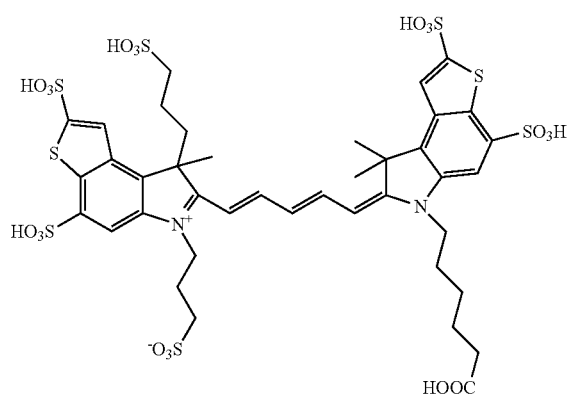

The compound was prepared from X and V by heating them with 1,1,3,3-tetramethoxypropane in pyridine.

1.18 Preparation of AB

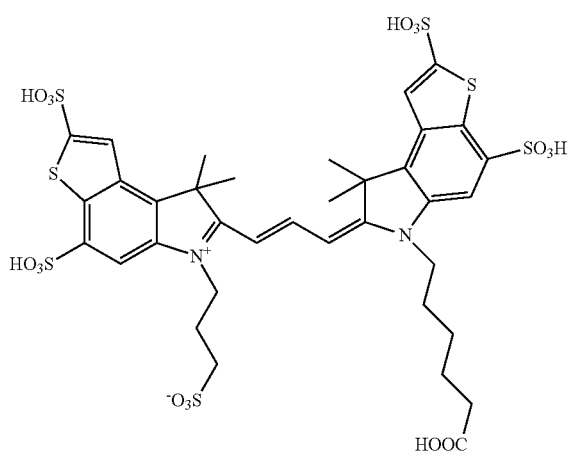

The compound was prepared by a similar procedure for that of Y except using ethyl orthoformate instead of 1,1,3,3-tetramethoxypropane.

1.19 Preparation of AC

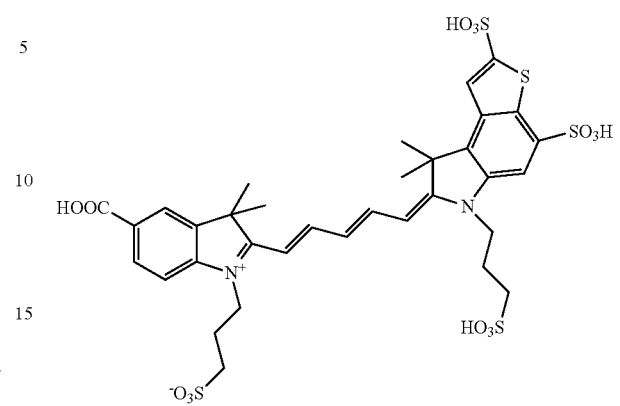

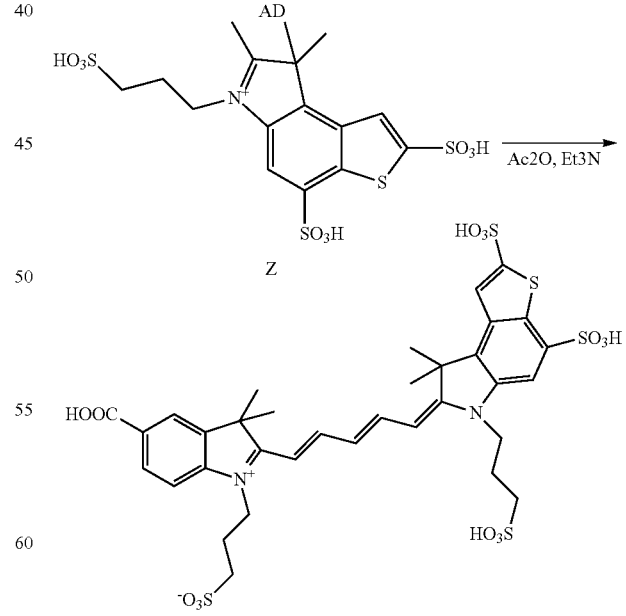

To a mixture of 10 mg of U and 8 mg of AD in 0.2 mL of DMF, 20 µL of acetic anhydride was added followed by 30 µL of triethylamine. After stirring at 35° C. for 5 h, 1 mL of ethyl acetate was added and the crude precipitate was purified by ion exchange to yield 2.1 mg of product.

1.20 Preparation of AE

A mixture of 0.61 g of 1-benzothiophen-4-hydrazine HCl, prepared from the corresponding 1-benzothiophen-4-amine, was heated with 1 mL of 3-methyl-2-butanone in 5 mL of acetic acid at 125° C. for 6 h. All volatile components were evaporated and the crude was purified on a silica gel column to yield 0.26 g of desired product.

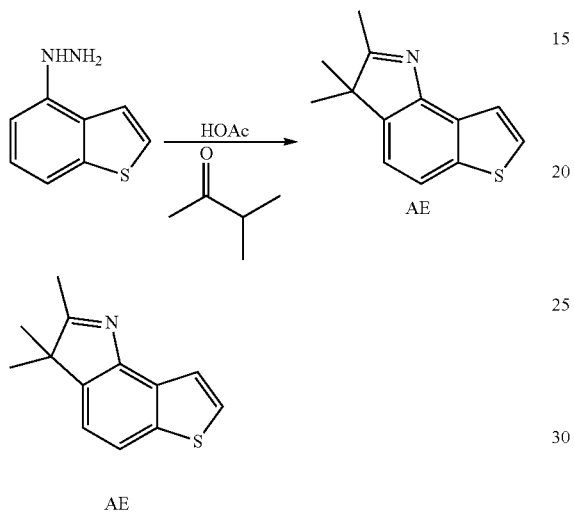

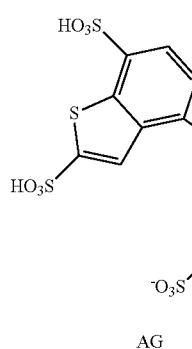

AE 1.21 Preparation of AF

The compound was prepared by heating 1-benzothiophen-4-hydrazine HCl with 3-methyl-6-sulfo-2-hexanone in acetic acid.

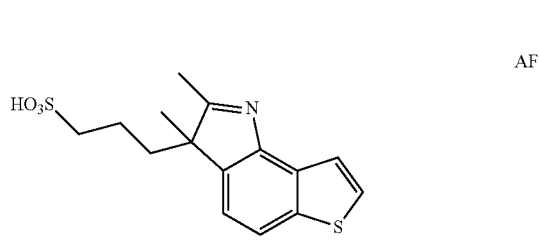 [SMILES: CC1=Nc2c(ccc3sccc23)C1(C)CCCS(=O)(=O)O]

AF 1.22 Preparation of AG

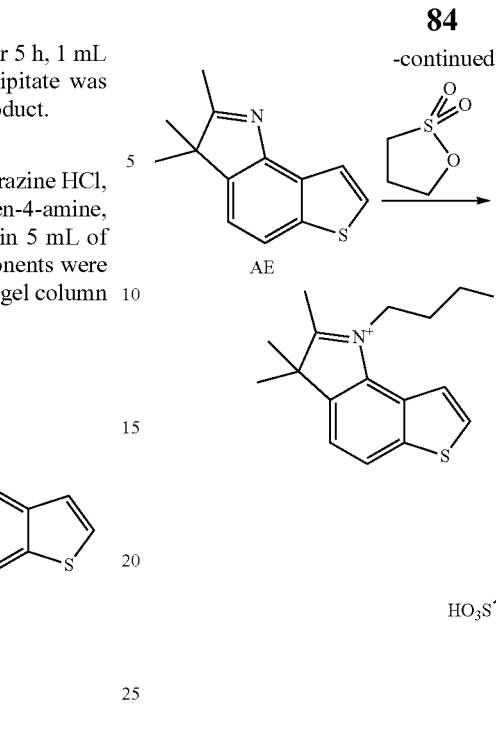

AG

A mixture of 50 mg of AE and 0.2 mL of propane sultone in 0.2 mL of sulfolane was heated at 125° C. for 4 h. To the reaction mixture, 5 mL of ethyl acetate was added and the precipitate recovered was heated in 5 mL of 1 M HCl at 70° C. for 4 hours. All volatile components were evaporated and 0.4 mL of fuming sulfuric acid was added and stirred at room temperature for 12 h. The reaction mixture was added to 6 mL of ethyl acetate slowly and the crude product was recovered from centrifugation and used without further purification.

1.23 Preparation of AH

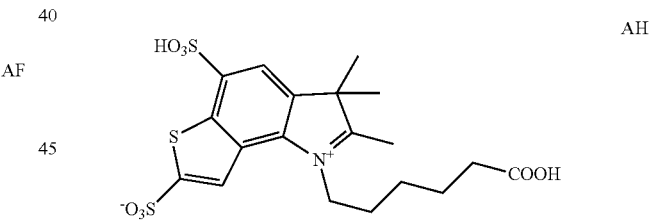

AH

The compound was prepared by heating V except using AE as the starting material.

1.24 Preparation of AI

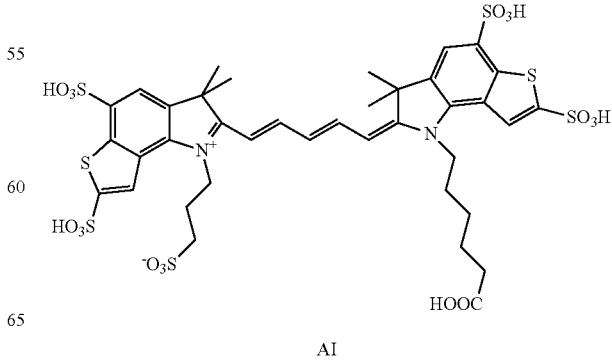

AI

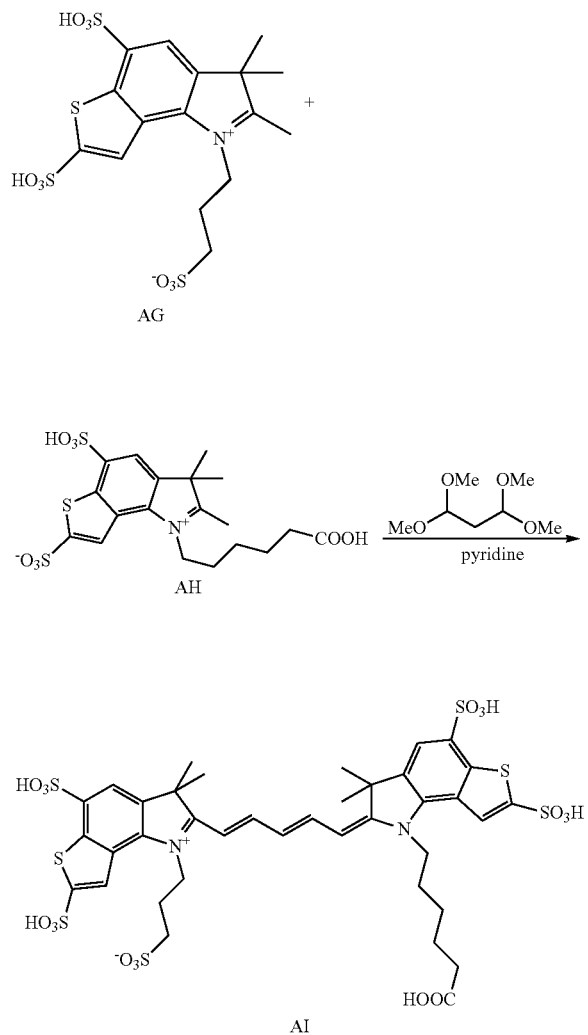
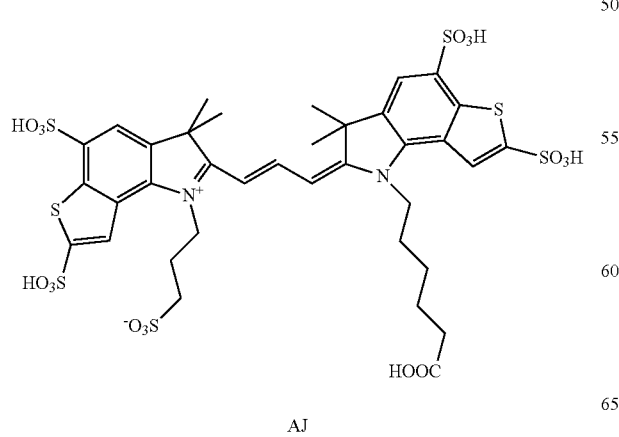
The compound was prepared using AG and AH and following the procedure for Y. The excitation/emission was about 690/710 nm.
1.25 Preparation of AJ
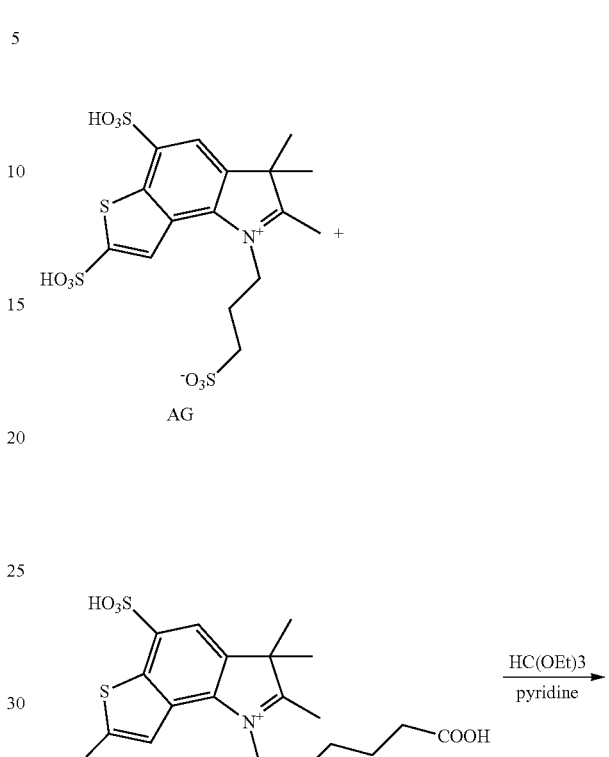
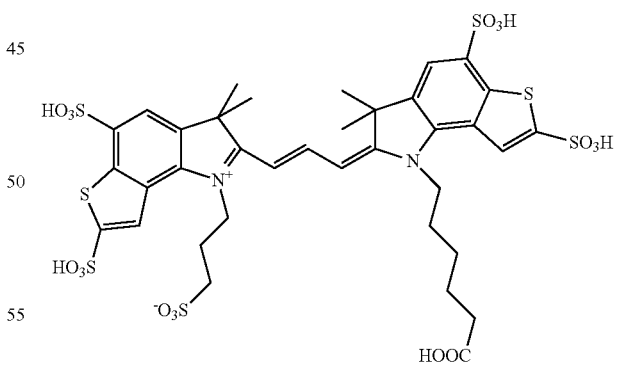
The compound was prepared by using AG and AH as starting materials and heating them with ethyl orthoformate in pyridine at 100° C. The excitation/emission was about 595/609 nm.

1.26 Preparation of AK
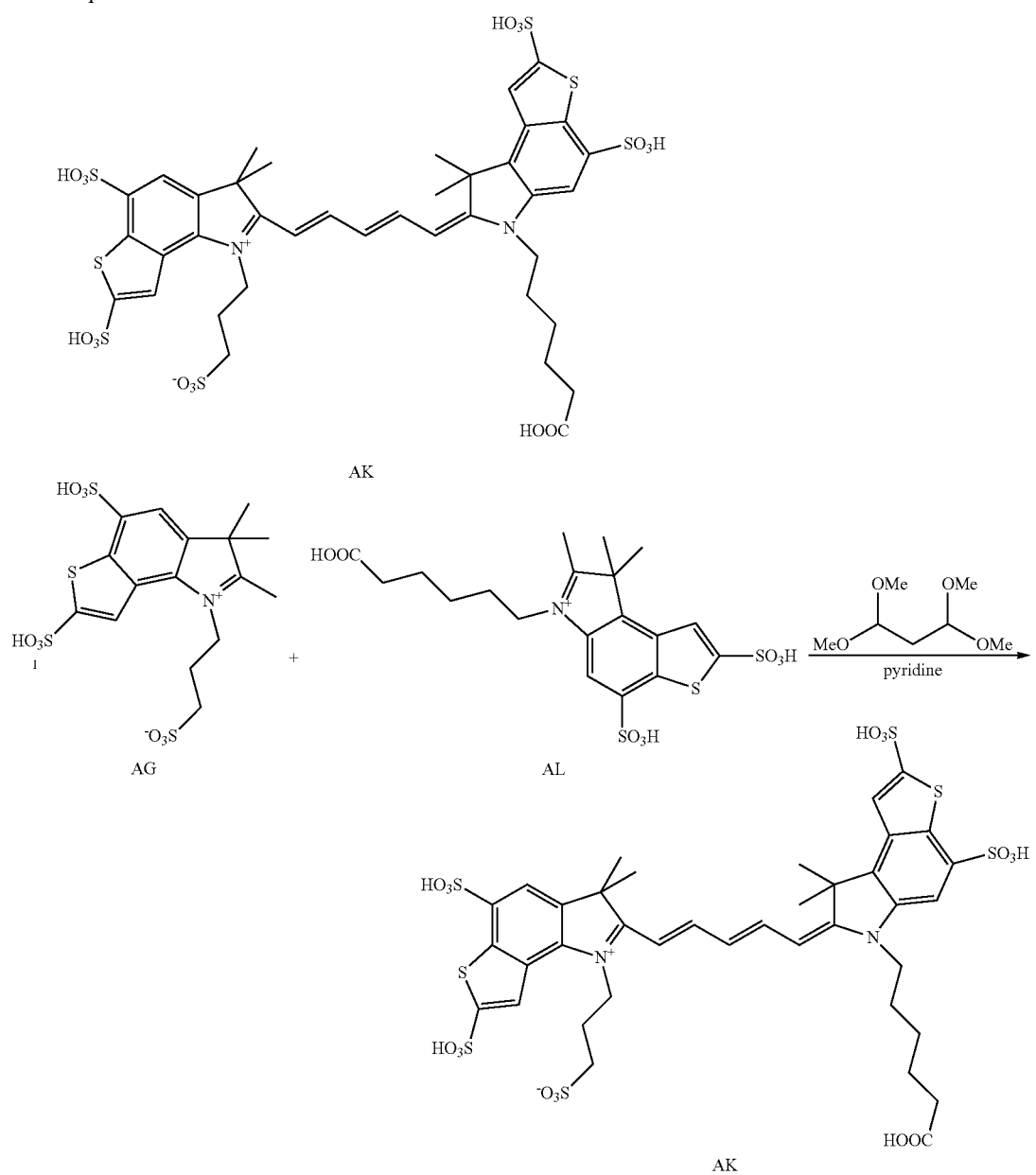
The compound was prepared by heating U and AG with 1,1,3,3-tetramethoxypropane in pyridine.
Synthesis of AT and AU
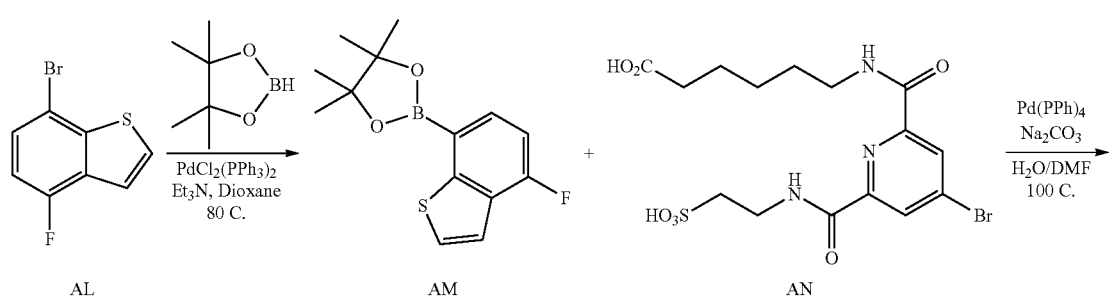

-continued
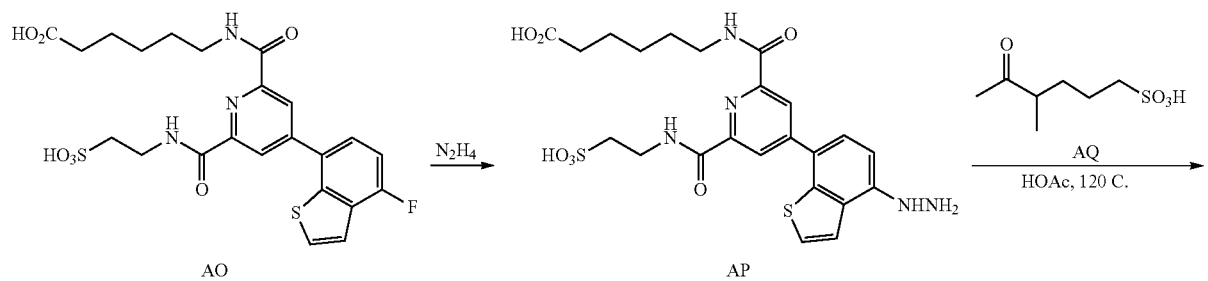
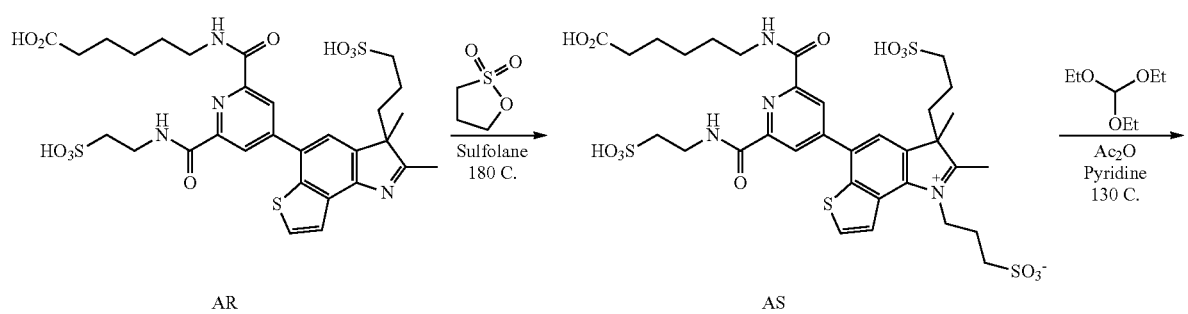
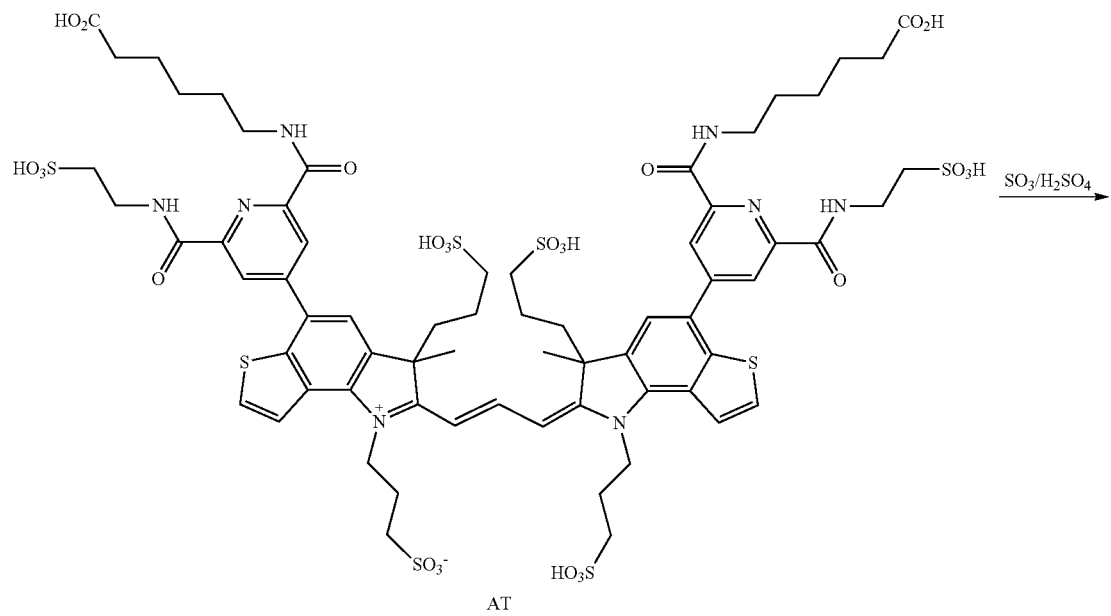

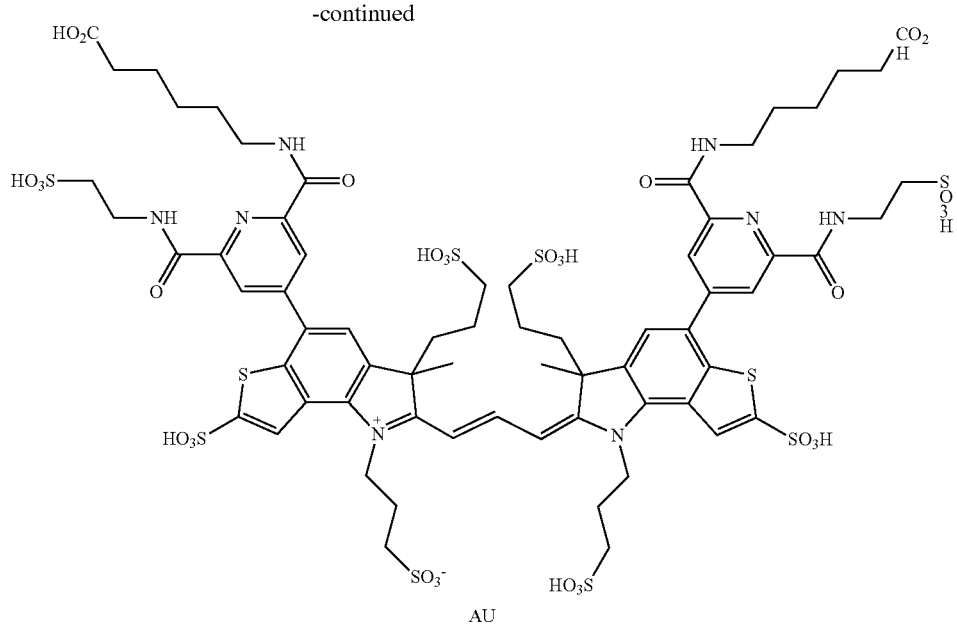

AU

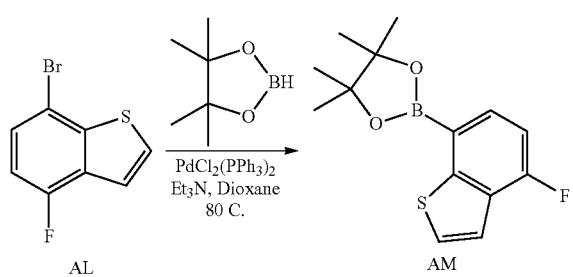

Synthesis of 2-(4-fluoro-1-benzothiophen-7-yl)-4,4,5,5-tetramethyl-1,3,2-dioxaborolane AM: 4,4,5,5-Tetramethyl-1,3,2-dioxaborolane (768 mg, 6 mmole) was added drop wise to a solution of 7-bromo-4-fluoro-1-benzothiophene AL (462 mg, 2.0 mmole) and triethylamine (607 mg, 6 mmole) in 12 mL dioxane. The solution was bubbling with argon with stirring for 10 min. PdCl$_2$(PPh$_3$)$_2$ (70 mg, 0.01 mmole) was added to the reaction and continued to bubbling argon for another 10 min. The reaction was heated to 80° C. for 4 hr and cooled down to 25° C. Dioxane was removed in vacuo the residue dissolved in 60 mL Et$_2$O washed with water (60 mL), brine (20 mL), dried (Na$_2$SO$_4$), filtered, concentrated in vacuo, and purified by CombiFlash silica gel column chromatography (eluted with Hexane/EtOAc stepping gradient 100:0 to 80:20) to yield 295 mg (53%) of product.

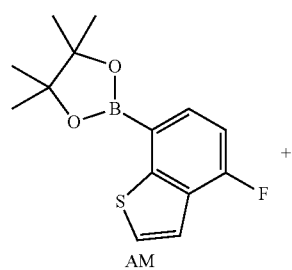

+

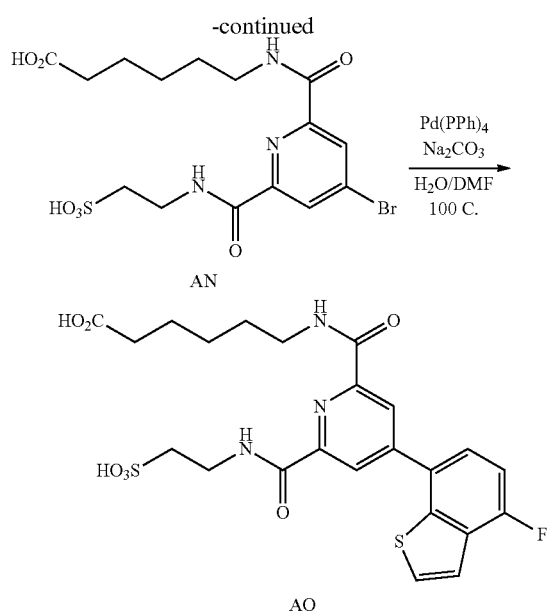

Synthesis of 6-{[4-(4-fluoro-1-benzothiophen-7-yl)-6-[(2-sulfoethyl)carbamoyl]pyridin-2-yl]formamido}hexanoic acid AO: A solution of Na$_2$CO$_3$ (560 mg, 5.3 mmol) in 4 mL water was added dropwise with stirring to a solution of AM (295 mg, 1.06 mmole) and AN (568 mg, 1.20 mmole) in 7 mL DMF. The solution was bubbling with argon with stirring for 10 min. Pd(PPh$_3$)$_4$ (77 mg, 0.066 mmole) was added to the reaction and continued to bubbling argon for another 10 min. The reaction was heated to 100° C. for 2 hr and cooled down to 25° C. Solvent was removed in vacuo the residue dissolved in 10 mL 0.1 N TEAB buffer (pH 7) and purified by reverse phase HPLC eluted with a gradient of CH$_3$CN over 0.1 N TEAB buffer. The yield of the desired product AO was 337 mg (43%).

hexanoic acid AP: Anhydrous hydrazine (26 mg, 0.80 mmole) was added to a solution of AO (303 mg, 0.40 mmole) in 3 mL sulfolane. The reaction was heated to 180° C. for 1 hr and cooled down to 25° C. The reaction was diluted with 10 mL 0.1 N TEAB buffer (pH 7) and purified by reverse phase HPLC eluted with a gradient of CH$_3$CN over 0.1 N TEAB buffer. The yield of the desired product AP was 128 mg (42%).

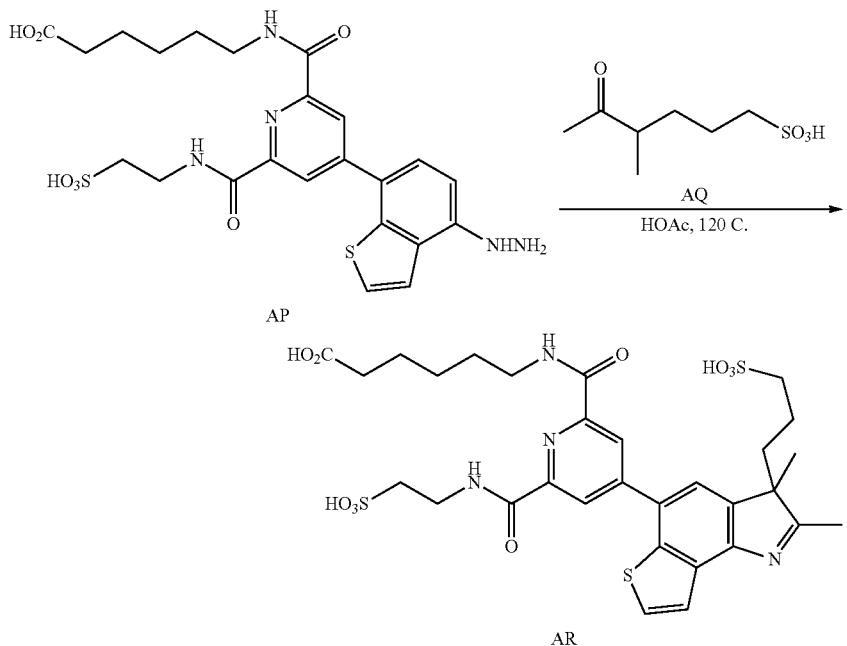

Synthesis of 6-({4-[2,3-dimethyl-3-(3-sulfopropyl)-3H-thieno[2,3-g]indol-5-yl]-6-[(2-sulfoethyl)carbamoyl]pyridin-2-yl}formamido)hexanoic acid AR: A solution of AP (128 mg, 0.17 mmole) and AQ (127 mg, 0.7 mmole) in 7 mL HOAc was heated at 120° C. for 1.4 hr and cooled down to 25° C. HOAc was removed in vacuo the residue dissolved in 10 mL 0.1 N TEAB buffer (pH 7) and purified by reverse phase HPLC eluted with a gradient of CH$_3$CN over 0.1 N TEAB buffer. The yield of the desired product AR was 124 mg (72%).

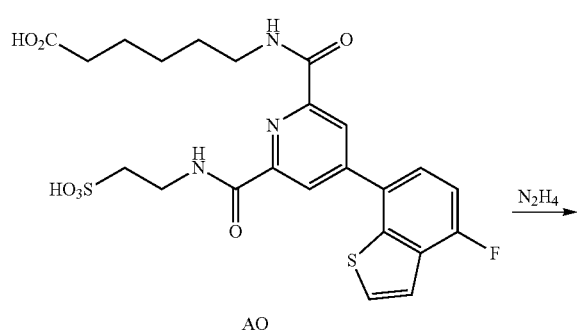

Synthesis of 6-{[4-(4-hydrazinyl-1-benzothiophen-7-yl)-6-[(2-sulfoethyl)carbamoyl]pyridin-2-yl]formamido}

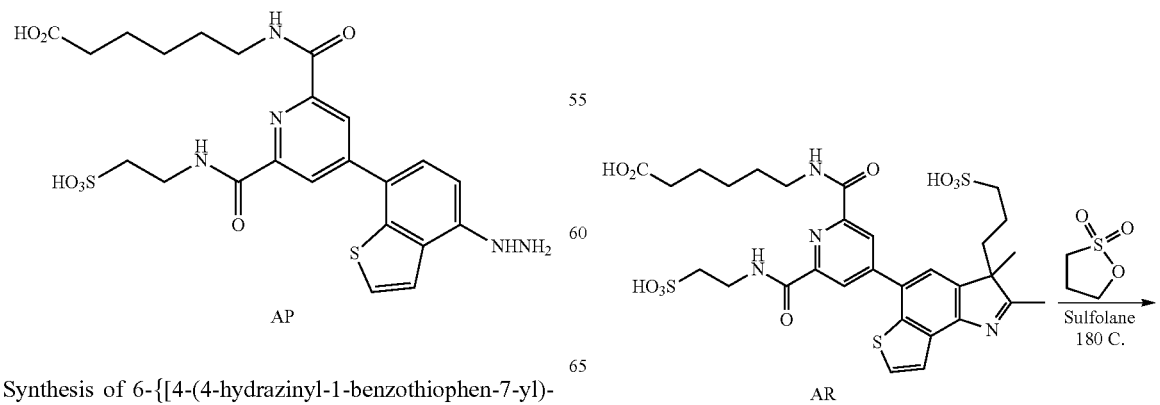

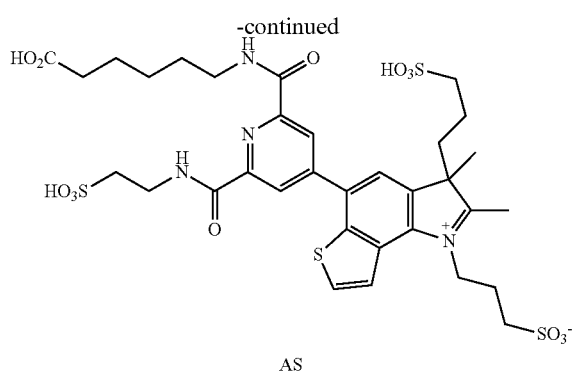

AS

Synthesis of 5-{2-[(5-carboxypentyl)carbamoyl]-6-[(2-sulfoethyl)carbamoyl]pyridin-4-yl}-2,3-dimethyl-1-(3-sulfonatopropyl)-3-(3-sulfopropyl)-3H-thieno[2,3-g]indol-1-ium AS: A solution of AR (124 mg, 0.11 mmole) and 1,3-propanesulfone (135 mg, 1.1 mmole) in 0.21 mL sulfolane was heated at 180° C. for 1 hr and cooled down to 25° C. The reaction was diluted with 0.33 mL 6 N HCl and heated to 70° C. for 1 hr and cooled down to 25° C. The solution was neutralized with 2N NaOH solution to pH 9. The product was purified by reverse phase HPLC eluted with a gradient of CH₃CN over 0.1 N TEAB buffer. The yield of the desired product AS was 62 mg (50%).

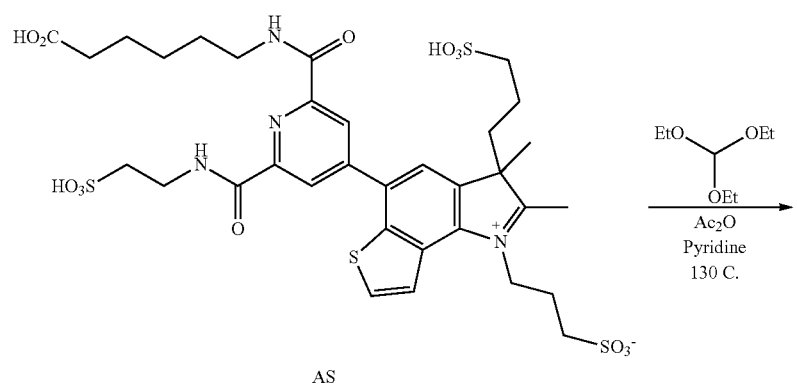

AS

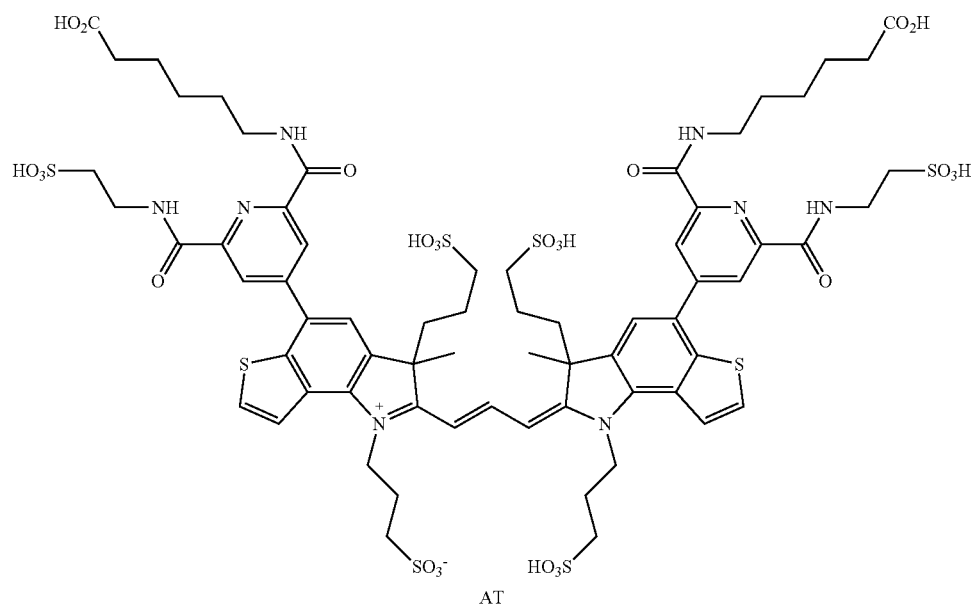

AT

Synthesis of AT: A solution of AS (62 mg, 54 umole), triethyl orthoformate (70 mg, 472 umole), and acetic anhydride (100 uL) in 300 uL of pyridine was heated at 130° C. for 10 min and cooled down to 25° C. Solvent was removed in vacuo and the residue dissolved in 3 mL 0.1 N $Na_2CO_3$ and purified by reverse phase HPLC eluted with a gradient of $CH_3CN$ over 0.1 N TEAB buffer. The yield of the desired product AT, as 1:1 stereoisomer, was 21 mg (33%).

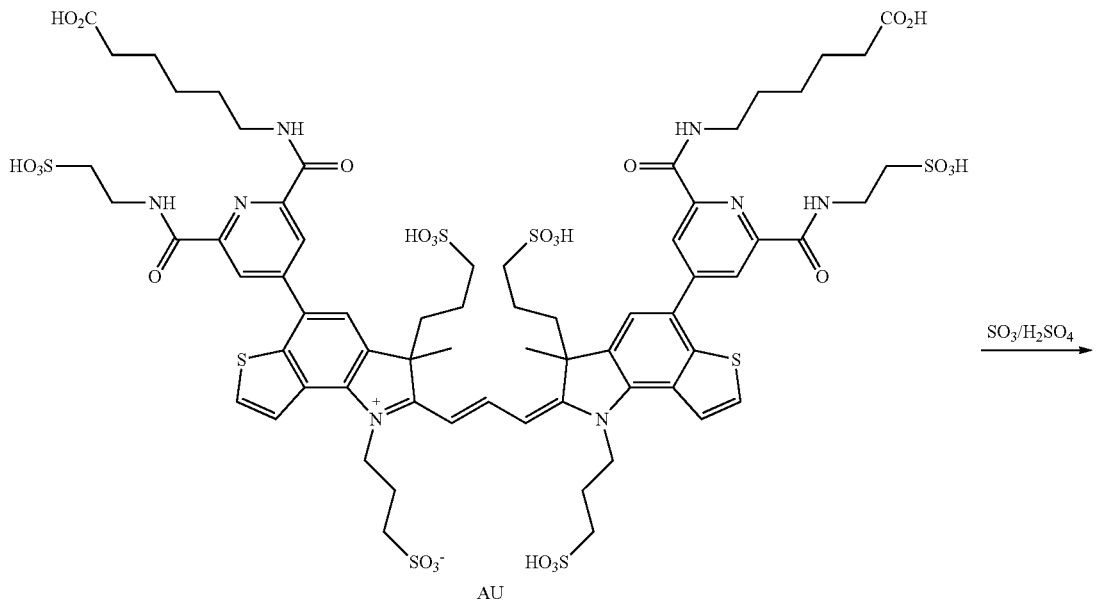

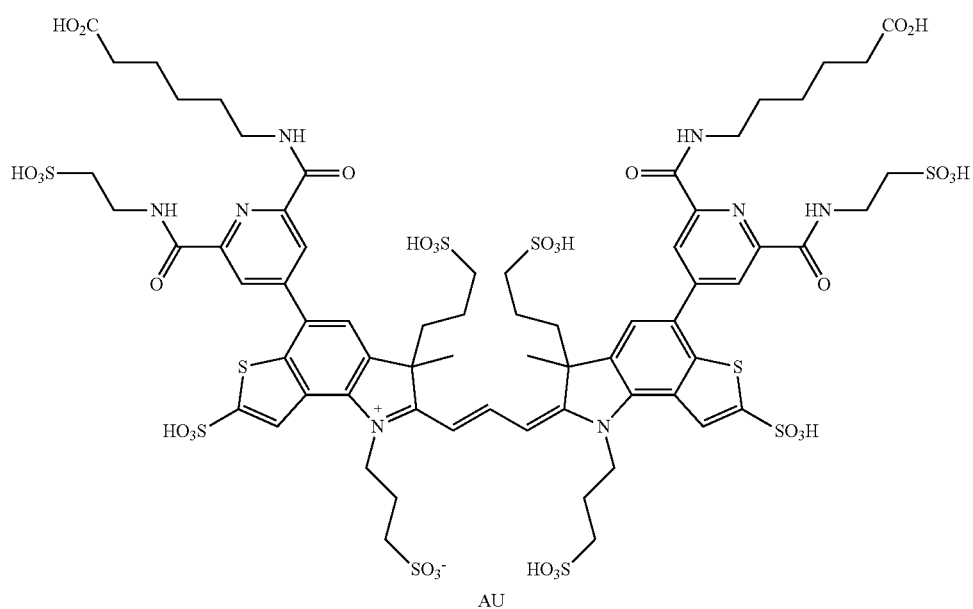

Synthesis of AU: Fuming sulfuric acid (20% SO$_3$, 200 uL) was added to AT (10 mg, 4.2 umole) the reaction was vortexed for 30 min. Ice was added to quench the reaction followed by addition of 6 N NaOH solution to bring the pH to 8. The product was purified by reverse phase HPLC eluted with a gradient of CH$_3$CN over 0.1 N TEAB buffer. The yield of the desired product AU was 6.6 mg (64%).
Synthesis of BA and BB
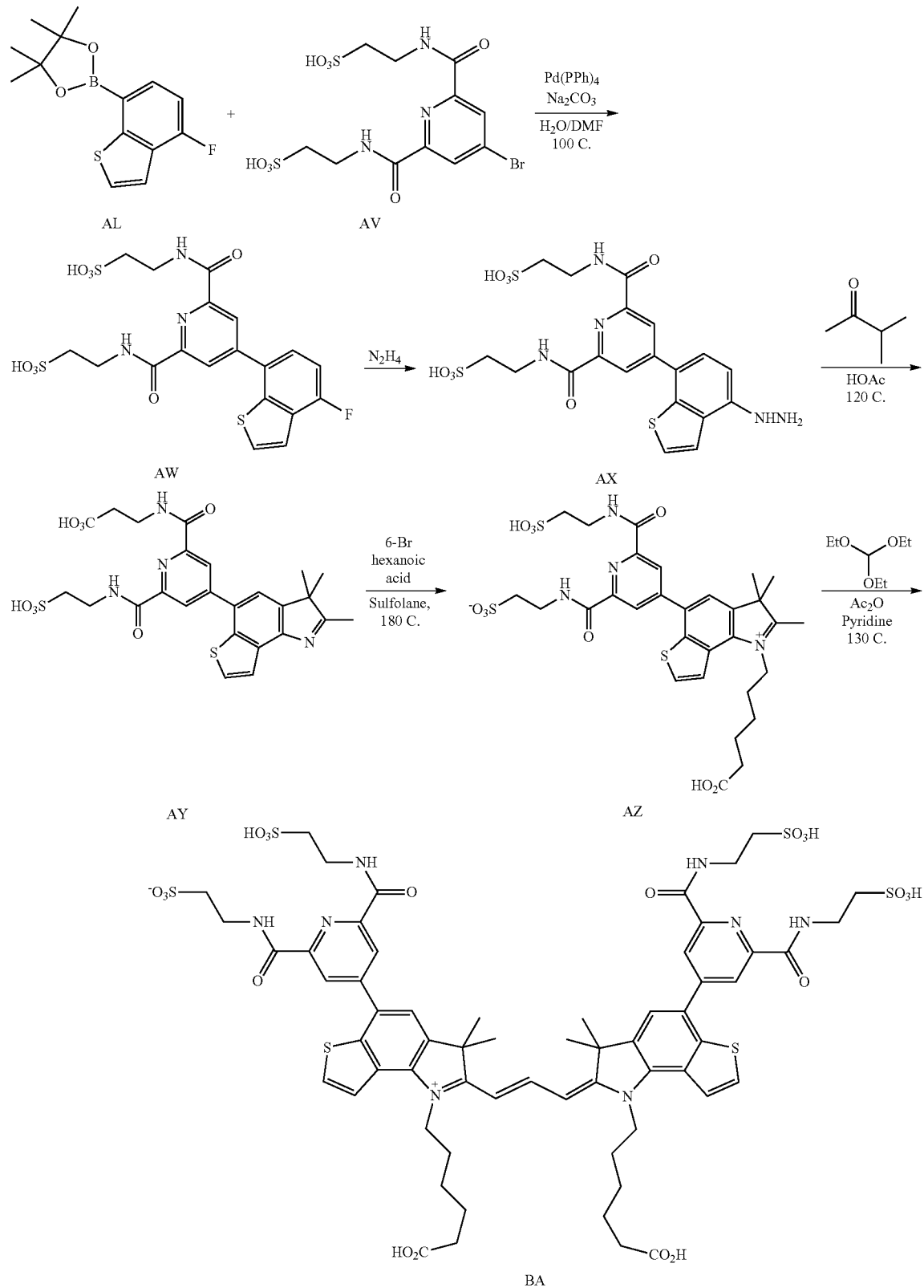

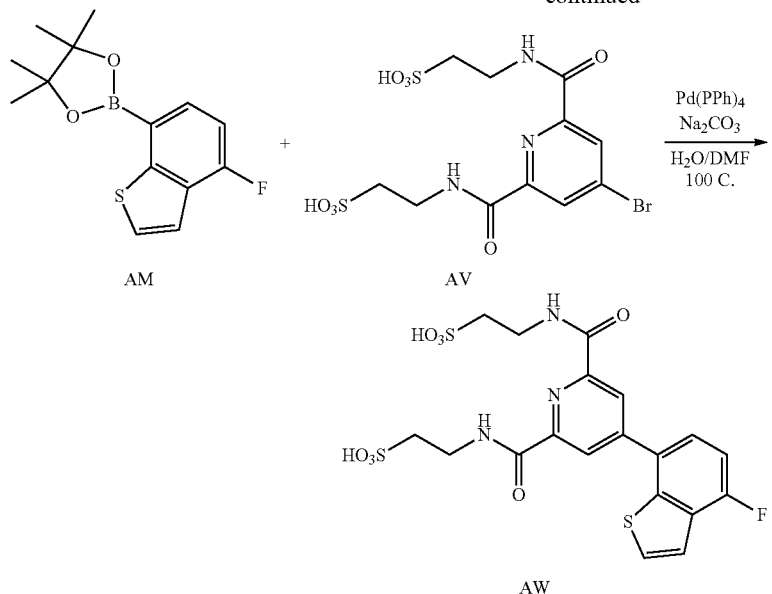

Synthesis of 2-{[4-(4-fluoro-1-benzothiophen-7-yl)-6-[(2-sulfoethyl)carbamoyl]pyridin-2-yl]formamido}ethane-1-sulfonic acid AW: A solution of Na₂CO₃ (6600 mg, 6.2 mmol) in 6 mL water was added dropwise with stirring to a solution of AM (347 mg, 1.24 mmole) and AV (1.15 g, 1.72 mmole) in 11 mL DMF. The solution was bubbling with argon with stirring for 10 min. Pd(PPh₃)₄ (88 mg, 0.076 mmole) was added to the reaction and continued to bubbling argon for another 10 min. The reaction was heated to 100° C. for 2 hr and cooled down to 25° C. Solvent was removed in vacuo the residue dissolved in 10 mL 0.1 N TEAB buffer (pH 7) and purified by reverse phase HPLC eluted with a gradient of CH₃CN over 0.1 N TEAB buffer. The yield of the desired product AW was 445 mg (49%).

Synthesis 2-{[4-(4-hydrazinyl-1-benzothiophen-7-yl)-6-[(2-sulfoethyl)carbamoyl]pyridin-2-yl]formamido}ethane-1-sulfonic acid AX: Anhydrous hydrazine (30 mg, 0.93 mmole) was added to a solution of AW (342 mg, 0.47 mmole) in 5 mL sulfolane. The reaction was heated to 180° C. for 1 hr and cooled down to 25° C. The reaction was diluted with 10 mL 0.1 N TEAB buffer (pH 7) and purified by reverse phase HPLC eluted with a gradient of CH₃CN over 0.1 N TEAB buffer. The yield of the desired product AX was 136 mg (39%).

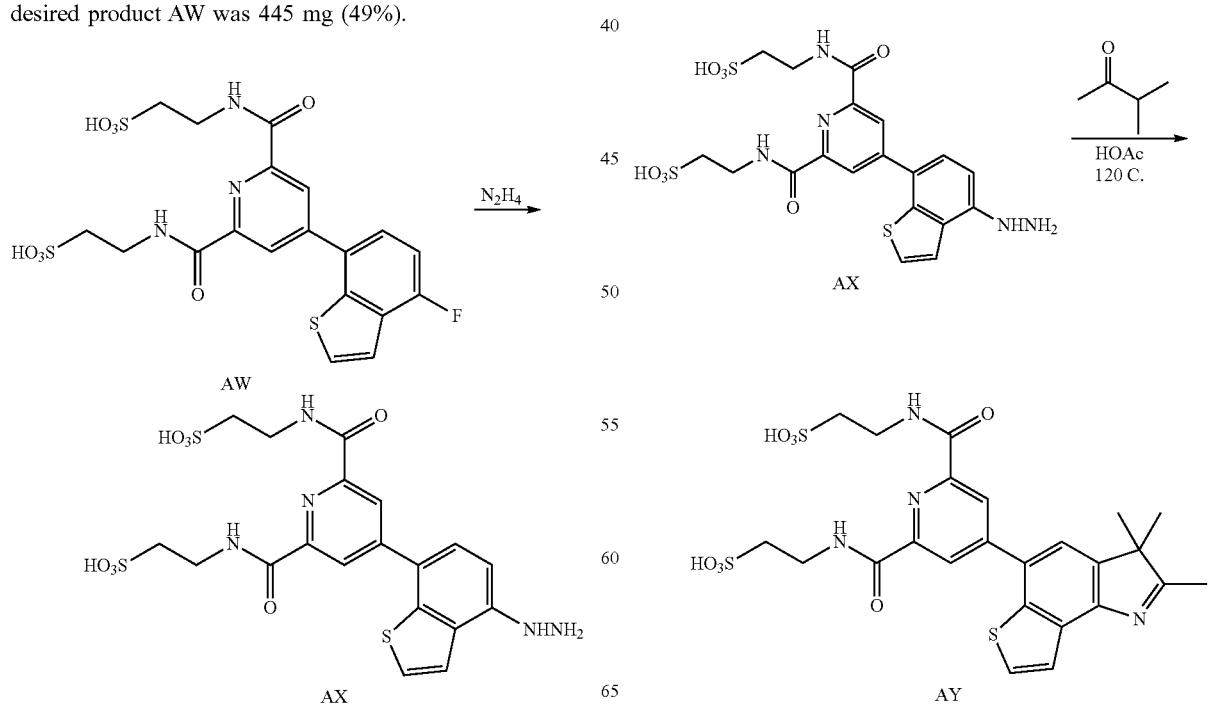

Synthesis of 2-({6-[(2-sulfoethyl)carbamoyl]-4-{2,3,3-trimethyl-3H-thieno[2,3-g]indol-5-yl}pyridin-2-yl}formamido)ethane-1-sulfonic acid AY: A solution of AX (70 mg, 94 umole) and methyl isopropyl ketone (450 mg, 5.2 mmole) in 5 mL HOAc was heated at 120° C. for 1 hr and cooled down to 25° C. HOAc was removed in vacuo the residue dissolved in 10 mL 0.1 N TEAB buffer (pH 7) and purified by reverse phase HPLC eluted with a gradient of CH$_3$CN over 0.1 N TEAB buffer. The yield of the desired product AY was 58 mg (77%).

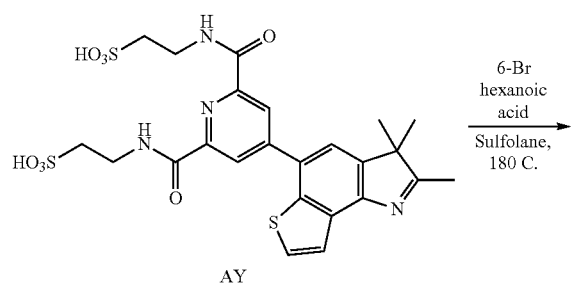

AY

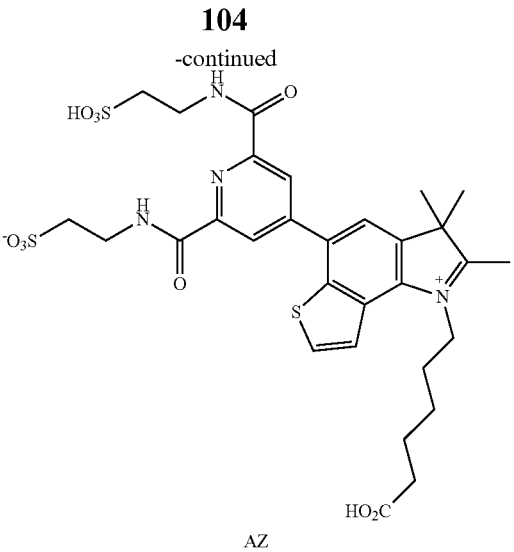

AZ

Synthesis of 1-(5-carboxypentyl)-2,3,3-trimethyl-5-{2-[(2-sulfoethyl)carbamoyl]-6-[(2-sulfonatoethyl)carbamoyl]pyridin-4-yl}-3H-thieno[2,3-g]indol-1-ium AZ: A solution of AY (58 mg, 73 umole) and 6-bromohexanoic acid (280 mg, 1.4 mmole) in 0.2 mL sulfolane was heated at 180° C. for 1 hr and cooled down to 25° C. The reaction was diluted with 0.3 mL 6 N HCl and heated to 70° C. for 1 hr and cooled down to 25° C. The solution was neutralized with 2N NaOH solution to pH 9. The product was purified by reverse phase HPLC eluted with a gradient of CH$_3$CN over 0.1 N TEAB buffer. The yield of the desired product AZ was 7.3 mg (11%).

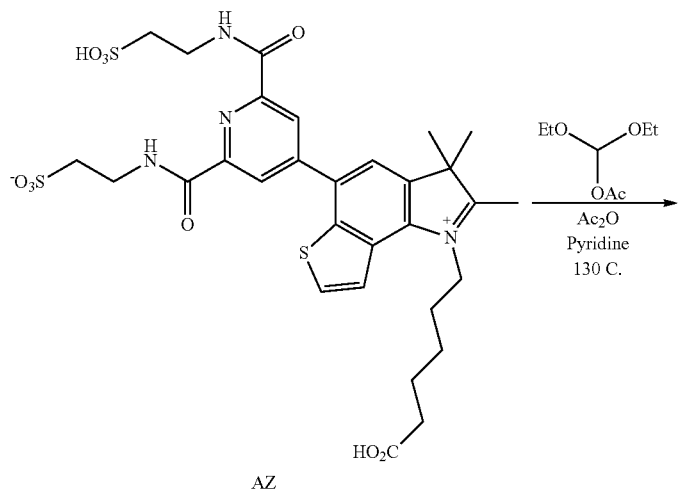

AZ

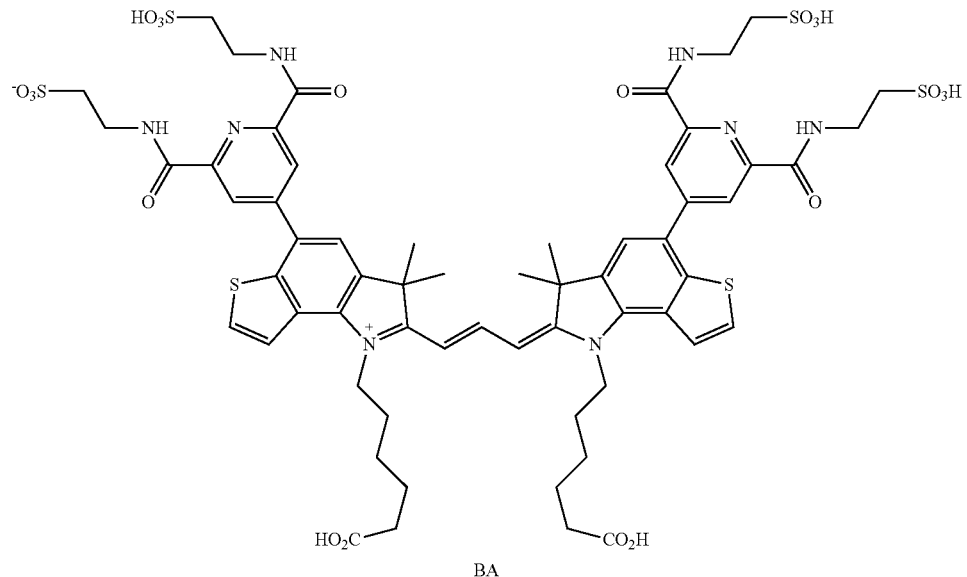
Synthesis of BA: A solution of AZ (7.3 mg, 8.0 umole), diethoxymethyl acetate (14 mg, 86 umole), and acetic anhydride (70 uL) in 200 uL of pyridine was heated at 130° C. for 10 min and cooled down to 25° C. Solvent was removed in vacuo and the residue dissolved in 3 mL 0.1 N $Na_2CO_3$ and purified by reverse phase HPLC eluted with a gradient of $CH_3CN$ over 0.1 N TEAB buffer. The yield of the desired product BA was 2.0 mg (26%).
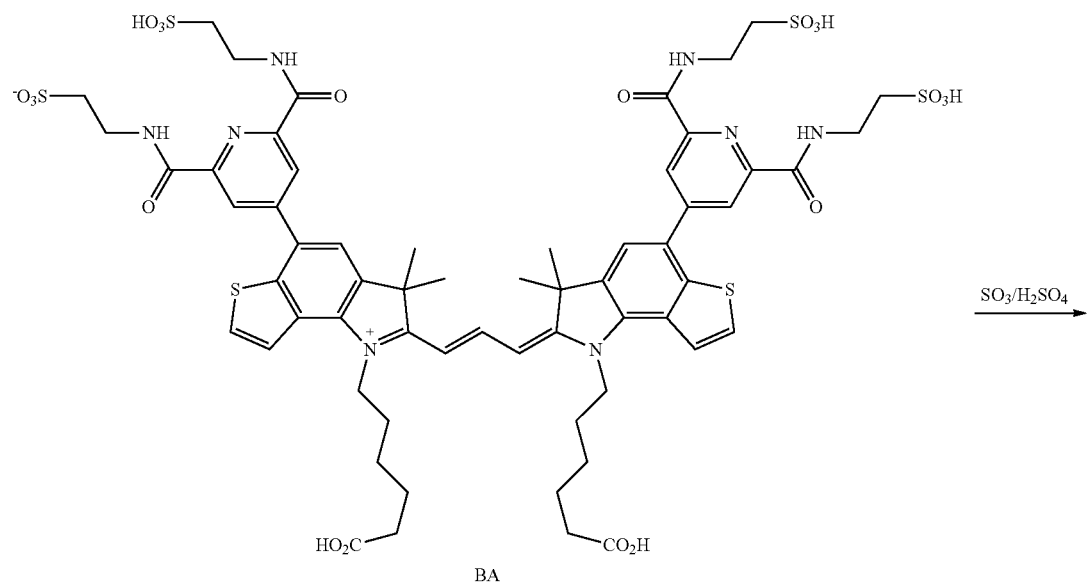

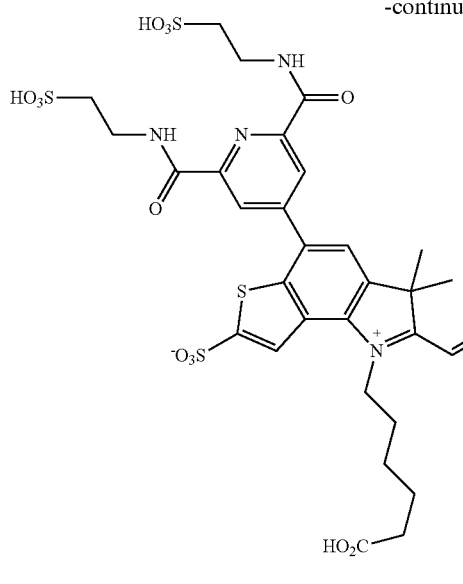
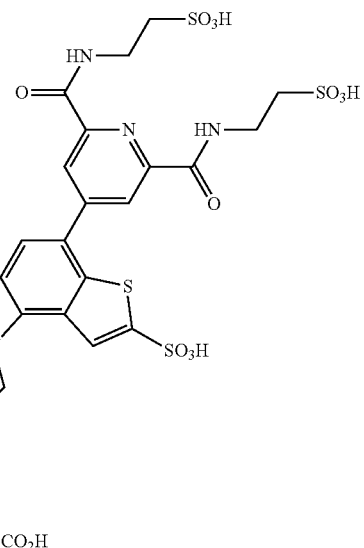
BB
Synthesis of BB: Fuming sulfuric acid (20% $SO_3$, 100 uL) was added to BA (2.0 mg, 1.0 umole) the reaction was vortexed for 30 min. Ice was added to quench the reaction followed by addition of 6 N NaOH solution to bring the pH to 8. The product was purified by reverse phase HPLC eluted with a gradient of $CH_3CN$ over 0.1 N TEAB buffer. The yield of the desired product BB was 1.3 mg (58%).
Synthesis of BG
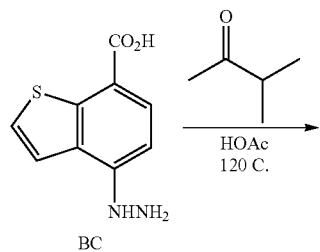
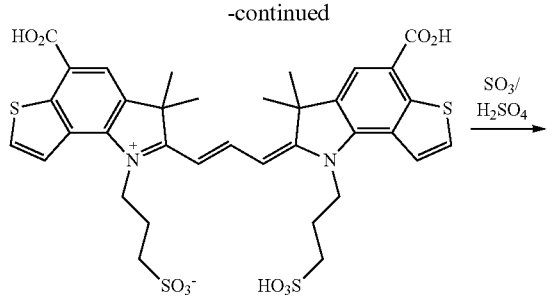
BF
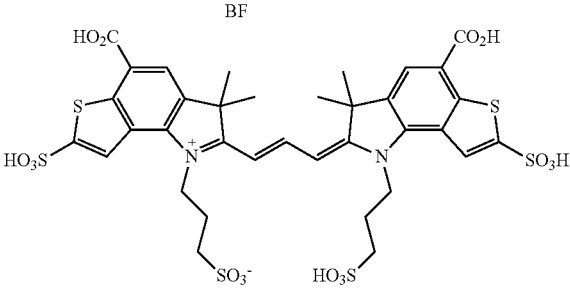
BG
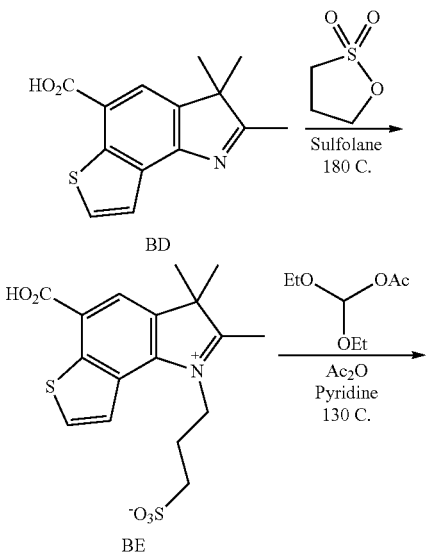
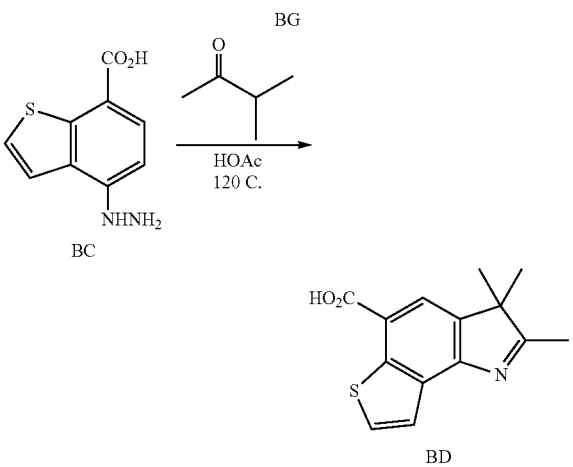

Synthesis of 2,3,3-trimethyl-3H-thieno[2,3-g]indole-5-carboxylic acid BD: A solution of 4-hydrazinyl-1-benzothiophene-7-carboxylic acid BC (208 mg, 1.0 mmole) and methyl isopropyl ketone (457 mg, 5.3 mmole) in 5 mL HOAc was heated at 120° C. for 1.5 hr and cooled down to 25° C. HOAc was removed in vacuo the product was purified with CombiFlash silica gel column chromatography (eluted with CH$_2$Cl$_2$/MeOH stepping gradient 100:0 to 80:20). The yield of the desired product BD was 210 mg (81%).

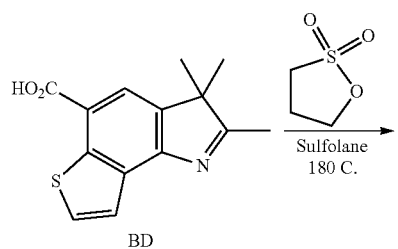

Synthesis of 5-carboxy-2,3,3-trimethyl-1-(3-sulfonatopropyl)-3H-thieno[2,3-g]indol-1-ium BE: A solution of BD (210 mg, 0.81 mmole) and 1,3-propanesulfone (530 mg, 4.3 mmole) in 0.4 mL sulfolane was heated at 180° C. for 1 hr and cooled down to 25° C. The reaction was diluted with 0.5 mL 6 N HCl and heated to 80° C. for 1 hr and cooled down to 25° C. The solution was neutralized with 2N NaOH solution to pH 9. The product was purified by reverse phase HPLC eluted with a gradient of CH$_3$CN over 0.1 N TEAB buffer. The yield of the desired product BE was 172 mg (44%).

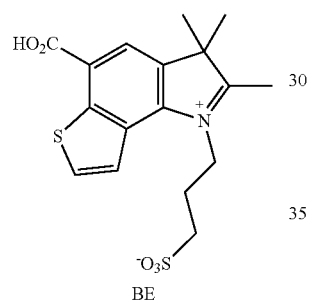

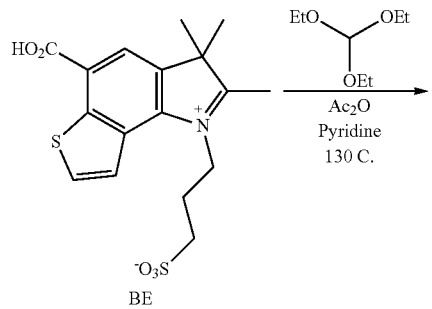

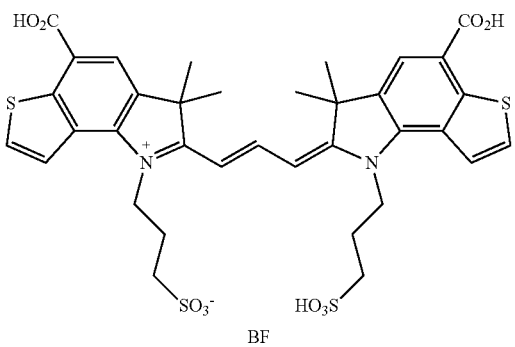

Synthesis of 5-carboxy-2-[(1E)-3-[(2E)-5-carboxy-3,3-dimethyl-1-(3-sulfopropyl)thieno[2,3-g]indol-2-ylidene]prop-1-en-1-yl]-3,3-dimethyl-1-(3-sulfonatopropyl)thieno[2,3-g]indol-1-ium BF: A solution of FE (172 mg, 0.36 mmole), diethoxymethyl acetate (200 mg, 1.23 mmole), and acetic anhydride (330 uL) in 700 uL of pyridine was heated at 130° C. for 10 min and cooled down to 25° C. Solvent was removed in vacuo and the residue dissolved in 10 mL 0.1 N Na$_2$CO$_3$ and purified by reverse phase HPLC eluted with a gradient of CH$_3$CN over 0.1 N TEAB buffer. The yield of the desired product BF was 47 mg (30%).

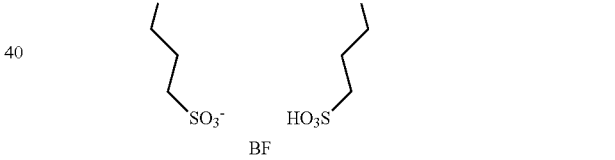

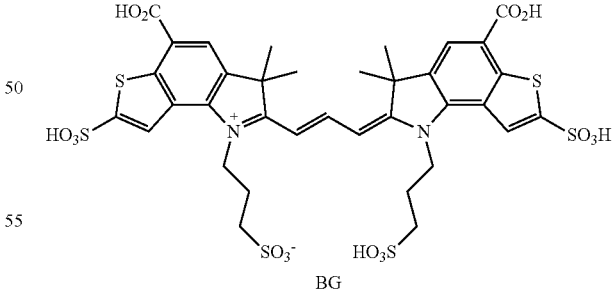

Synthesis of BG: Fuming sulfuric acid (20% SO$_3$, 300 uL) was added to BF (20 mg, 18.6 umole) the reaction was vortexed for 1 hr. Ice was added to quench the reaction followed by addition of 6 N NaOH solution to bring the pH to 8. The product was purified by reverse phase HPLC eluted with a gradient of CH$_3$CN over 0.1 N TEAB buffer. The yield of the desired product BG was 14.2 mg (53%).

Preparation of BK

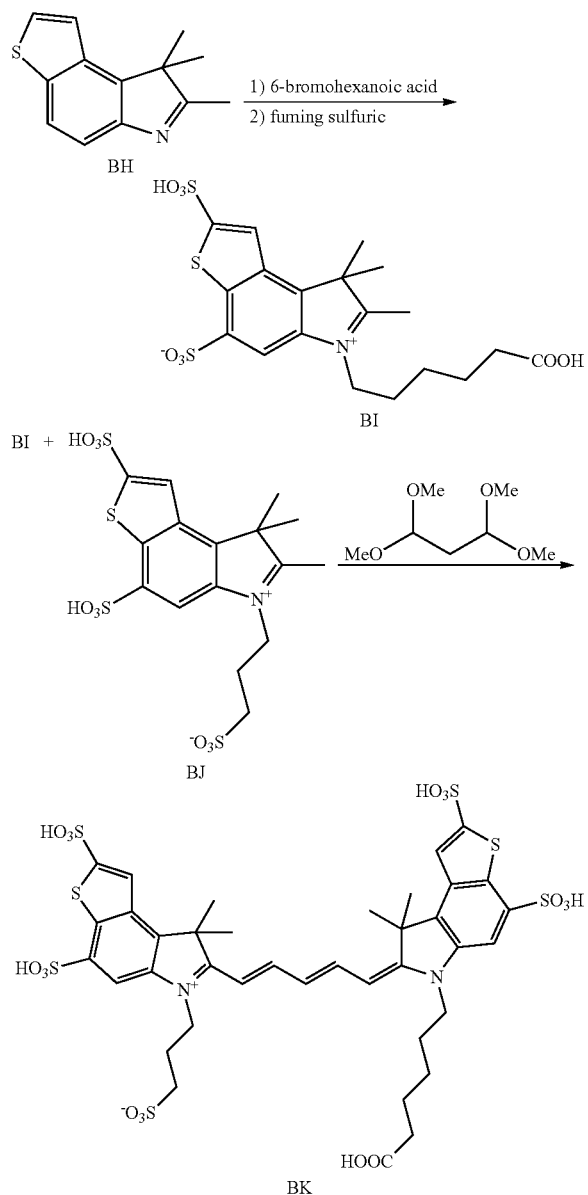

Intermediate BH (26 mg) was alkylated with 6-bromohexanoic acid followed by treatment with fuming sulfuric acid to obtain BI which was then heated with 20 mg of BJ (prepared in a similar fashion), 100 μL of 1,1,3,3-tetramethoxypropane, 0.2 mL of pyridine in 0.4 mL of DMF at 110° C. for 1 hour. The crude reaction mixture was pumped and then stirred in 1 mL of 0.5 M KOH at room temperature overnight. The crude was purified by HPLC to yield 3.2 mg of the desired product BK.

The present invention provides, inter alia, novel cyanine dyes, conjugates incorporating these dyes and method of using the dyes and conjugates. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A fluorescent compound or conjugate having the formula:

A-Q-B wherein

Q has a formula which is a member selected from:

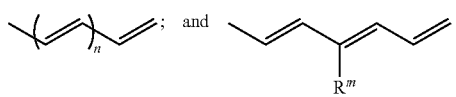

n is 1, 2 or 3;

$R^m$ is a member selected from:

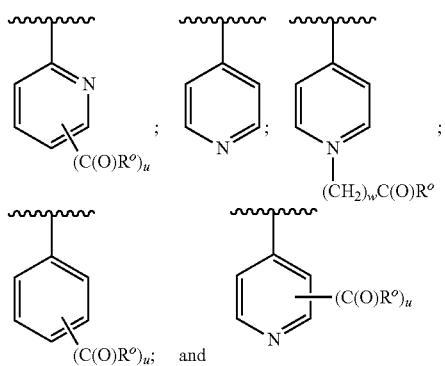

wherein w is an integer from 1 to 10;

u is 0, 1, 2, 3, 4, or 5 and, when u is two or greater, each $R^o$ is independently selected;

$R^o$ is a member selected from OH, O$^-$, a reactive functional group, a component of a reactive functional group and a linkage fragment binding the compound to a carrier molecule;

B is a moiety which is a member selected from Formulae I, II and III;

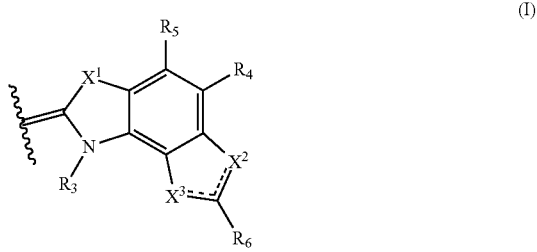

-continued

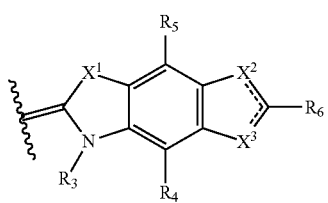
(II)

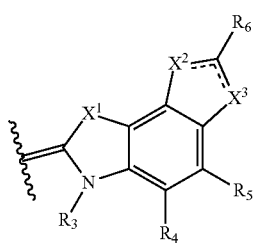
(III)

wherein
X¹ is CR¹R²,
wherein
R¹, R² and R³ are independently CH₂R⁷;
X² and X³ are members independently selected from O, S, N, NH, CR²², and CR²²R²³,
wherein
R⁴, R⁵, R⁶, R⁷, R²² and R²³ are members independently selected from H, R²⁸, R²⁸Z², SO₃H, CO₂H, R²⁸SO₃H, C(O)NHR²⁸SO₃H, CONHR²⁸C(O)Z²,

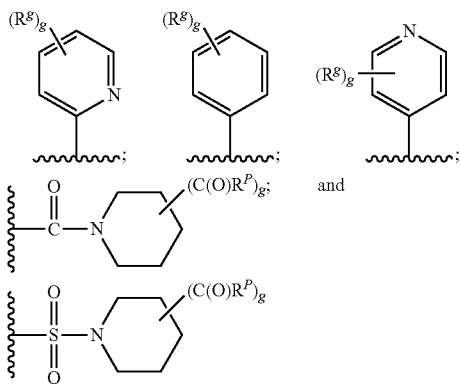

wherein
R$^p$ and Z² are independently selected from OH, O⁻, a reactive functional group, a component of a reactive functional group and a linkage fragment covalently binding said compound to a carrier molecule;
g is an integer selected from 0, 1, 2, 3, and 4, and when g is greater than or equal to 2, each R$^g$ or R$^p$ is independently selected;
R$^g$ is a member selected from H, R³⁸, R³⁸Z³, SO₃H, CO₂H, R³⁸SO₃H, CONHR³⁸SO₃H, and CONHR³⁸C(O)Z³,
wherein
R²⁸ and R³⁸ are independently selected from a bond, substituted or unsubstituted alkyl, substituted or unsubstituted heteroalkyl, substituted or unsubstituted aryl, substituted or unsubstituted heteroaryl and substituted or unsubstituted heterocycloalkyl;

Z³ is selected from OH, O⁻, a reactive functional group, a component of a reactive functional group and a linkage fragment covalently binding said compound to a carrier molecule;
at least one of R¹, R², R³, R⁴, R⁵ and R⁶ is a reactive functional group, a component of a reactive functional group or is a linkage fragment covalently binding said compound to a carrier molecule;
said compound comprises at least three SO₃H moieties; and
A has a formula which is a member selected from:

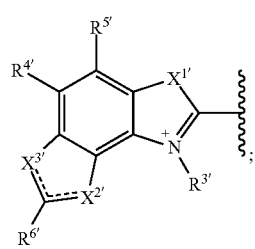
(IV)

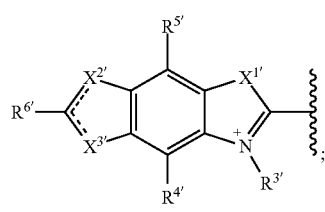
(V)

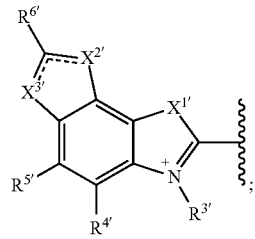
(VI)

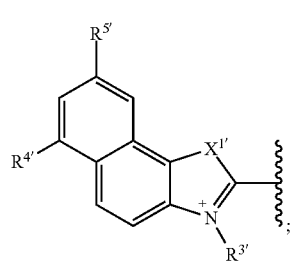
(VII)

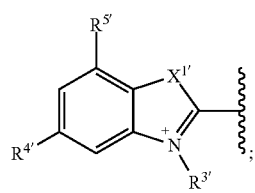
(VIII)

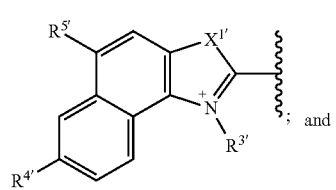
(IX)
; and

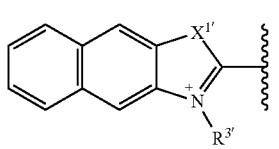
(X)

wherein
X[1'] is CR[1']R[2'],
wherein
R[1'], R[2'] and R[3'] are independently $CH_2R^{7'}$;
X[2'] and X[3'] are members independently selected from O, S, N, NH, CR[22'], and CR[22']R[23'],
wherein
R[4'], R[5'], R[6'], R[7'], R[22'] and R[23'] are members independently selected from H, R[28'], R[28']Z[2'], $SO_3H$, $CO_2H$, R[28']$SO_3H$, CONHR[28']$SO_3H$, CONHR[28']C(O)Z[2'],

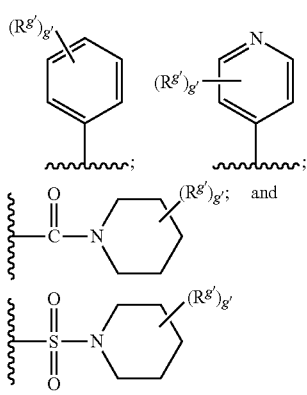

wherein
Z[2'] is a reactive functional group or is a linkage fragment covalently binding said compound to a carrier molecule;
g' is selected from 0, 1, 2, 3, 4 and 5, and when it is greater than or equal to 2, each R[g'] is independently selected;
R[g'] is a member selected from H, R[38'], R[38']Z[3'], $SO_3H$, $CO_2H$, R[38']$SO_3H$, CONHR[38']$SO_3H$, and CONHR[38']C(O)Z[3'],
wherein
R[28'] and R[38'] is a bond or is a member selected from substituted or unsubstituted alkyl, substituted or unsubstituted heteroalkyl, substituted or unsubstituted aryl, substituted or unsubstituted heteroaryl and substituted or unsubstituted heterocycloalkyl; and
Z[3'] is a member selected from a reactive functional group, a component of a reactive functional group and a linkage fragment covalently binding said compound to a carrier molecule.

2. The compound or conjugate according to claim 1, wherein at least one of X[3] and X[3'] is S.

3. The compound or conjugate according to claim 1, wherein at least one of X[2] and X[2'] is CH.

4. The compound or conjugate according to claim 1, wherein at least one of R[6] and R[6'] is $SO_3^-$.

5. The compound or conjugate according to claim 1, wherein X[2], X[2'], X[3] and X[3'] are members independently selected from O, S, N, NH, CH, $CH_2$ and $C(CH_3)_2$.

6. The compound or conjugate according to claim 5, wherein at least one member selected from X[2], X[2'], X[3] and X[3'] is selected from NH, O and S.

7. The compound or conjugate according to claim 1, wherein not more than one member selected from X[2], X[2'], X[3] and X[3'] is O.

8. The compound or conjugate according to claim 7, wherein none of X[2], X[2'], X[3] and X[3'] is O.

9. The compound or conjugate according to claim 1, having a formula which is a member selected from:

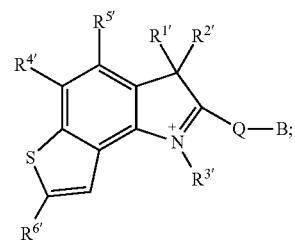

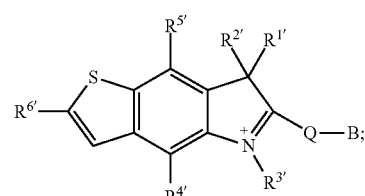

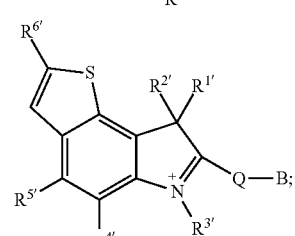

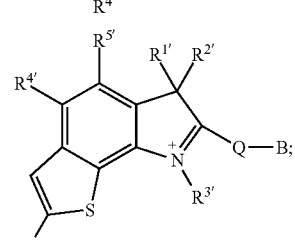

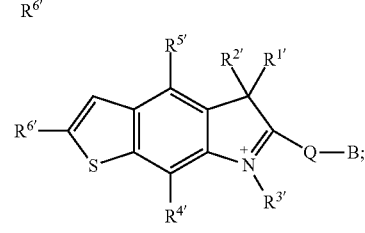

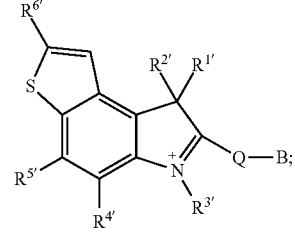

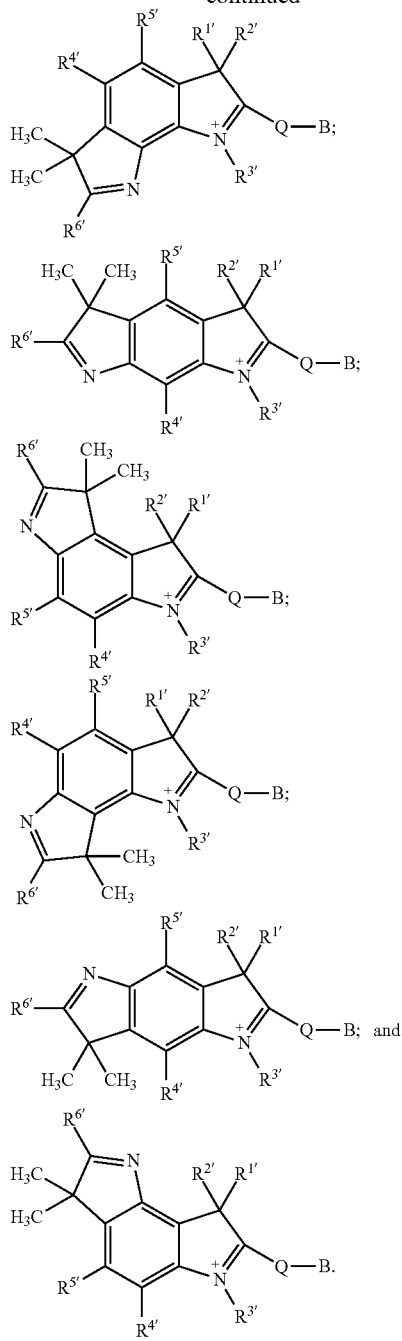
10. The compound or conjugate according to claim 1, having a formula selected from:
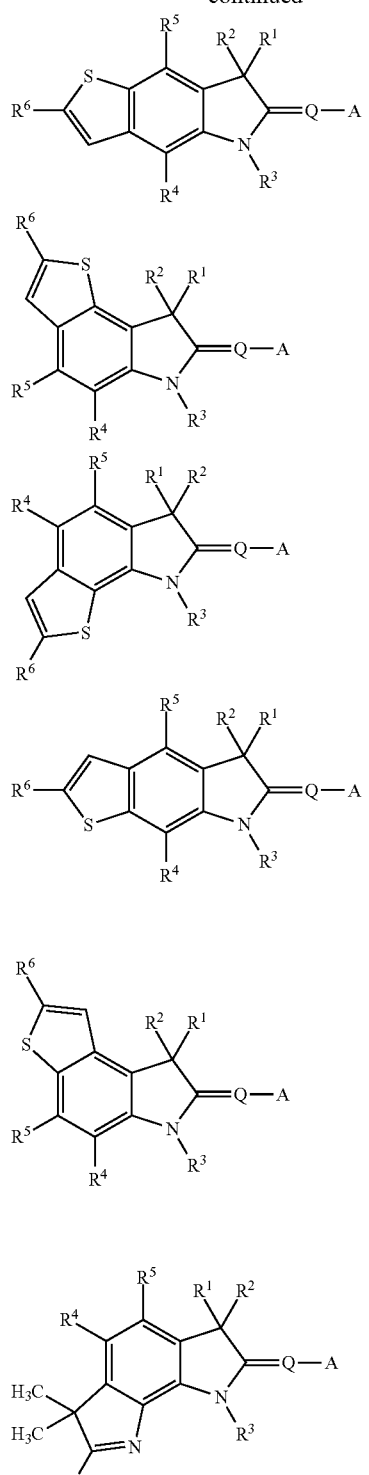
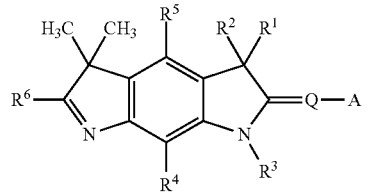

-continued
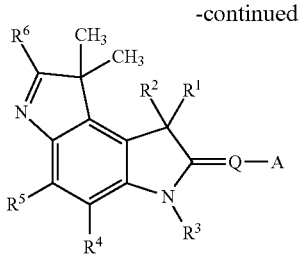
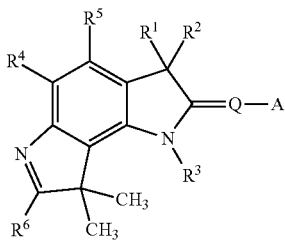
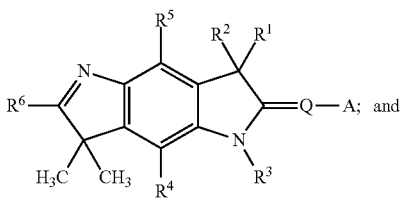
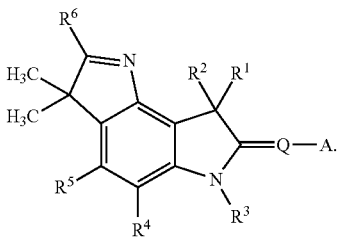
11. The compound or conjugate according to claim 1, having a formula which is a member selected from:
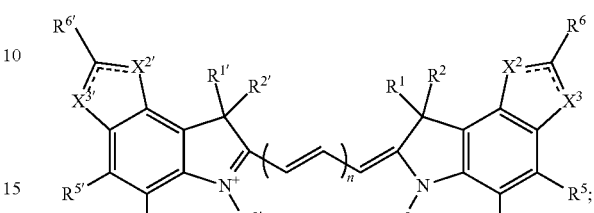
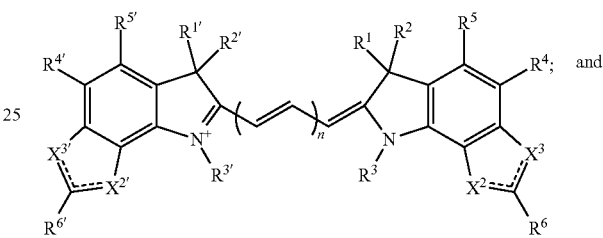
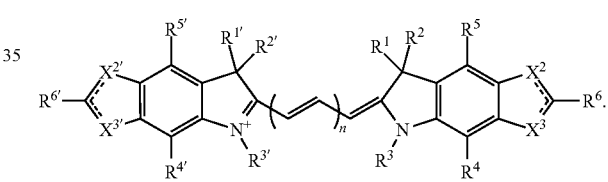
12. The compound or conjugate according to claim 1, having the formula:
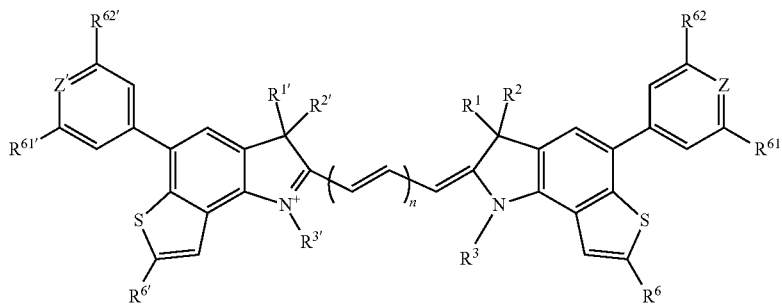

wherein
R⁶¹, R⁶¹', R⁶² and R⁶²' are members independently selected from H, CH₃, COOH, and NH(CH₂)₂SO₃H;
Z and Z' are members independently selected from N and CH; and
n is 1, 2 or 3.

13. The compound or conjugate according to claim 1, having the formula:

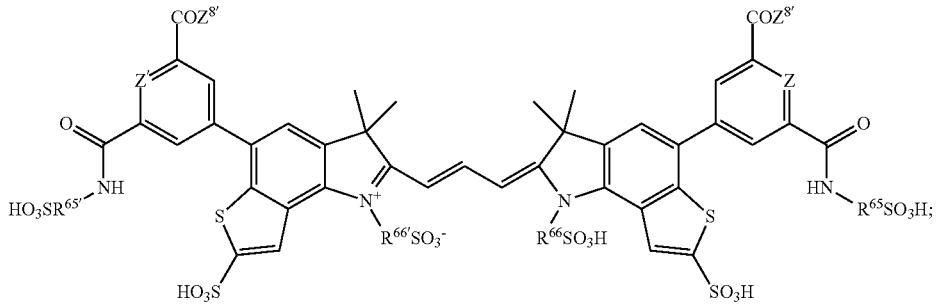

wherein
Z and Z' are members independently selected from N and CH;
Z⁸ and Z⁸' are members independently selected from N(Z⁷⁵)R⁷⁶C(O)Z¹², in which
R⁷⁵ is a member selected from H, substituted or unsubstituted alkyl and substituted or unsubstituted heteroalkyl;
R⁷⁶ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl; and
Z¹² is selected from OH, O⁻, a reactive functional group, a component of a reactive functional group and a linkage fragment covalently binding the compound to a carrier molecule; and
R⁶⁵, R⁶⁵', R⁶⁶ and R⁶⁶' are members independently selected from substituted or unsubstituted alkyl having from 2 to 6 carbon atoms.

14. The compound or conjugate according to claim 1, wherein R⁴, R⁵, R⁶, R⁷, R²² and R²³ are independently selected from:

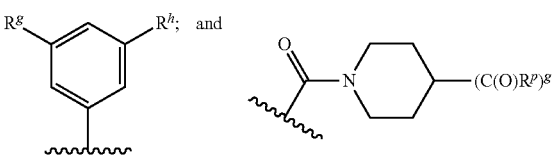

wherein
R^g and R^h are members independently selected from H, R³⁸, R³⁸Z³, SO₃H, CO₂H, R³⁸SO₃H, CONHR³⁸SO₃H, and CONHR³⁸CO₂H.

15. The compound or conjugate according to claim 1, having a formula selected from:

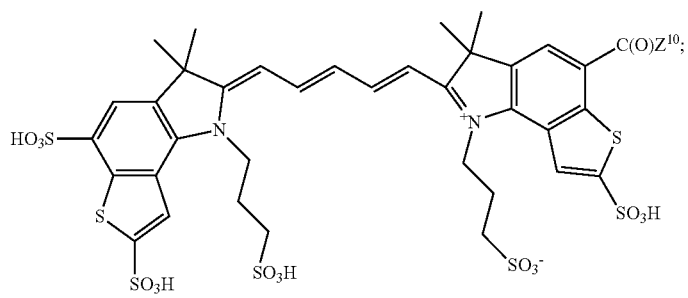

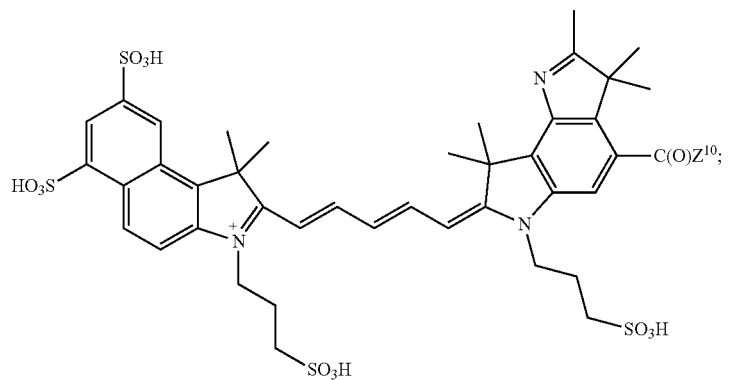
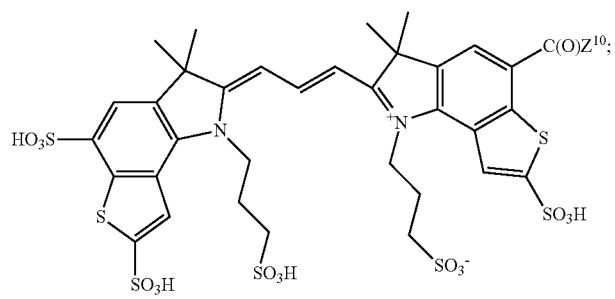
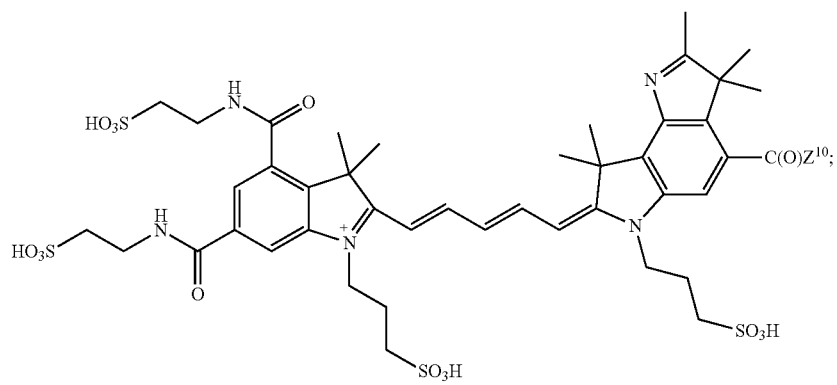
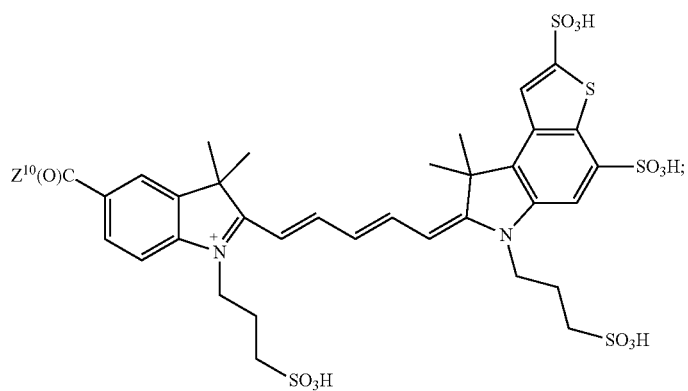

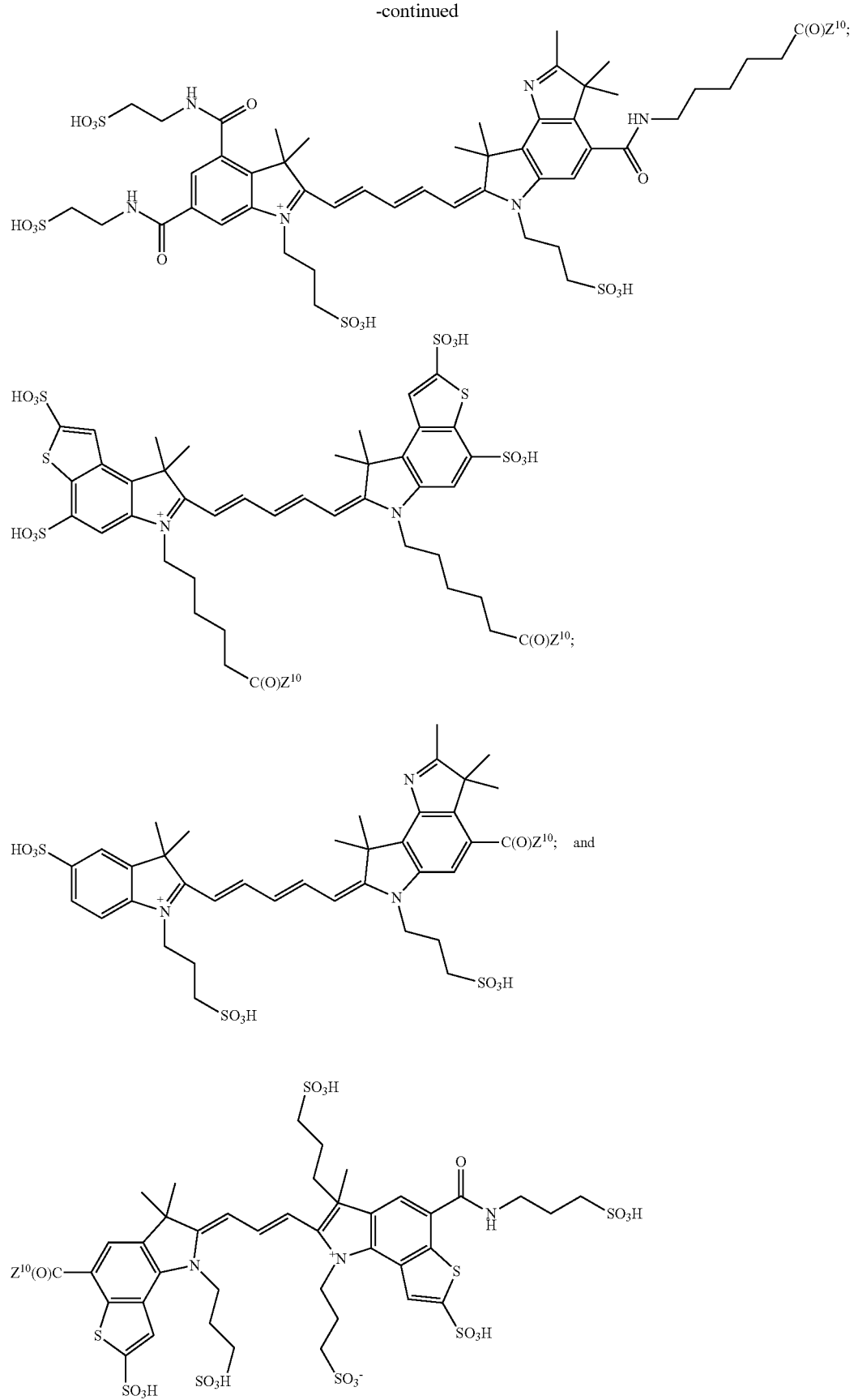

wherein

Z$^{10}$ is a member selected from said reactive functional group, said component of a reactive functional group or said linkage fragment covalently binding said compound to a carrier molecule, and when said compound includes more than one Z$^{10}$, each Z$^{10}$ is independently selected.

16. The compound or conjugate according to claim 1, wherein said reactive functional group is a member selected from an amine, a hydroxy, an aldehyde, a ketone, a hydroxylamine, a sulfhydryl, an isocyanate, an isothiocyanate, a haloacetamide, a hydrazine, an ester, an anhydride, an acyl azide, an acyl halide, a sulfonyl halide, a maleimide, a carbodiimide, a phosphoramidite, and an imidazole.

17. The compound or conjugate according to claim 1, wherein said reactive functional group is a member selected from:

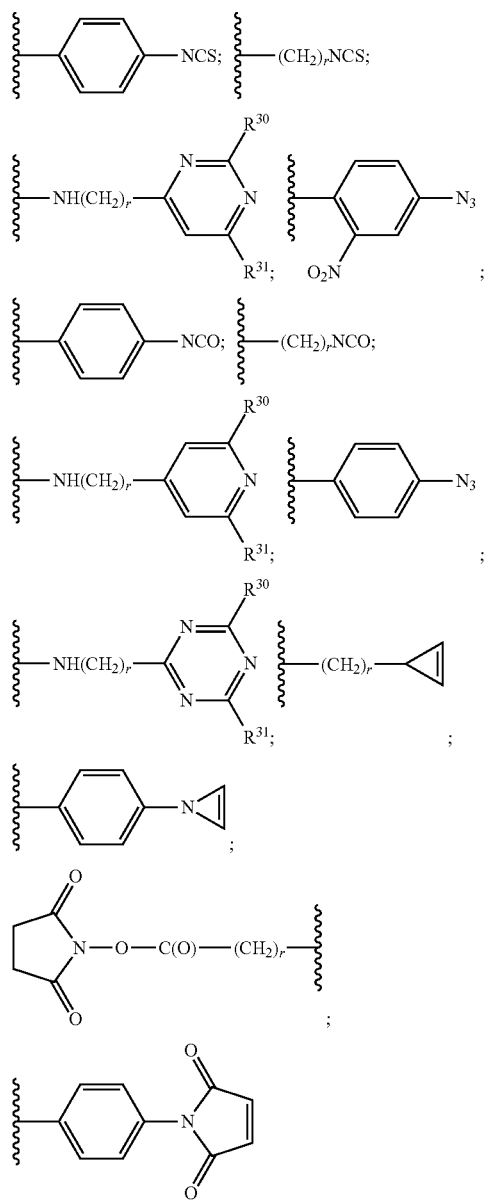

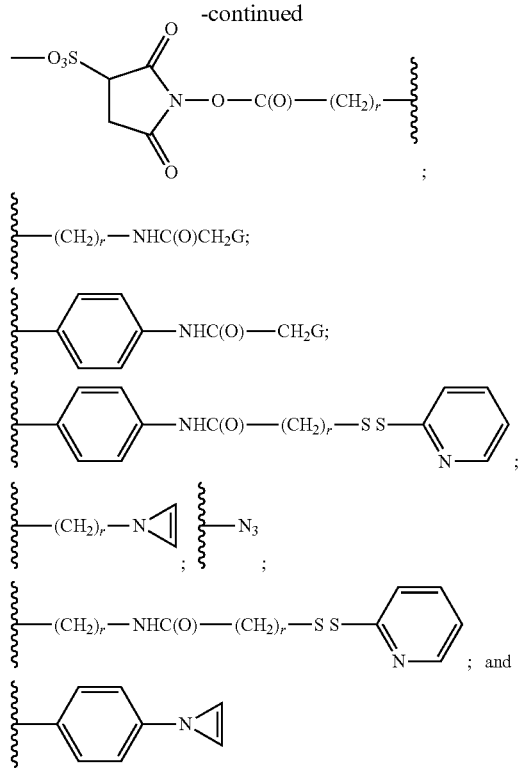

wherein
each r is independently selected from the integers from 1 to 10;
G is a halogen; and
R$^{30}$ and R$^{31}$ are members independently selected from H and halogen and at least one of R$^{30}$ and R$^{31}$ is halogen.

18. The compound or conjugate according to claim 1, wherein said carrier molecule comprises the structure:

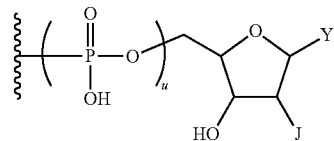

wherein
u is selected from the integers from 1 to 8;
J is a member selected from H, OH, and OMe; and
Y is a nucleobase.

19. The compound or conjugate according to claim 1, having a formula which is a member selected from:

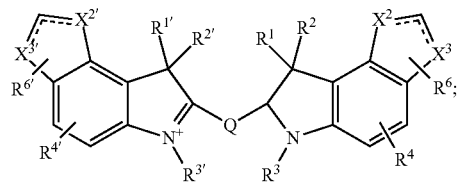

129

-continued

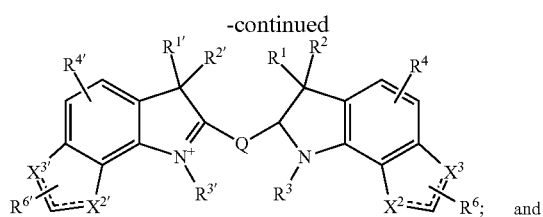

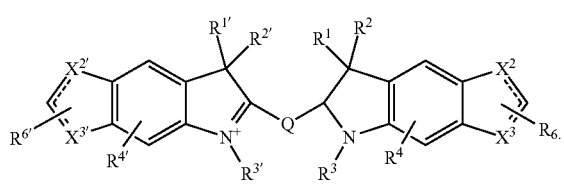

wherein,
each $R^4$, $R^{4'}$, $R^6$ or $R^{6'}$ moiety is independently selected and when said compound includes more than one $R^4$, $R^{4'}$, $R^6$ or $R^{6'}$ moiety, each $R^4$, $R^{4'}$, $R^6$ or $R^{6'}$ moiety is independently selected.

20. The compound or conjugate according to claim 19, having a formula selected from:

130

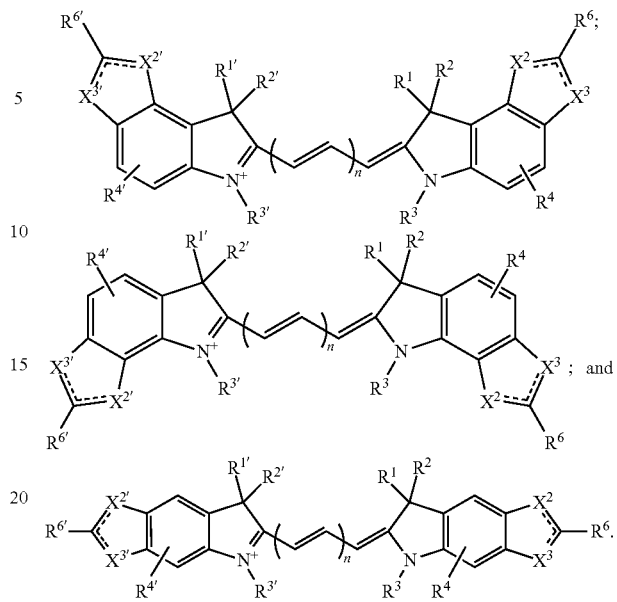

21. The compound or conjugate according to claim 1 having a formula selected from:

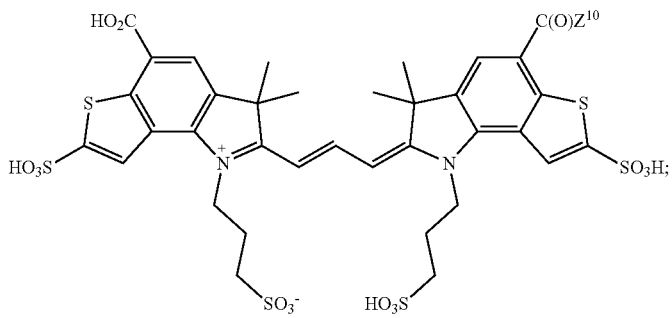

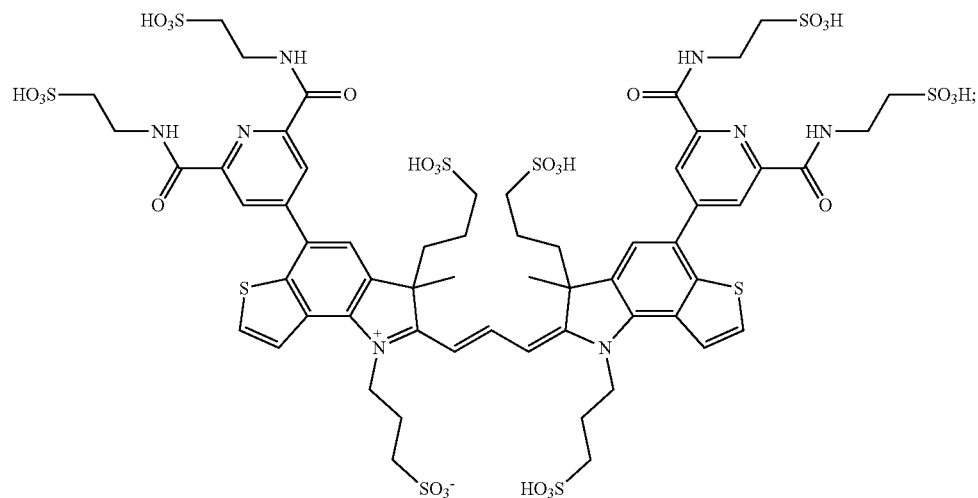

-continued
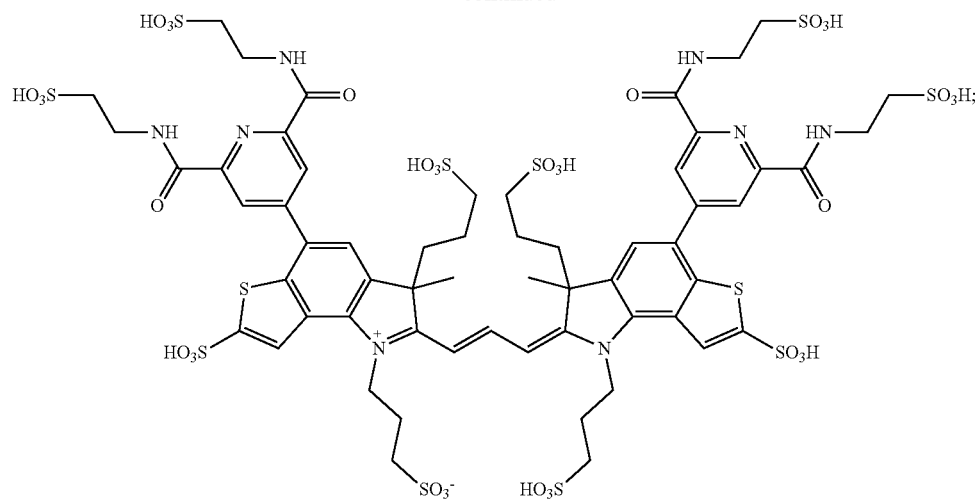
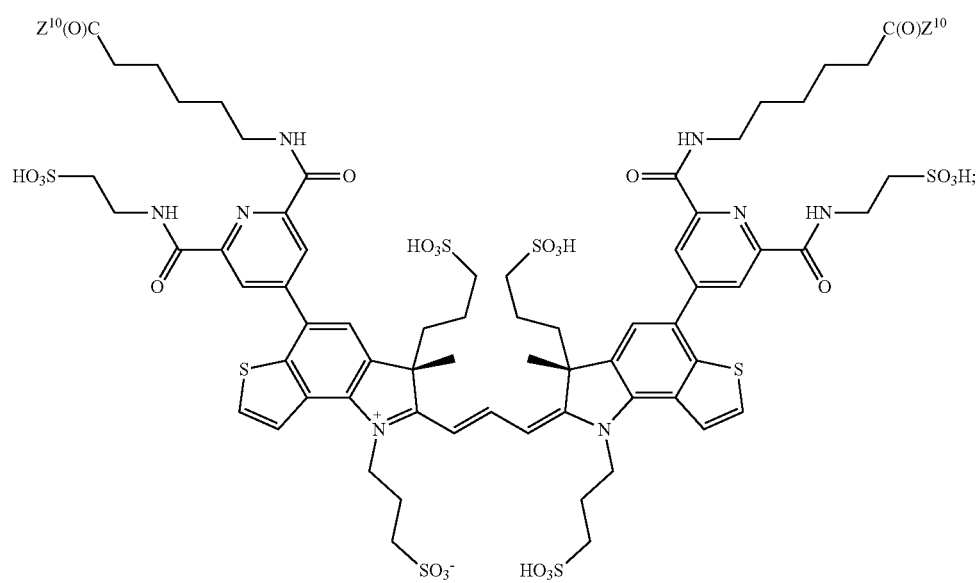
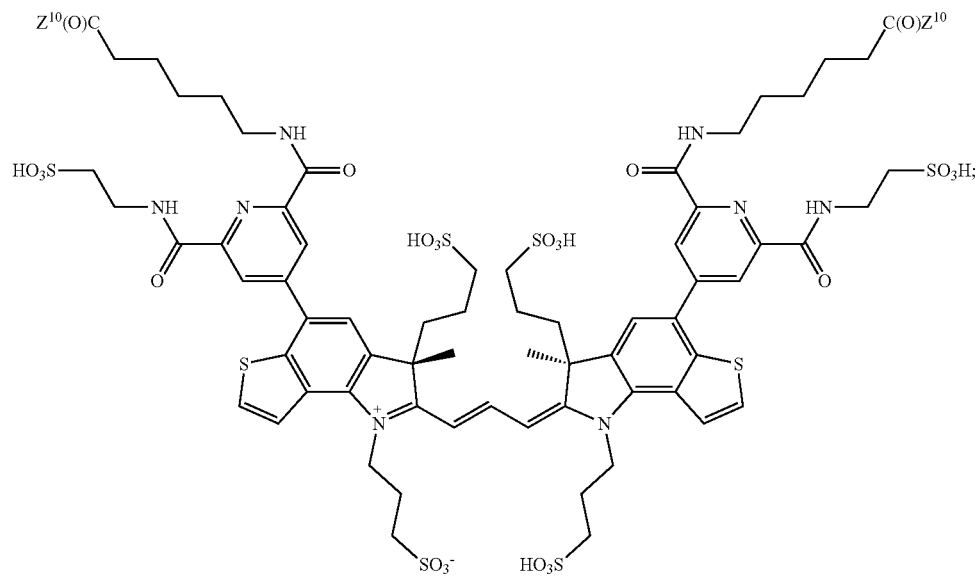

-continued
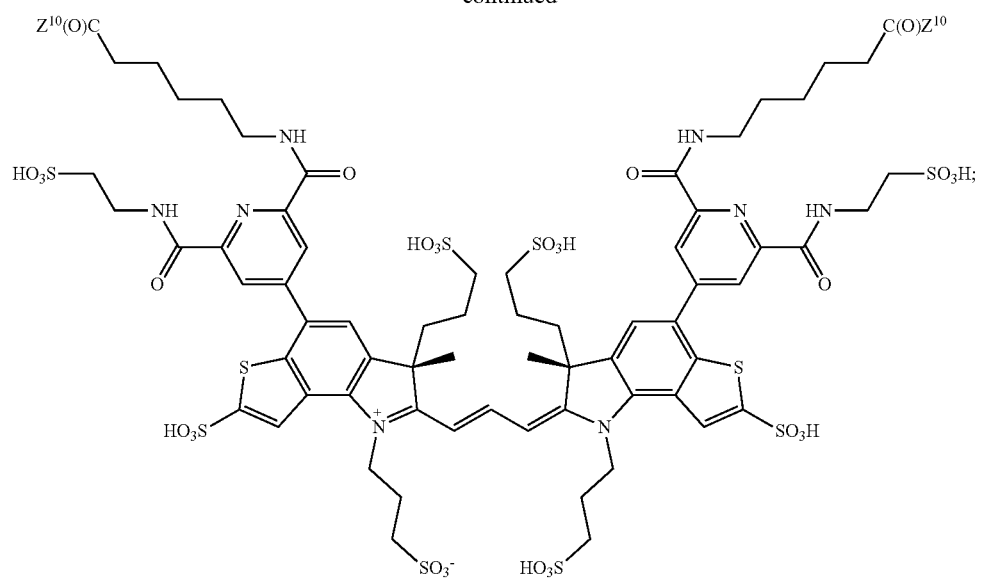
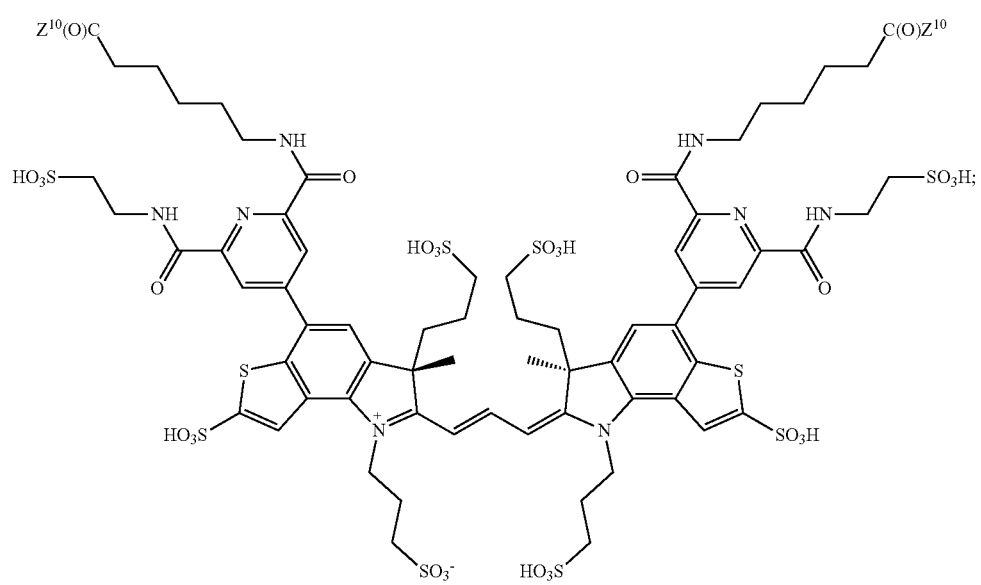
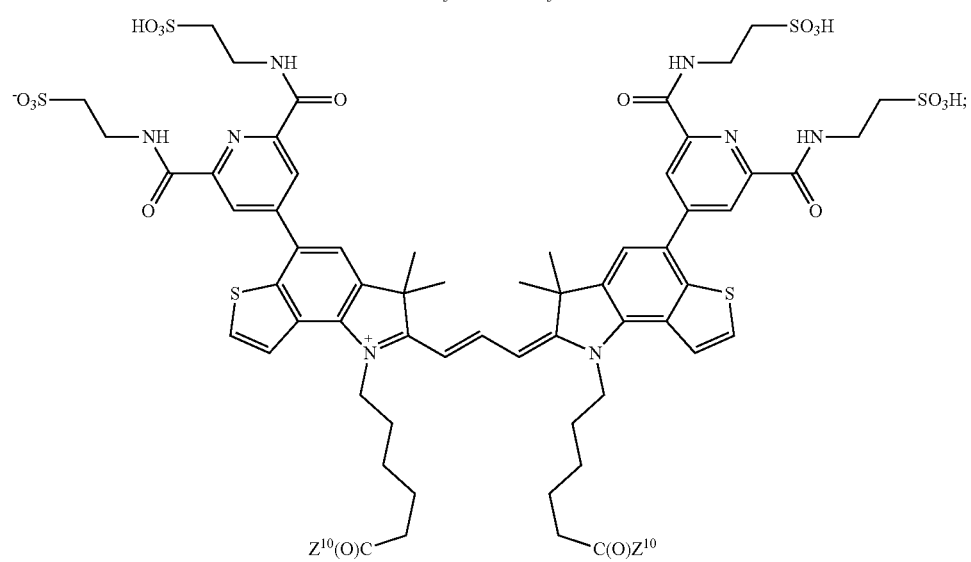

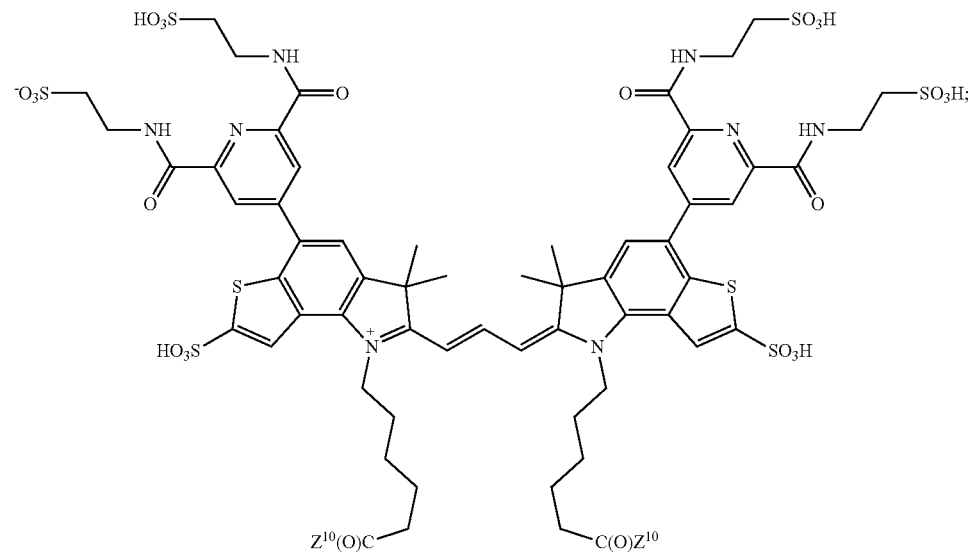
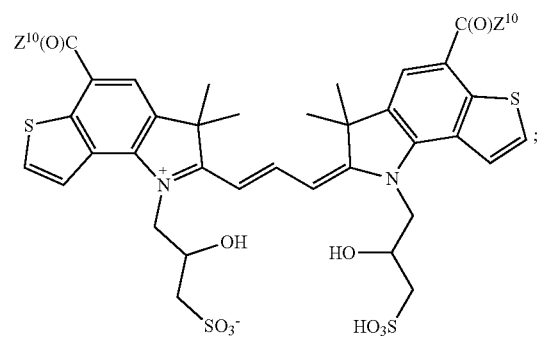
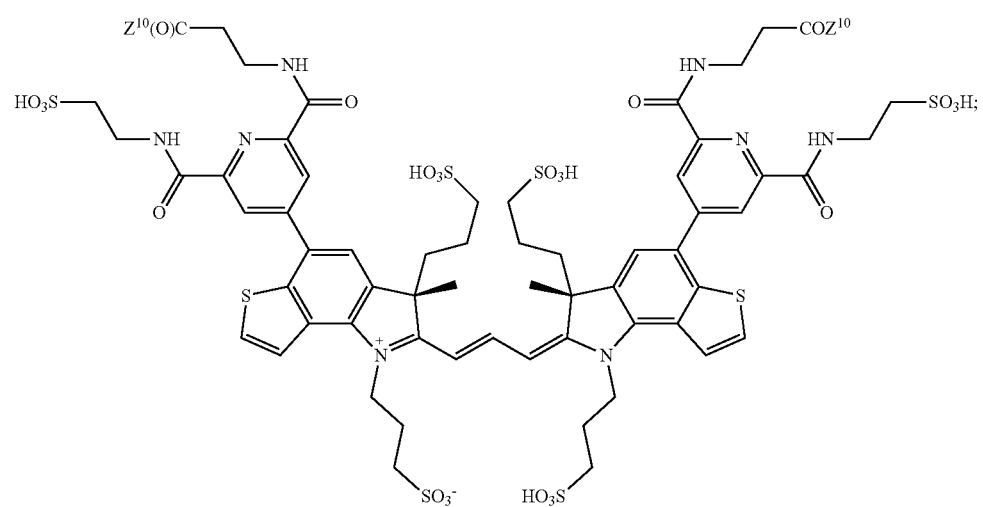

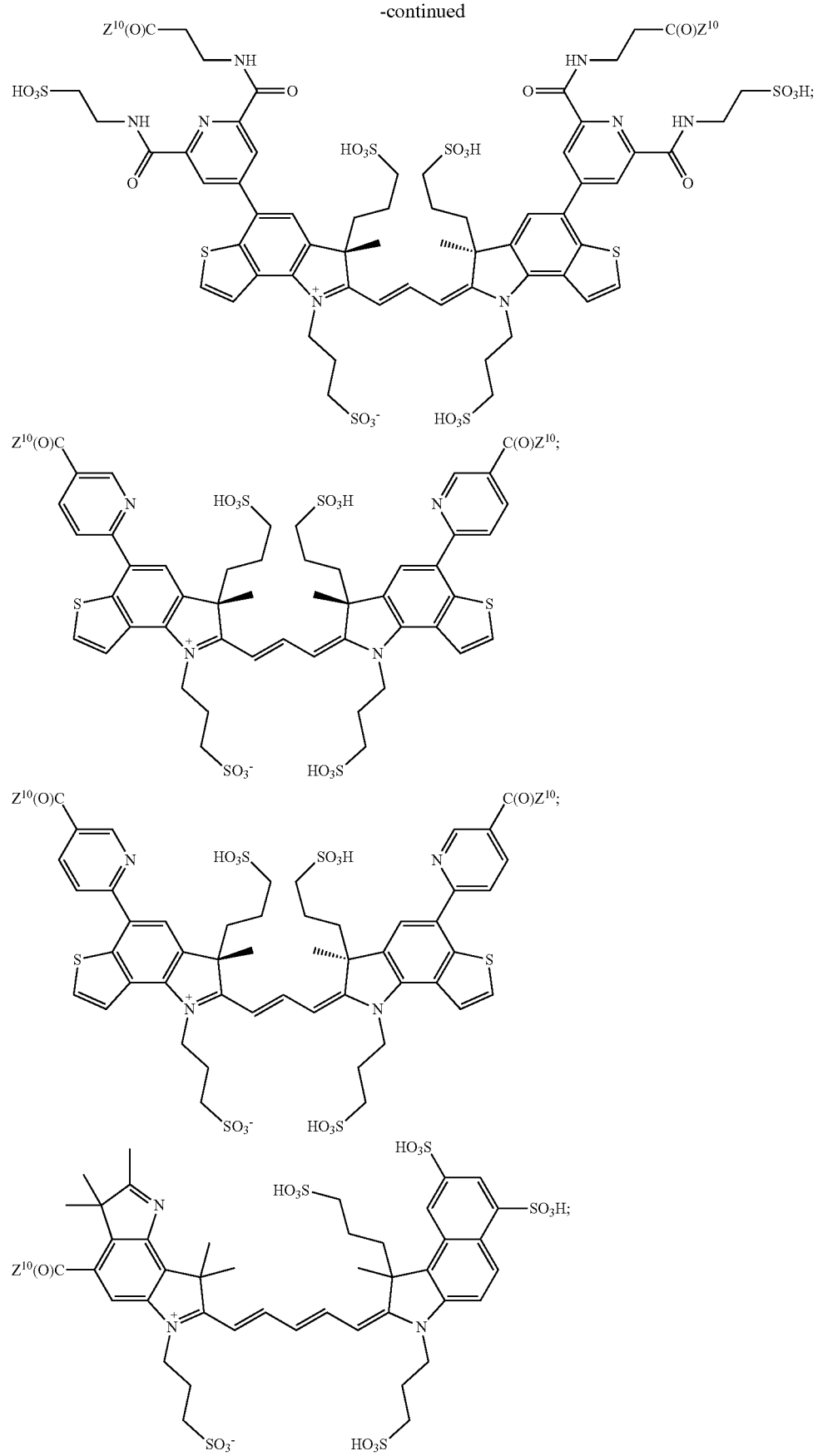

-continued
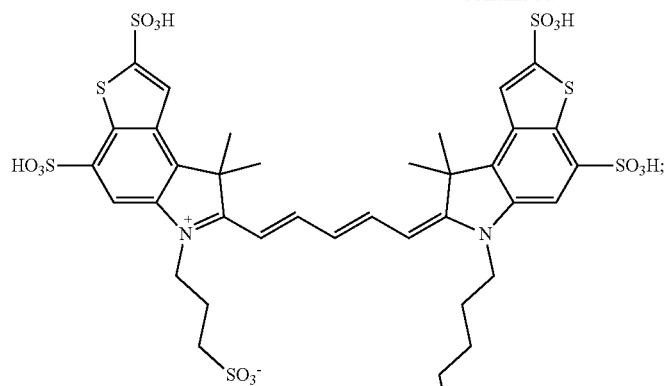
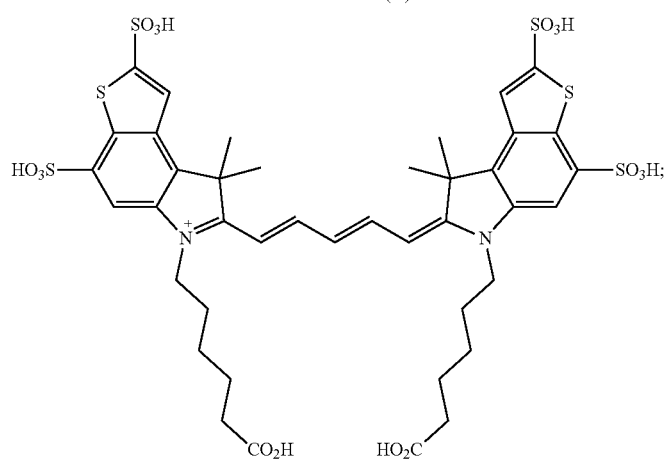
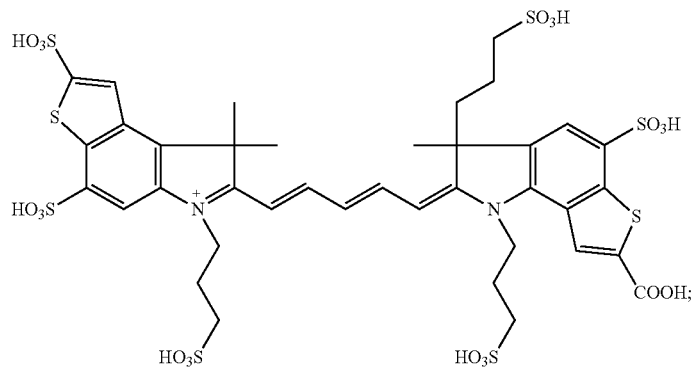
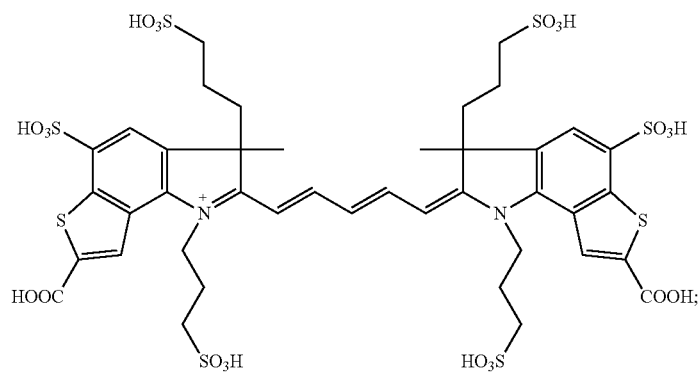

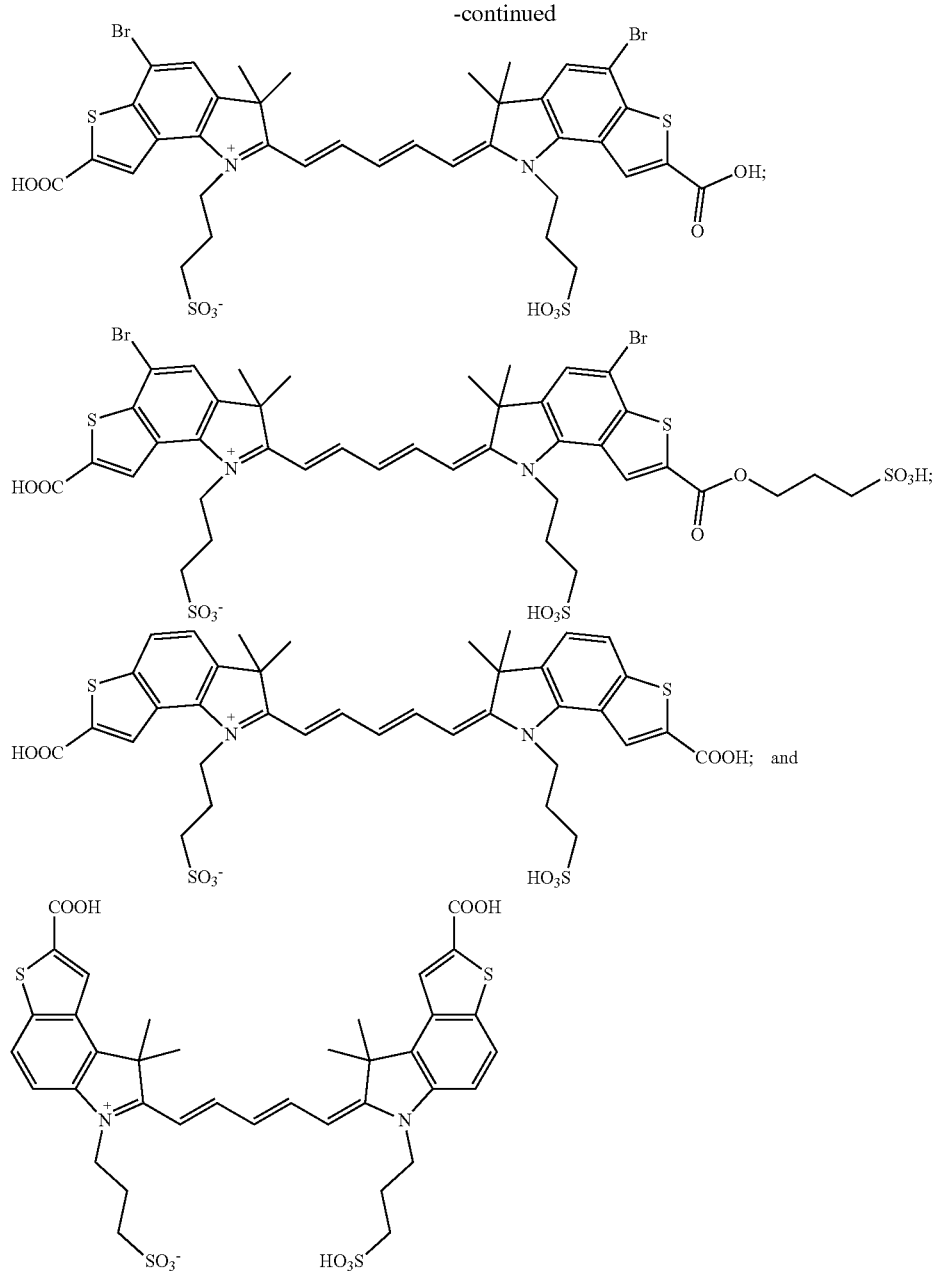

wherein $Z^{10}$ is OH, O⁻, said reactive functional group, said component of a reactive functional group or said linkage fragment covalently binding said compound to a carrier molecule; and when said compound has more than one $Z^{10}$ moiety, each $Z^{10}$ moiety is independently selected.

22. The compound or conjugate according to claim 1, wherein $R^{28}$ is substituted alkyl having from 1 to 20 carbon atoms.

23. The compound or conjugate according to claim 22, wherein said substituted alkyl is haloalkyl.

24. The compound or conjugate according to claim 23, wherein said haloalkyl is —CF$_3$.

25. The compound or conjugate according to claim 1, wherein $R^{28'}$ is substituted alkyl having from 1 to 20 carbon atoms.

26. The compound or conjugate according to claim 25, wherein said substituted alkyl is haloalkyl.

27. The compound or conjugate according to claim 26, wherein said haloalkyl is —CF$_3$.

28. A method of monitoring an enzyme reaction, said method comprising:
(a) forming a reaction mixture by contacting said enzyme with a fluorescent compound or conjugate according to claim 1, wherein said compound or conjugate is a substrate for said enzyme under conditions sufficient for said enzyme and said compound or conjugate to react; and
(b) monitoring fluorescence of said reaction mixture.

29. The method according to claim 28 wherein, said enzyme is a DNA polymerase and said compound or conjugate comprises a nucleic acid moiety which is said substrate for said enzyme.

30. The method according to claim 28, wherein said enzyme reaction is template directed DNA synthesis.

31. The method according to claim 28, wherein said reaction is a component of a single molecule DNA sequencing analysis.

* * * * *